US010045951B2

(12) United States Patent
Christofidou-Solomidou

(10) Patent No.: US 10,045,951 B2
(45) Date of Patent: Aug. 14, 2018

(54) FLAXSEED LIGNAN COMPLEX AND ITS USE THEREOF

(75) Inventor: Melpo Christofidou-Solomidou, Eagleville, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 34 days.

(21) Appl. No.: 13/084,408

(22) Filed: Apr. 11, 2011

(65) Prior Publication Data

US 2011/0300247 A1    Dec. 8, 2011

Related U.S. Application Data

(63) Continuation-in-part of application No. 12/601,882, filed as application No. PCT/US2008/006694 on May 27, 2008.

(60) Provisional application No. 60/924,678, filed on May 25, 2007.

(51) Int. Cl.
| | |
|---|---|
| *A61K 31/065* | (2006.01) |
| *A61K 31/365* | (2006.01) |
| *A61K 31/7032* | (2006.01) |

(52) U.S. Cl.
CPC .......... *A61K 31/065* (2013.01); *A61K 31/365* (2013.01); *A61K 31/7032* (2013.01)

(58) Field of Classification Search
None
See application file for complete search history.

(56) References Cited

U.S. PATENT DOCUMENTS

| | | | |
|---|---|---|---|
| 6,407,075 B1 * | 6/2002 | Scott et al. .................. | 514/34 |
| 6,486,126 B1 * | 11/2002 | Prasad .......................... | 514/25 |
| 6,673,773 B2 | 1/2004 | Prasad | |
| 2004/0229038 A1 * | 11/2004 | Cooper .................. | A61K 9/145 428/402.21 |
| 2006/0052438 A1 | 3/2006 | Ho et al. | |
| 2006/0148732 A1 | 7/2006 | Gutterman et al. | |
| 2007/0087063 A1 | 3/2007 | Bland et al. | |

FOREIGN PATENT DOCUMENTS

| | | |
|---|---|---|
| JP | 2005278429 A * | 10/2005 |
| WO | WO 02092073 A1 * | 11/2002 |

OTHER PUBLICATIONS

Mayo Clinic Staff. "Lung Cancer". Internet publication date: Apr. 17, 2012 [Retrieved from the Internet on: Aug. 23, 2012]. Retrieved from the Internet: <URL: http://www.mayoclinic.com/health/lung-cancer/DS00038/METHOD=print&DSECTION=all>.*
Eldridge, L. "What is Pulmonary Pneumonitis?" Internet publication date: Feb. 25, 2011 [Retrieved from the Internet on: Aug. 23, 2012]. Retrieved from the Internet: <URL: http://lungcancer.about.com/od/treatmentoflungcancer/a/radpneumonitis.htm?p=1>.*
Daniells, S. "Flaxseed could boost lung health, animal study". Internet publication date: May 24, 2006 [Retrieved from the Internet on: Aug. 23, 2012]. Retrieved from the Internet: <URL: http://www.nutraingredients.com/Research/Flaxseed-could-boost-lung-health-animal-study>.*
"American Institute for Cancer Research". AICR ScienceNow. vol. 8 (Fall 2006). Retrieved from the Internet on: Apr. 16, 2013. Retrieved from: <URL: http://preventcancer.aicr.org/site/News2?page=NewsArticle&id=11325&news_iv_ctrl=0&abbr=res_>.*
Kinniry et al. J Nutr. Jun. 2006;136(6):1545-1551.*
Inskip et al. Lung cancer risk and radiation dose among women treated for breast cancer. J Natl Cancer Inst. Jul. 6, 1994;86(13):983-8.*
Lee et al. Apr. 2007 The FASEB Journal vol. 21 No. 5 A172.*
Lee et al. Apr. 2007 The FASEB Journal vol. 21 No. 5 A61.*
Kinniry et al. J. Nutr. Jun. 2006 vol. 136 No. 6 1545-1551.*
Kinniry, P, et al. Dietary flaxseed supplementation ameliorates inflammation and oxidative tissue damage in experimental models of acute lung injury in mice. J. Nutrition, 2006, vol. 136, No. 6, pp. 1545, 1546, 1548, 1549.
Muzykantov et al. "Targeting of superoxide dismutase and catalase to vascular endothelium" Journal of Controlled Release vol. 71, Issue 1, pp. 1-21, Mar. 12, 2001.
Kozower, B.D., M. Christofidou-Solomidou, T.D. Sweitzer, S. Muro, D.G. Buerk, C.C. Solomides, S.M. Albelda, G.A. Patterson, and V.R. Muzykantov. 2003. Immunotargeting of catalase to the pulmonary endothelium alleviates oxidative stress and reduces acute lung transplantation injury. *Nat Biotechnol* 21:392-398.
Wakabayashi, N., Itoh, K., Wakabayashi, J., Motohashi, H., Noda, S., Takahashi, S., Imakado, S., Kotsuji, T., Otsuka, F., Roop, D.R., Harada, T., Engel, J.D., and Yamamoto, M. (2003). Keap1-null mutation leads to postnatal lethality due to constitutive Nrf2 activation. Nat Genet 35, 238-245.
Ikeda, T., Y. Nishijima, H. Shibata, Y. Kiso, K. Ohnuki, T. Fushiki, and T. Moritani. 2003. Protective effect of sesamin administration on exercise-induced lipid peroxidation. *Int J Sports Med* 24:530-534.
Prasad, K., S.V. Mantha, A.D. Muir, and N.D. Westcott. 1998. Reduction of hypercholesterolemic atherosclerosis by CDC-flaxseed with very low alpha-linolenic acid. *Atherosclerosis* 136:367-375.
Pattanaik, U., and K. Prasad. 1998. Oxygen Free Radicals and Endotoxic Shock: Effect of Flaxseed. *J Cardiovasc Pharmacol Ther* 3:305-318.
Lee, et al., "Dietery flaxseed enhances antioxidant defenses and is protective in a mouse model of lung ischemia-reperfusion injury", Am. J. Physiol. Lung Cell Mol. Physiol. 294(2): L255-65, 2008.
Lee, et al., "Dietery Flaxseed prevents radiation induced oxidative lung damage inflammation and fibrosis in a mouse model of thoracic radiation injury", Cancer Biology and Therapy, 8(1), 47-53, 2009.
Govt of India; Ayurvedic Formulary of India—Part H, Govt of India, Ministry of Health & Family Welfare, Dcptt. Ofl.S.M. &H., New Delhi, Edn. 1st [This book contains back references from 1000 B.C.to 20th century] p. 69 , (2000).

(Continued)

*Primary Examiner* — Amy L Clark
(74) *Attorney, Agent, or Firm* — Mark S. Cohen; Pearl Cohen Zedek Latzer Baratz LLP

(57) ABSTRACT

The invention relates compositions and methods for treating pathological lung conditions using whole-grain flaxseed or flaxseed lignans. Specifically, the invention relates to the dietary use of flaxseed lignans.

8 Claims, 39 Drawing Sheets

(56) References Cited

OTHER PUBLICATIONS

Ziya Al-Din Abdullah Ibn Al-Baiter; AMaam'e-ii-Mufradaat-al-Advia-w ai-Aghzia, vol. I (3th century AD), Matba Amra, Cairo, Egypt, p. 90, 1874 AD.

Mohammad Azarn Khan; Muheet-e-Azam vol. IV (Part I) {19th century AD), Matba Nizami, Kanpur, p. 35, 1899 AD.

Ali Ibn-e-Abbaas Majoosi; Kaamil-al-Sena'ah, Part II (10th century AD), Central Council for Research in Unani Medicine, 61-65 Institutional Area, Janak Puri, New Delhi—58, 2005 AD, p. 54.

Mohammad Akbar Arzani; Qaraabaadeen Qaadri (17th century AD), Ahmade Publication, Delhi, 1968 AD, p. 131.

Mohammad Kabiruddin, "Laooq Katan" from Bayaaz-e-Kabir, vol. II, (Compiled), Daftar al-Maseeh, Karol Bagh, New Delhi, 1938, p. 149.

Prasad, Kailash, "Hypocholesterolemic and antiatherosclerotic effect of flax lignan complex isolated from flaxseed", Atherosclerosis 179 (2005) 269-275.

Abu Bakr Mohammad.Bin Zakariyya Al-Razi; Kitaab-al-Haawi-fil-Tibb, vol. IV (9th century AD), Dayerah-al-Ma'aarif Usmania, Hyderabad, 1978 AD, p. 90.

Abu Bakr Mohammad.Bin Zakariyya Al-Razi; Kitaab-al-Haawi-fil-Tibb, vol. IV (9th century AD), Dayerah-al-Ma'aarif Usmania, Hyderabad, 1978 AD, p. 198.

Abu Ali Ibn-e-Sina; Al-Qaanoon-fil-Tibb, vol. V (11th century AD), Publication Department, Jamia Hamdard, New Delhi—62, 1996 AD, p. 199.

Abu Bakr Mohammad.Bin Zakariyya Al-Razi; Kitaab-al-Haawi-fil-Tibb, vol. IV (9th century AD), Dayerah-al-Ma'aarif Usmania, Hyderabad, 1978 AD, p. 25-147.

Abu Bakr Mohammad.Bin Zakariyya Al-Razi; Kitaab-al-Haawi-fil-Tibb, vol. IV (9th century AD), Dayerah-al-Ma'aarif Usmania, Hyderabad, 1978 AD, p. 25-26.

Daniells, S. "Flaxseed could boost lung health, animal study", Internet publication date: May 24, 2006, Retrieved from the internet: <URL: http://www.nutraingredients.com/Research/Flaxseed-could-boost-lung-health-animal-study>.

\* cited by examiner (Top)

(top)

(bottom)

FLAXSEED LIGNAN COMPLEX AND ITS USE THEREOF

CROSS-REFERENCE TO RELATED APPLICATIONS

This is a continuation-in-part application of U.S. patent application Ser. No. 12/601,882, filed Jun. 1, 2010, which is a national stage application of PCT Patent Application PCT/US2008/006694, filed May 27, 2008 that claims priority to U.S. Provisional Patent Application 60/924,678, filed May 25, 2007, all of which are incorporated by reference herein in their entirety.

GOVERNMENT INTEREST

The work described in this application was supported, in whole or in part, by grants from the National Institute of Health (Grant Numbers NIH-R01 CA133470-03, NIH-RC1 AI081251-01, NIH-P30 CA016520). The United States government may have certain rights in the invention.

FIELD OF THE INVENTION

The invention relates to compositions and methods for treating pathological lung conditions using whole-grain flaxseed or flaxseed lignans. Specifically, the invention relates to the use of dietary flaxseed or flaxseed lignans.

BACKGROUND OF THE INVENTION

It has long been recognized that when oxygenation is restored in hypoxic tissues (re-oxygenation), hypoxic tissue injury is further augmented, a process called ischemia-reperfusion injury (IRI). This mechanism of cellular injury is especially prominent in surgical, myocardial, hepatic, intestinal, cerebral, renal, and other ischemic syndromes and occurs, with varying degrees of severity, after all forms of organ transplantation. Vascular oxidative stress is also a major cause of pulmonary and systemic pathology in conditions including Acute Lung Injury (ALI/ARDS), inflammatory lung conditions, sepsis, hyperoxia and radiation injury.

Vascular I/R is responsible for acute graft failure and delayed complications of organ transplantation and cardiopulmonary bypass, as well as necrotic and apoptotic tissue injury in acute myocardial infarction (AMI), stroke, thrombosis and other cases of occlusive ischemia of vessels that perfuse blood to internal organs or extremities.

Oxidative stress in general, is characterized by the formation of reactive oxygen species (ROS) such as superoxide anion, hydrogen peroxide, and hydroxyl radical. These molecules are highly reactive and react with structures such as DNA, key cellular proteins, and the lipid component of the cell membrane leading to lipid peroxidation and subsequent cell injury that can be detected by increased permeability, and in more severe cases to cell lysis. The generation of intracellular ROS occurs in most lung parenchymal cells, such as endothelial cells, Type II alveolar epithelial cells, Clara cells, alveolar epithelial cells as well as in alveolar macrophages (See FIG. 1—taken from Muzykantov, V. R. 2001. Targeting of superoxide dismutase and catalase to vascular endothelium. *J Controlled Release* 71:1-21).

There are at least two important mechanisms for ROS production during IRI. During anoxia, hypoxanthine accumulates and the enzyme xanthine dehydrogenase is converted into xanthine oxidase. This is followed by the degradation of hypoxanthine into superoxide which occurs during deoxygenation. The other mechanism depends on the NADPH oxidase system, which is present mainly on the membrane surface of neutrophils and monocytes/macrophages and endothelial cells and catalyzes the reduction of oxygen into hydrogen peroxide and superoxide anion. Classically, it has been thought that such activated neutrophils contribute to vascular reperfusion injury, although cellular injury is propagated in the absence of inflammatory cells through mechanisms involving reactive oxygen (ROS) or nitrogen species (RNS).

In addition to leukocyte ROS, generation of ROS thereby endothelial cells through this pathway also appears to be important. Studies from our group and others indicate that vascular oxidative stress induced by ROS, (including superoxide anion and $H_2O_2$) plays a key role in ischemia-reperfusion (I/R) injury. Endothelial cells (EC), which line the luminal surface of blood vessels and control vascular tone, transport of blood components to tissues and maintain blood fluidity) represent a main target of ROS in I/R. EC dysfunction and damage induced by ROS thus play a key role in the initiation and propagation of I/R injury (See FIG. 1).

Ironically, intracellular ROS produced by EC themselves in response to ischemia (endogenous ROS production) help to initiate the injurious I/R cascade, while extracellular ROS (exogenous ROS production) released from activated white blood cells (WBC) augment and further propagate the vicious cycle and subsequent pathological reactions including WBC adherence, thrombosis, vascular edema and vasoconstriction, i.e., events initiated by EC damage.

Given this pathophysiology, many believe that I/R injury could be ameliorated or even prevented by effective ROS detoxification, thus justifying the interest in the development of antioxidant prophylaxis and therapies. Conventional antioxidants such as N-acetyl-cysteine (a precursor for a main cellular reducing agent, glutathione), selected vitamins (e.g., tocopherol) and food supplements (flavonoids) afford some degree of protection in selected cases of modest chronic oxidative stress. However, the potency of these antioxidants has not been sufficient to protect against severe acute and sub-acute forms of vascular oxidative stress, such as I/R. More effective approaches are therefore needed.

Correspondingly, lung transplantation has become an important therapy for many end-stage lung diseases. Unfortunately, due to the circulatory disruption required by transplantation, a significant cause of early morbidity and mortality associated with this procedure is ischemia-reperfusion-induced injury (IRI) of the lung. Oxidative stress, the key mediator of IRI, typically manifests itself within the first 72 hours after transplantation and is characterized by alveolar damage, lung edema, and hyperemia. Despite advances in our understanding of the mechanisms of IRI, and improvements in the technique of lung preservation, in surgical techniques and in perioperative care, up to 15% of all transplanted lungs will end up with primary graft failure. Better ways to deliver potent and safe antioxidant agents are clearly needed.

The usefulness of thoracic radiotherapy is greatly limited by the sensitivity of the lung tissue to irradiation doses necessary to eradicate malignant cells. Clinically significant radiation lung injury, such as pneumonia-like inflammation and late stage fibrosis, occurs in up to 30% of patients irradiated for lung cancer and about 10-15% of other thoracic oncology patients. The need, however, to protect "normal" lung parenchyma from unacceptable radiation injury compromises the ability to deliver tumoricidal radiotherapy doses and contributes to the high local recurrence rates experienced by lung cancer patients following definitive radiotherapy. The cytotoxic effects of ionizing radiation in normal lung parenchyma are mediated by the generation of reactive oxygen species (ROS) and propagated by ROS-driven oxidative stress thus identifying a central role of tissue antioxidant defense. A safe radioprotecting agent that would ameliorate radiation toxicity while not protecting tumor, or even preferably radiosensitizing tumor cells is desperately needed. We and others have shown that antioxidant enzyme therapy alleviates radiation-induced fibrotic lung disease. NF-E2-related factor 2 (Nrf2), a key transcriptional regulator for antioxidant response element (ARE) mediates induction of cellular antioxidant and detoxifying enzymes. Preliminary data obtained from an exploratory R21 award showed that whole grain dietary flaxseed (FS) boosts Nrf2-mediated antioxidant defense in murine lungs. Importantly, dietary whiole-grain FS ameliorated the adverse effects of thoracic radiation by enhancing survival and blocking lung fibrosis while, remarkably inhibiting lung tumor growth and metastasis. We have evidence to believe that the bioactive ingredient(s) in the FS grain that mediate these effects are the lignans. Flaxseed contains the lignan precursor secoisolariciresinol diglucoside (SDG) which is metabolized in the intestine to mammalian lignans which are safe, compounds with known antioxidant, anti-inflammatory and anticarcinogenic effects. Our group discovered that chemically synthesized, commercially available flaxseed lignans, activate the Nrf2/ARE pathway mediating transcription of antioxidant enzyme genes and inhibit lung cancer cell proliferation in vitro. Additional evidence revealed proteasomal inhibition as a potential mechanism of their action. Therefore, coordinate induction of Nrf2/ARE regulated antioxidant genes by flaxseed lignans can be a therapeutic strategy to alleviate radiation pneumonopathy and that these agents are responsible for inhibition of lung tumor growth and metastasis.

SUMMARY OF THE INVENTION

In one embodiment, the invention provides a method for treating a lung disease in a subject, the method comprising: administering to said subject an effective amount of flaxseed, its bioactive ingredient, or a metabolite thereof, thereby treating said lung disease in said subject.

In another embodiment, the invention provides a method for treating a pneumonopathy in a subject, the method comprising: administering to said subject an effective amount of flaxseed, its bioactive ingredient, or a metabolite thereof, thereby treating said pneumonopathy in said subject.

In another embodiment, the invention provides a composition for treating a lung disease in a subject, the composition comprising an effective amount of flaxseed, its bioactive ingredient, or a metabolite thereof.

In another embodiment, the invention provides a method for therapeutically treating a radiation-induced lung disease in a subject, the method comprising: administering to said subject a therapeutically effective amount of flaxseed, its bioactive ingredient, or a metabolite thereof, thereby treating said radiation-induced lung disease in said subject.

In another embodiment, the invention provides a method for therapeutically treating a radiation-induced pneumonopathy in a subject, the method comprising: administering to said subject a therapeutically effective amount of flaxseed, its bioactive ingredient, or a metabolite thereof, thereby treating said radiation-induced pneumonopathy in said subject.

In another embodiment, the invention provides a method for therapeutically treating a radiation pneumonitis in a subject, the method comprising: administering to said subject a therapeutically effective amount of flaxseed, its bioactive ingredient, or a metabolite thereof, thereby treating said radiation pneumonitis in said subject.

In another embodiment, the invention provides a composition for therapeutically treating a radiation-induced lung disease in a subject, the composition comprising a therapeutically effective amount of flaxseed, its bioactive ingredient, or a metabolite thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings.

DETAILED DESCRIPTION OF THE INVENTION

Figure 1:
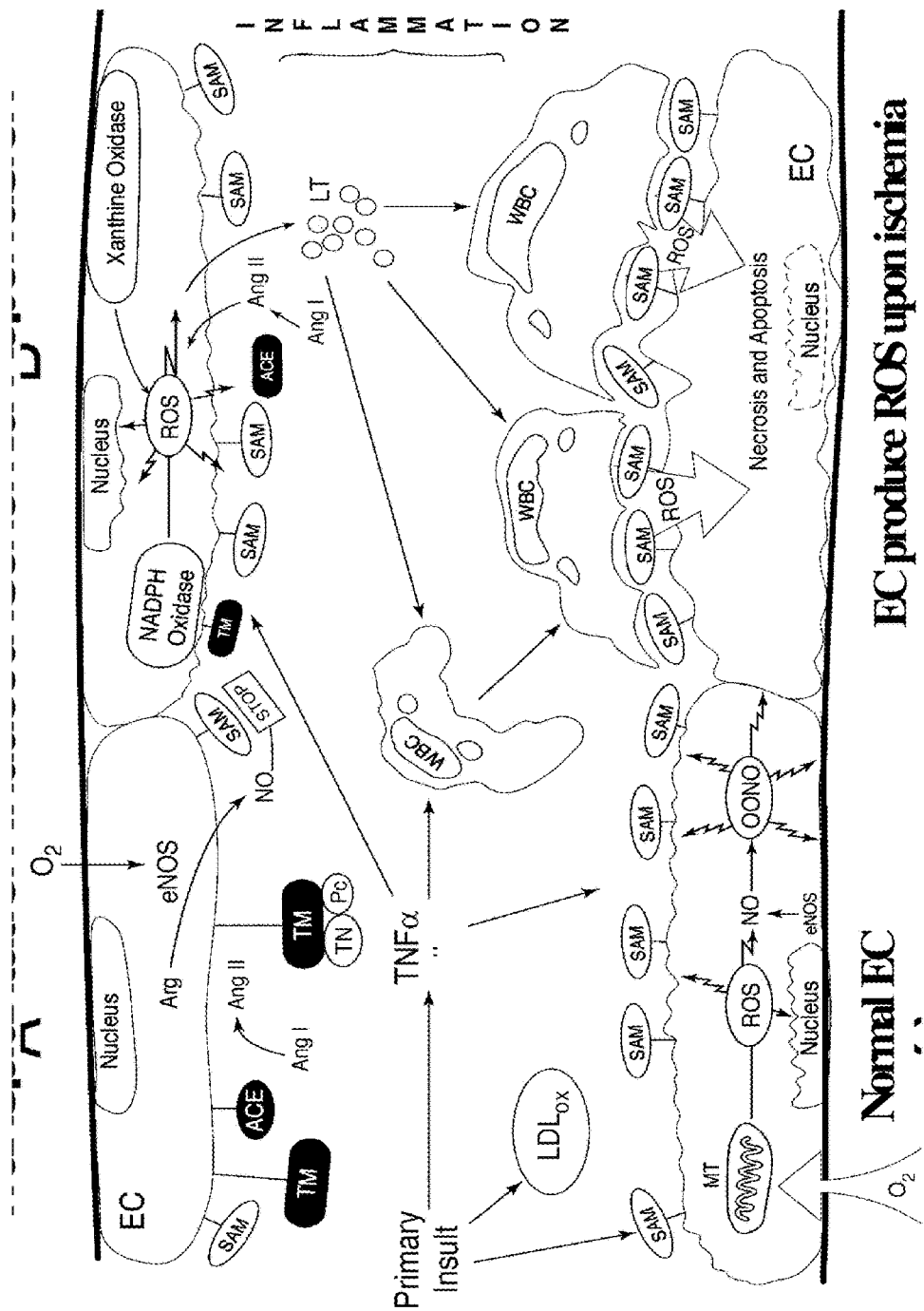
FIG. 1: shows endothelial cell oxidative stress in lung transplantation-induced ischemia reperfusion; taken from Muzykantov, V. R. 2001. Targeting of superoxide dismutase and catalase to vascular endothelium. *J Controlled Release* 71:1-21).

The invention relates to compositions and methods for treating pathological lung conditions using whole-grain flaxseed or flaxseed lignans. Specifically, the invention relates to the use of dietary flaxseed or flaxseed lignans.

In one embodiment, provided herein is a method for treating a lung disease in a subject, the method comprising: administering to said subject an effective amount of flaxseed, its bioactive ingredient, or a metabolite thereof, thereby treating said lung disease in said subject. In another embodiment, provided herein is a method for treating a pneumonopathy in a subject, the method comprising: administering to said subject an effective amount of flaxseed, its bioactive ingredient, or a metabolite thereof, thereby treating said pneumonopathy in said subject.

In another embodiment, provided herein is a method for therapeutically treating a radiation-induced lung disease in a subject, the method comprising: administering to said subject a therapeutically effective amount of flaxseed, its bioactive ingredient, or a metabolite thereof, thereby treating said radiation-induced lung disease in said subject. In another embodiment, provided herein is a method for therapeutically treating a radiation-induced pneumonopathy in a subject, the method comprising: administering to said subject a therapeutically effective amount of flaxseed, its bioactive ingredient, or a metabolite thereof, thereby treating said radiation-induced pneumonopathy in said subject. Examples of a radiation-induced lung disease or pneumonopathy include, but are not limited to, radiation-induced pulmonary fibroses, radiation-induced lung inflammation, radiation-induced lung injury, and radiation pneumonitis.

In another embodiment, provided herein is a composition for treating a lung disease in a subject, the composition comprising an effective amount of flaxseed, its bioactive ingredient, or a metabolite thereof. In another embodiment, provided herein is a composition for therapeutically treating a radiation-induced lung disease in a subject, the composition comprising a therapeutically effective amount of flaxseed, its bioactive ingredient, or a metabolite thereof.

In one embodiment, provided herein is a method for treating ischemia-reperfusion injury (IRI) in a subject, the method comprising: administering to said subject an effective amount of flaxseed, its bioactive ingredient, or a metabolite thereof, thereby treating said lung disease in said subject.

In one embodiment, the term "ischemia-reperfusion injury (IRI)" refers to the process occurring when oxygenation is restored in hypoxic tissues (re-oxygenation), further augmenting hypoxic tissue injury. This mechanism of cellular injury is prominent in one embodiment, in surgical circumstances, or myocardial, hepatic, intestinal, cerebral, renal, and other ischemic syndromes in other embodiments, and occurs in another embodiment, with varying degrees of severity, after all forms of organ transplantation. In another embodiment, vascular oxidative stress is a major cause of pulmonary and systemic pathology in conditions including Acute Lung Injury (ALI/ARDS) in one embodiment, or inflammatory lung conditions, sepsis, hyperoxia and radiation injury in other embodiments. In another embodiment "Ischemia" or an "ischemic event" refers to an insufficient supply of blood to a specific cell, tissue or organ. A consequence of decreased blood supply is in another embodiment, an inadequate supply of oxygen to the organ or tissue (hypoxia). Prolonged hypoxia result in one embodiment, in an injury to the affected organ or tissue.

In one embodiment, the term "Anoxia" refers to a virtually complete absence of oxygen in the organ or tissue, which, if prolonged, may result in death of the cell, organ or tissue. In another embodiment, the term "Hypoxia" or a "hypoxic condition" refers to condition under which a cell, organ or tissue receives an inadequate supply of oxygen. In one embodiment, the term "Ischemic injury" refers to cellular and/or molecular damage to an organ or tissue or cell as a result of a period of ischemia. In another embodiment, the term "Hypoxic injury" refers to damage to a cell, organ, or tissue due to a period of inadequate oxygen supply. In one embodiment, the term "Reperfusion" refers to return of fluid flow into a tissue after a period of no-flow or reduced flow. For example in one embodiment, in reperfusion of the heart, fluid or blood returns to the heart through a supply line, such as the coronary arteries in vivo, after removal of an occlusion to the fluid or blood supply.

Flaxseed is grown in one embodiment, for its oil content for use primarily as an industrial oil. In another embodiment, flax is a rich source of fatty acids and has increasing uses in foods. In another embodiment, lignans, a component of Flaxseed refer in another embodiment to dimers containing a dibenzylbutane skeleton. When part of the human diet, such compounds are converted in another embodiment into mammalian lignans known as enterolactone (EL) and in another embodiment, to enterodiol (ED). In one embodiment, whole flaxseed flour and its deflated meal are the highest mammalian lignan producers, the meal and flour being 75 times higher than the next ranking entry, a seaweed, and over 100 times greater than most common foodstuffs. The principal lignan found in flaxseed is secoisolariciresinol diglucoside, referred to in certain embodiments, as SDG.

Flaxseed contains in one embodiment, 40% by weight fat ("linseed oil"). De-fatted (hexane-extracted) flax seed contains a residue of about 2% by wt. fat, with the remainder comprising: 46% by wt. fiber (both water-soluble fiber or "mucilage," acidic heterogeneous polysaccharides that contain galacturonic acid, galactose, rhamnose, and xylose, comprising 30-40% of the total fiber present, and water-insoluble fiber, which comprises 60-70% of the total fiber present); 10% total other carbohydrates, including lignans; 35% by wt. protein; 6-7% ash. In another embodiment, free SDG do not occur in the de-fatted flaxseed but is liberated by alkaline hydrolysis of various ester-linked polymers. In one embodiment, the available SDG in de-fatted flaxseed ranges from 0.9% to 3.0% by wt.

In one embodiment, Flaxseed (FS) is a useful antioxidant nutrient having high contents of omega-3 fatty acids and lignans that help reduce inflammation in one embodiment, and is helpful in treating a variety of cardiovascular and autoimmune diseases in other embodiments. Lignans, referring in another embodiment to widely occurring plant compounds that are closely related to lignin possess in another embodiment antioxidant properties. Secoisolariciresinol diglucoside (SDG) isolated from FS, is metabolized in the mammalian intestine to the lignans enterodiol (ED), and enterolactone (EL). In one embodiment, the oxygen radical scavenging properties of the FS lignans are operable in vitro by either direct hydroxyl radical scavenging activity, or by inhibition of lipid peroxidation in another embodiment. In one embodiment, due to the ability of lignans to act as platelet-activating-factor (PAF) antagonists, the lignan SDG exerts antioxidant activity by inhibiting reactive oxygen species (ROS) production by white blood cells.

Accordingly and in one embodiment, provided herein is a method of reducing acute lung inflammation, oxidative lung tissue injury or chronic lung fibrosis in a subject comprising administering to said subject a composition comprising a whole grain flaxseed, a bioactive ingredient or a metabolite thereof, whereby the bioactive flaxseed component or its metabolite(s) activates a transcription factor which modulates expression of protective enzymes, whereby in another embodiment the bioactive compound is whole grain flaxseed or an entire flaxseed lignan component (FLC).

In one embodiment, the intrapulmonary deposition of Endotoxin (LPS) from Gram-negative bacteria simulates bacterial pneumonia, a mode of injury characterized in one embodiment, by an intense local inflammatory response associated with diffuse neutrophilic infiltrate and cell damage that evolves over several days. In another embodiment, intratracheal instillation of bacterial LPS, simulating the effects of bacterial pneumonia, results in ALI within just 24 hours. In another embodiment, LPS activates alveolar macrophages and causes early infiltration of neutrophils further exacerbating the injury. In one embodiment, acid aspiration results in a dramatic increase of lung permeability, associated with WBC influx of predominantly PMN in the BAL.

In another embodiment, aspiration of gastric contents causes acute lung injury/acute respiratory distress syndrome (ALI/ARDS). Aspiration of gastric contents has been modeled in one embodiment, in mice by intratracheal instillation of hydrochloric acid. Aspirated HCl evoke in another embodiment, direct damage to the alveolar-capillary membrane and promote PMN adhesion, activation, and sequestration. In addition, HCL aspiration has been associated with thromboxane synthesis and generation of oxygen radicals associated with PMN activation. In another embodiment, the methods provided herein, using the compositions provided herein are effective for the treatment, or in another embodiment, in inhibiting or suppressing, or in yet another embodiment, in reducing the symptoms associated with acute lung inflammation, oxidative lung tissue injury or chronic lung fibrosis in a subject.

In one embodiment, the methods of treating acute lung inflammation, oxidative lung tissue injury or chronic lung fibrosis in a subject as provided herein, comprise contacting the subject with a composition comprising a whole grain flaxseed, a bioactive ingredient or a metabolite thereof, whereby the bioactive compound is whole grain flaxseed or flaxseed lignan metabolites.

In one embodiment, the primary lignan found in flaxseed is 2,3-bis(3-methoxy-4-hydroxybenzyl)butane-1,4-diol (secoisolariciresinol), which is stored in another embodiment as the conjugate secoisolariciresinol diglucoside (SDG) in its native state in the plant. In another embodiment, flaxseed contains levels of phytoestrogens which are 75-800 times greater than any other plant food. The plant lignan, catecholic nordihydroguaiaretic acid, is a potent antioxidant and is used in one embodiment in the compositions and methods provided herein.

In one embodiment, the whole grain flaxseed or flaxseed lignan complex (FLC) used in the methods and compositions provided herein, for treating acute lung inflammation, oxidative lung tissue injury or chronic lung fibrosis in a subject comprises the plant lignan precursor, secolsolariciresinol diglucoside (SDG). In another embodiment, the whole grain flaxseed or flaxseed lignan metabolites comprises the mammalian lignans enterodiol. In another embodiment, the whole grain flaxseed or flaxseed lignan metabolites comprises enterolactone, or in another embodiment, the whole grain flaxseed or flaxseed lignan metabolites comprises a combination thereof.

In another embodiment, provided herein is a method of reducing acute lung inflammation, oxidative lung tissue injury or chronic lung fibrosis in a subject comprising increasing dietary intake of a bioactive flaxseed component by the subject of the compositions provided herein, which in one embodiment comprise a whole grain flaxseed, a bioactive ingredient or a metabolite thereof, whereby the bioactive flaxseed component or its metabolite(s) activates a transcription factor which modulates expression of protective enzymes, thereby reducing inflammation and oxidative tissue injury, whereby the inflammation or lung fibrosis is the result of acute or oxidative lung injury.

In one embodiment, the transcription factor which modulates expression of protective enzymes, which is activated by the administration of the compositions provided herein, which include in another embodiment the whole grain flaxseed or flaxseed lignan complex (FLC), used in the method provided herein, of reducing acute lung inflammation, oxidative lung tissue injury or chronic lung fibrosis in a subject is nuclear factor E2-related factor 2 (Nrf2).

In one embodiment, Nrf2 is a "master" antioxidant transcription factor regulating many endogenous antioxidant enzymes such as hemeoxygenase I in one embodiment, or GST, NQO-1, acetyltransferase, sulfotransferase or their combination in another embodiment. In one embodiment, the transcription factor Nrf2 binds to and activates a specific "antioxidant response element" (ARE) in the promoter region of detoxifying and anti-oxidant enzyme genes. Under homeostatic conditions Nrf2 is bound in one embodiment, by a Keap 1 protein, which in another embodiment, keeps the complex in the cytoplasm; In one embodiment, electrophiles and reactive oxygen species liberate Nrf2 from Keap1 and induce the translocation and accumulation of Nrf2 in the nucleus. Once in the nucleus, binding of nrf2 to the antioxidant response element (ARE) drives the induction of a gene groups that in another embodiment, facilitate the detoxification of carcinogens, or enhance the reducing potential against electrophiles and free radicals, and elevate cellular capacity for repair/removal of oxidatively damaged proteins, or their combination in other embodiments.

In another embodiment, Flaxseed lignans used in the compositions provided herein, for the methods provided herein, act directly or in one embodiment indirectly, on nrf2, inducing its translocation to the nucleus and in one embodiment, activating of the ARE-regulated transcription. In one embodiment nrf2 is required or sufficient in one embodiment, to induce endogenous antioxidant enzyme (AOE) enhancement.

Accordingly, provided herein is a method of reducing acute lung inflammation, oxidative lung tissue injury or chronic lung fibrosis in a subject comprising administering to said subject a composition comprising a whole grain flaxseed, a bioactive ingredient or a metabolite thereof, whereby the bioactive flaxseed component or its metabolite(s) activates a transcription factor which modulates expression of protective enzymes, thereby reducing inflammation and oxidative tissue injury, whereby the protective enzyme is Glutathione —S-transferase, N-acetyl transferase or other Nrf2-modulated enzymes.

In one embodiment, the methods provided herein, are effective in the chemoprevention of cancer, by in another embodiment, modulating the regulation of genes mediated by the Nrf2/ARE pathway, inducing the expression of an endogenous carcinogenic drug metabolizing enzymes. Accordingly, provided herein is a method of chemopreventing cancer in a subject, comprising the step of administering to the subject an effective amount of a flaxseed lignan metabolites, thereby modulating the regulation of genes mediated by the Nrf2/ARE pathway, inducing the expression of an endogenous carcinogenic drug metabolizing enzymes.

Lung cancer is the leading cause of cancer death in both men and women in the U.S., and cigarette smoking is a major etiologic factor. In fact, approximately 85% of lung cancer is caused by smoking. Major lung carcinogens in tobacco smoke are polycyclic aromatic hydrocarbons, typified in one embodiment by benzo[a]pyrene (BaP), and the tobacco-specific nitrosamine 4(methylnitrosamino)-1-(3pyridyl)-1-butanone (NNK). In one embodiment flaxseed, because of its unique nutrient profile has a potential to affect the course of cardiovascular disease and some hormone-responsive cancers such as prostate cancer in one embodiment, or breast cancer in another embodiment. Flaxseed or its bioactive compounds, are effective in another embodiment in lung cancer therapy or chemoprevention due to the activation of the Nrf2/ARE pathway (manuscript in prep) in one embodiment. The Nrf2 transcription factor regulates in one embodiment the expression of Phase II enzymes required for the detoxification of potent carcinogens, by binding in another embodiment, to the antioxidant response element (ARE), a DNA segment located upstream from antioxidant and Phase II carcinogen detoxification enzyme genes. In another embodiment, flaxseed lignans boost endogenous carcinogen detoxification systems in cells in response to a known carcinogen. In another embodiment, the effects of the whole grain flaxseed or flaxseed lignan metabolites used in the compositions disclosed herein; are mediated by modulation of the Nrf2/ARE pathway. In another embodiment, whole grain flaxseed or flaxseed lignan metabolites comprises of the plant lignan precursor, seciosolariciresinol diglucoside (SDG), or the mammalian lignans enterodiol, enterolactone, or a combination thereof are chemopreventive agents in carcinogen-induced lung carcinogenesis. In one embodiment, induction of endogenous drug metabolizing enzymes such as the Phase II Enzymes is a successful strategy for cancer chemoprevention and the hole grain flaxseed or flaxseed lignan metabolites comprises of the plant lignan precursor, seciosolariciresinol diglucoside (SDG), or the mammalian lignans enterodiol, enterolactone, or a combination thereof encompassed in the compositions provided herein, are likely safe and easy to administer candidates in cancer prevention by modulating the regulation of genes mediated by the Nrf2/ARE pathway.

In one embodiment, the whole grain flaxseed or flaxseed lignan metabolites, through the action of the lignans, activate nrf2 inducing in another embodiment, dissociation from Keap1 and nuclear translocation and subsequent binding to the ARE, driving in one embodiment, the transcription of phase II, detoxifying enzymes leading to a more effective chemoprevention using the methods provided herein, with the compositions provided herein, which comprise in another embodiment, the whole grain flaxseed or flaxseed lignan metabolites comprises of the plant lignan precursor, seciosolariciresinol diglucoside (SDG), or the mammalian lignans enterodiol, enterolactone, or a combination thereof. In one embodiment, the cancer treated using the methods for chemoprevention provided herein, is lung cancer, bronchogenic adenocarcinoma or in another embodiment, mesothelioma-related lung cancer. In one embodiment, the endogenous antioxidant and drug detoxifying enzymes leading to a more effective chemoprevention using the methods provided herein, are glutathione S-transferase (GST), NAD(P)H:quinone oxidoreductase1 (NQO-1), epoxide hydrolase, glutamylcysteine synthetase, UDP:glucuronosyl transferases other Phase II metabolizing enzymes or a combination thereof.

Accordingly and in one embodiment, provided herein is a method of treating lung cancer in a subject, comprising increasing dietary intake of flaxseed lignan metabolites by the subject, thereby inhibiting proteasome activity. In another embodiment, provided herein is a method of treating lung cancer in a subject, comprising increasing dietary intake of flaxseed lignan metabolites by the subject, thereby inhibiting tumor growth. In another embodiment, the ubiquitin-proteasome pathway plays a critical role in the degradation of cellular proteins and cell cycle control. In another embodiment, mitotic processes are strictly regulated by cyclins and cyclin-dependent kinases which in turn are important substrates of the proteasomal degradation pathway. Inhibitors of proteasomal activity induce in another embodiment apoptosis in tumor cells and in another embodiment, are useful as anticancer agents, alone or in combination with other drugs. In one embodiment, the method of treating lung cancer in a subject, comprising increasing dietary intake of flaxseed lignan metabolites by the subject, thereby inhibiting proteasome activity and tumor growth comprises inhibiting proteasomal activity.

In another embodiment, the method of treating lung cancer in a subject, comprising increasing dietary intake of flaxseed lignan metabolites by the subject, thereby inhibiting proteasome activity and tumor growth, further comprising administering to the subject another proteasome inhibitor, such as Velcade (PS-341) and PS-519, proteasome inhibitory (+)-lactacystin β-lactone analogs, (Benzyloxycarbonyl)-Leu-Leu-phenylalaninal, Z-LLL-CHO, 2,3,5a,6-Tetrahydro-6-hydroxy-3(hydroxymethyl)-2, Lovastatin, methyl-10H-3a,10a-epidithio-pyrazinol[1,2 .alpha.]indole-1,4-dione, 4-Hydroxy-3-nitrophenylacetyl-Leu-Leu-Leu-vinyl 426104.alpha.-Meth-yl-sulfone clasto-Lactacystin .beta.-Lactone, 4-Hydroxy-5-iodo-3-nitrophenylacetyl-Leu-Leu-☐-Methyl-omuralide Leu-vinylsulfone, Ac-hFLFL-epoxide, Mevinolin, Aclacinomycin A, Streptomyces galilaeus, MG 101, Aclarubicin, MG-115, ACM, MG-132, AdaAhx3L3VS, MG-132 in Solution, AdaK(Bio)AhX3L3VS, MG-262, AdaLys(Bio)Ahx3L3, MK-803, Adamantane-acetyl-(6-aminohexanoyl), NIP-L3VS 3-(leucunyl)-3-vinyl-(methyl)-sulfone, ALLM, NLVS, ALLN, NP-L3VS, Calpain Inhibitor I, NP-LLL-VS, Calpain Inhibitor II, Omuralide, Carbobenzoxy-L-leucyl-L-leucyl-L-leucinal, PR-11, Carbobenzoxy-L-leucyl-L-leucyl-L-norvalinal, PR-39, Gliotoxin, Gladiocladium fimbriatum, Isovaleryl-L-tyrosyl-L-valyl-DL-tyrosinal, Lactacystin, Synthetic, clasto-Lactacystin β-Lactone, Z-LL-Nva-CHO, Ubiquitin Aldehyde, YU101, Ro106-9920, Z-GPFL-CHO, Ro106-9920 Tyropeptin A, and the like.

In one embodiment, the invention provides the compositions described herein above in the methods provided herein. Accordingly and in another embodiment, provided herein is a composition for modulating the Nrf2/ARE pathway in a subject, comprising flaxseed lignan complex metabolites, whereby Flaxseed lignans ED/EL are shown to act directly (or indirectly) on nrf2, thus, inducing its translocation to the nucleus and activation of the ARE-regulated transcription. In Aim 1, we will investigate if nrf2 is required and/or sufficient to induce endogenous AOE enhancement. In another embodiment, the flaxseed lignans used in the compositions and methods provided herein, are enterodiol, enterolactone, seciosolariciresinol diglucoside (SDG), or a combination thereof.

In another embodiment, any embodiment of a composition described in the methods provided herein, is encompassed in the compositions of the invention.

The term "subject" refers in one embodiment to a mammal including a human in need of therapy for, or susceptible to, a condition or its sequalae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Example 1

Delivery of Endothelial antioxidant Enzymes can prevent Lung Transplant Injury

Figure 2:
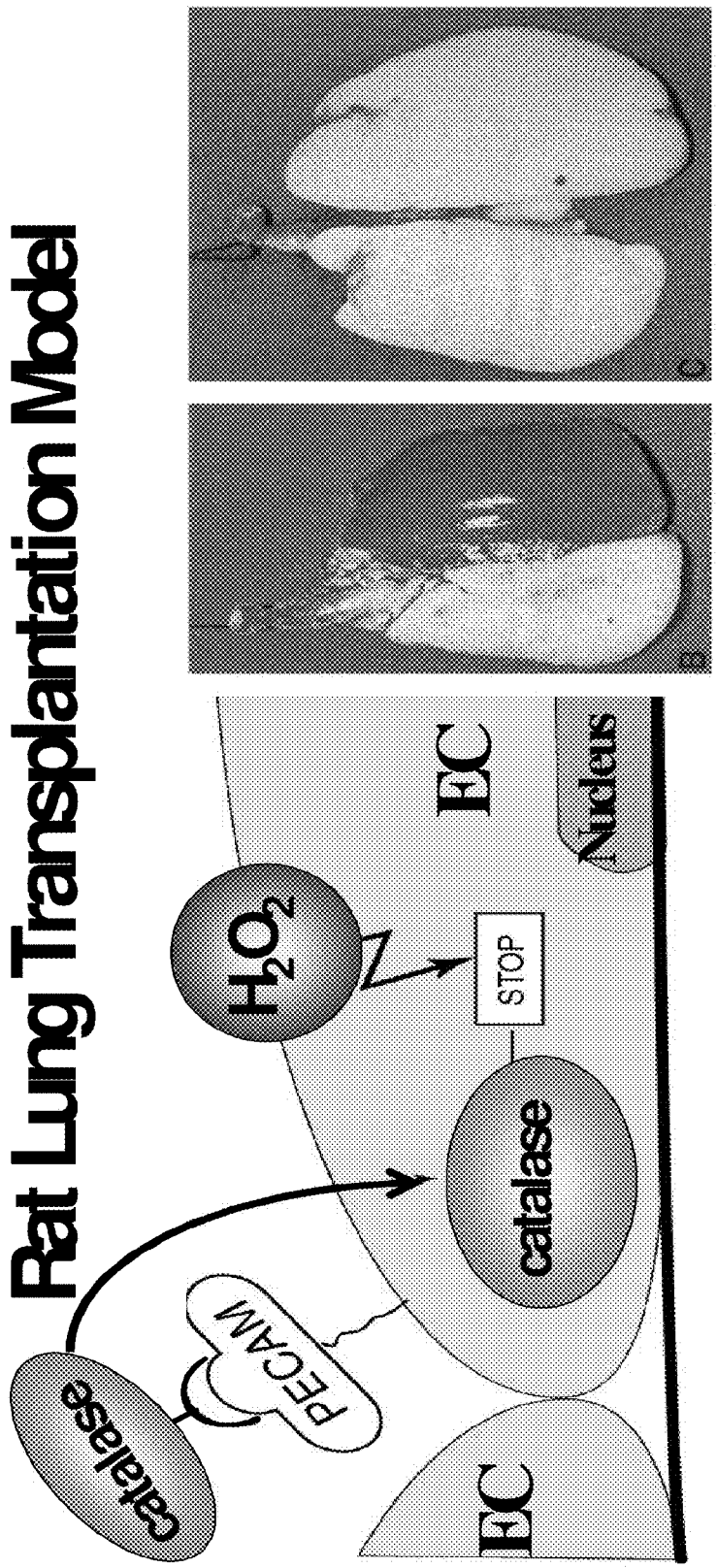
FIG. 2: shows a) schematic representation of ROS detoxification by immunotargeting of catalase in the vessel lumen; b) severe injury of left lung transplant after cold ischemia; and c) protection by anti-PECAM/catalase; taken from: Kozower, B. D., M. Christofidou-Solomidou, T. D. Sweitzer, S. Muro, D. G. Buerk, C. C. Solomides, S. M. Albelda, G. A. Patterson, and V. R. Muzykantov. 2003. Immunotargeting of catalase to the pulmonary endothelium alleviates oxidative stress and reduces acute lung transplantation injury. *Nat Biotechnol* 21:392-398.

Using a rodent model of lung transplantation, targeted antioxidant enzyme delivery to the pulmonary endothelium, were investigated and antioxidant treatment of the pulmonary endothelium by vascular immunotargeting of catalase were shown to alleviates oxidative stress and reduces acute lung transplantation injury—see FIG. 2. This strategy, has established that alleviation of endothelial oxidative stress is sufficient to confer significant tissue protection in IRI.

These findings validate the therapeutic potential of boosting vascular antioxidant defense as a novel strategy to reduce tissue injury with lung transplantation. Potential applications of this strategy include improving the outcome of clinical lung transplantation and a wide variety of endothelial disorders. Provided herein is a non-toxic, safe dietary agents that act by boosting the intracellular, endogenous antioxidant defense and prevent endothelial ROS generation in the lung.

Example 2

Flaxseed and its By-products as Bioactive, Therapeutic Dietary Supplements

Flax is an annual plant that thrives in deep moist soils rich in sand, silt, and clay. The seeds in the flax plant are filled with flaxseed oil, sometimes called linseed oil. Flaxseeds are known as *Linum usitatissimum* with the species name meaning "most useful". The flax plant originated in Mesopotamia and first records of the culinary use of flaxseeds is from times of ancient Greece. Flaxseed was first planted in the US with the arrival of the early colonists in North. In the 17th century, flax was first introduced and planted in Canada, the country that is currently the major producer.

Figure 3:
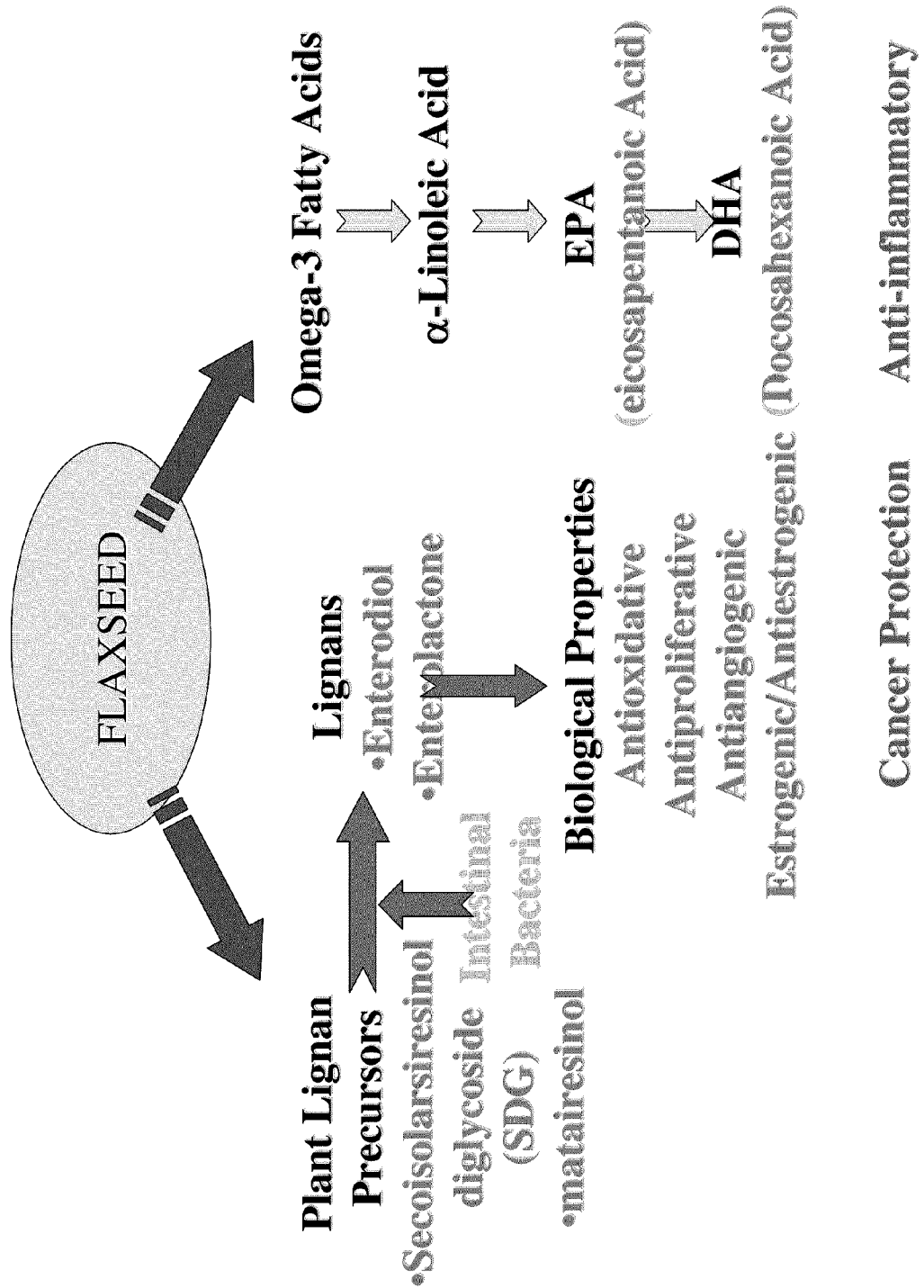
FIG. 3: shows a schematic of the various components of flaxseed; Lignans and Omega-3 Fatty acids.

Flax products are made from the seeds found inside the fruits. The seeds contain a fatty oil called alpha-linolenic acid (ALA), an essential fatty acid and linoleic acid (see FIG. 3). Essential fatty acids (EFA's) are the primary nutritional component of flax seed. The two key EFA's are Linoleic and linolenic. Flax seed oil has a high amount of these two EFA's, and therein lies the reason for the oils' demand. ALA is a precursor of eicosapentaenoic acid (EPA) and docosahexaenoic acid (DHA), which belong to omega-3 fatty acids. While EPA and DHA are found primarily in fish, ALA is mostly found in flaxseed oil and other vegetable oils. Omega-3 fatty acids help reduce inflammation and most omega-6 fatty acids tend to promote inflammation. Studies suggest that flaxseed oil and other omega-3 fatty acids may be helpful in treating a variety of inflammatory conditions, such autoimmune diseases. For example, systemic lupus erythematosus (SLE).

Dietary flaxseed has provided significant benefits in animal models of lupus nephritis and in patients with this condition, and carbon tetrachloride-induced hepatic injury. The evidence for the use of flaxseed oil is strongest for heart disease and problems that contribute to heart disease. Flaxseed (as opposed to flaxseed oil) is also a good source of phytoestrogens.

In addition to omega-3 fatty acids, flaxseed products also contain potentially therapeutic chemicals called lignans. Lignans are widely occurring plant compounds and are closely related to lignin, which forms the woody component of trees and other plants. The lignans are characterized by their dimeric composition from cinnamic acids, and they are attracting increasing attention as a result of their pharmacological properties. Lignans are believed to have direct antioxidant properties and can inhibit lipid peroxidation in tissues such as the brain.

Figure 4:
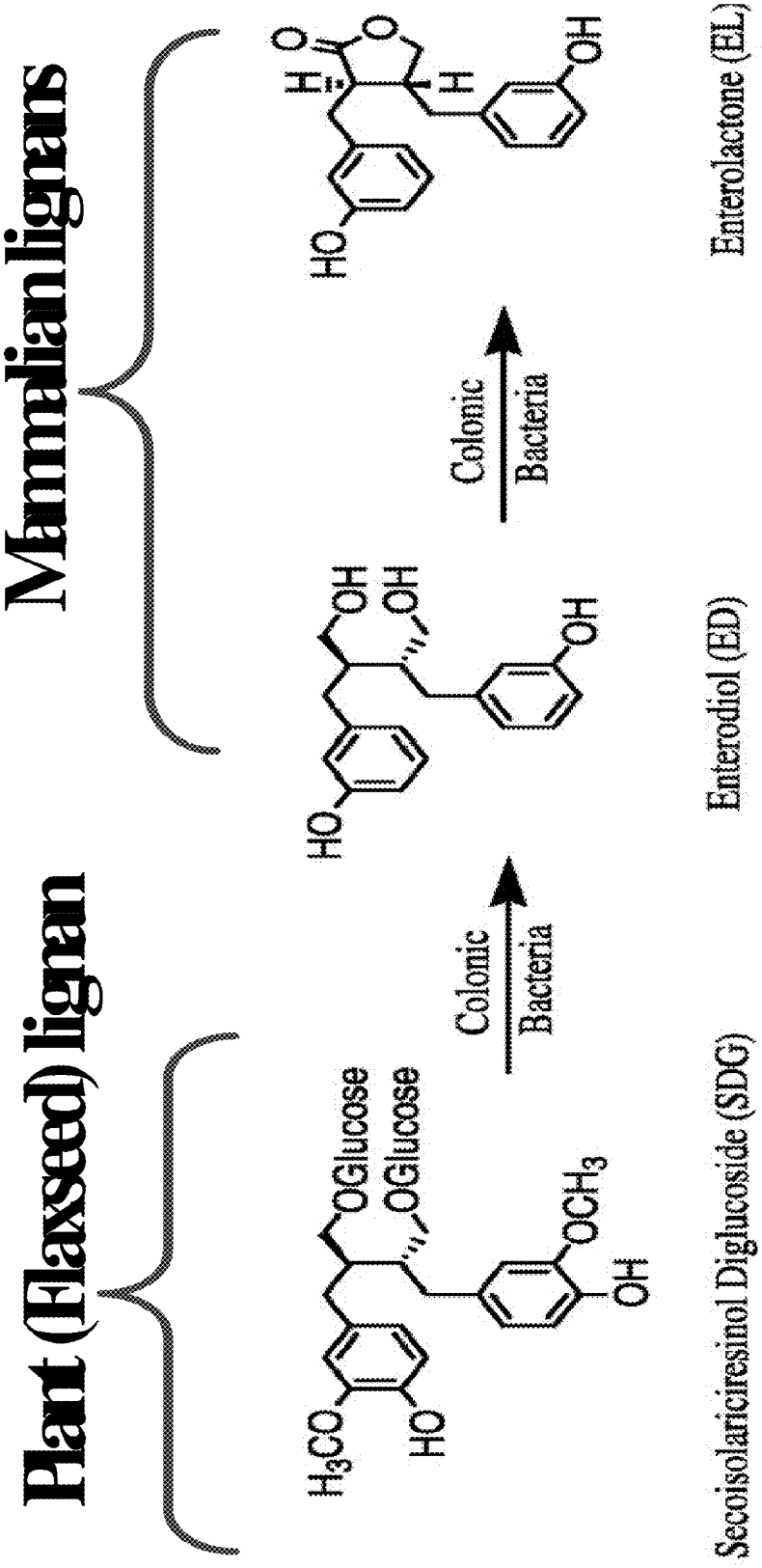
FIG. 4: shows how Secoisolariciresinol diglucoside (SDG), an antioxidant isolated from flaxseed, is metabolized in the human intestine to enterodiol (ED), and enterolactone (EL).

Secoisolariciresinol diglucoside (SDG), an antioxidant isolated from flaxseed, is metabolized in the human intestine to enterodiol (ED), and enterolactone (EL) (see FIG. 4). It will be important for future experiments to note that SDG is not directly taken up by cells, unlike ED and EL. The ex vivo antioxidant activities of these three lignans (SDG, EL and ED) were shown by specifically inhibiting linoleic acid lipid peroxidation, indicating direct hydroxyl radical scavenging activity. In addition, due to their ability to inhibit platelet activating factor (PAF), lignans may exert antioxidant activity by inhibiting ROS production by white blood cells. When tested therapeutically in streptozotosin-induced Diabetes mellitus, a condition associated with both ROS generation and PMN activation, SDG-treated animals resulted in prevention of diabetes, decrease in serum and pancreatic lipid peroxidation as well as a decrease in WBC-derived ROS. In addition, the antioxidant reserve of the pancreas was significantly increased. It has been shown that dietary flaxseed supplementation, decreased carbon tetrachloride-induced oxidant stress and lipid peroxidation levels in blood and red blood cell membranes in rats.

Example 3

Lignans Modulate the Production of Antioxidant Enzymes (AOEs)

In addition to their direct antioxidant activities (described in the examples above), some lignans have also been shown to upregulate endogenous antioxidant defenses such as the Phase I and Phase II enzymes which are first lines of defense against xenobiotics and more specifically act against dietary and environmental carcinogens that enter the body. The Phase I enzymes identify pre-carcinogenic compounds (xenobiotics) and make them more reactive, more water-soluble and easier for the body to dispose of (often via the action of is Phase II enzymes). Phase I enzymes consist of CYPp450 family of cytochromes. Proteins belonging to this class of enzyme catalyze reactions resulting in the addition of functional groups and reactive centers e.g. SH, OH, —NH2 and —COOH groups to their substrates. Enzymes involved in the Phase II or the detoxification process e.g. Glutathione —S-transferase, and the N-acetyl transferases are responsible for the deactivation of radicals and electrophiles known to intervene in normal cellular processes, prior to their excretion.

The lignan sesamin (derived from sesame seeds), has been shown to stimulate the production of glutathione S-transferase (GST). GST is a "Phase II" detoxifying enzyme that catalyzes the reaction of glutathione with electrophiles to form compounds that are less toxic, more water-soluble, and can be excreted easily. The in vivo antioxidant action of a lignan-enriched extract from fruits was further evidenced by enhancement in hepatic mitochondrial glutathione antioxidant status, as evidenced by increases in reduced glutathione levels and increased activities of glutathione reductase (GR), glutathione peroxidase (GPx), as well as glutathione S-transferases. Sesame-derived lignans (sesamin and episesamin) were shown to decrease exercise-dependent lipid peroxidation in mice and enhance the enzymatic activity of both GST and GPx thus conferring protection. Yu et al [Ikeda, T., Y. Nishijima, H. Shibata, Y. Kiso, K. Ohnuki, T. Fushiki, and T. Moritani. 2003. Protective effect of sesamin administration on exercise-induced lipid peroxidation. *Int J Sports Med* 24:530-534.], isolated eleven lignans from the bark of a plant which were shown to have hepatoprotective properties by significantly preserving the levels and the activities of glutathione, and the AOEs, superoxide dismutase, glutathione peroxidase and catalase as well as ameliorated lipid peroxidation as demonstrated by a reduction of MDA production. Glutathione, superoxide dismutase (SOD) and glutathione peroxidase all play important roles in the cellular defense against oxidative stress. Prasad and coworkers [Prasad, K., S. V. Mantha, A. D. Muir, and N. D. Westcott. 1998. Reduction of hypercholesterolemic atherosclerosis by CDC-flaxseed with very low alpha-linolenic acid. *Atherosclerosis* 136:367-375, Pattanaik, U., and K. Prasad. 1998. Oxygen Free Radicals and Endotoxic Shock: Effect of Flaxseed. *J Cardiovasc Pharmacol Ther* 3:305-318], investigated cardiac dysfunction and tissue injury during endotoxemia in dogs placed on flaxseed diets, a condition related to increased levels of oxygen free radicals. They measured, among other, antioxidant enzyme activity (superoxide dismutase, catalase, glutathione peroxidase), as well as cardiac malondialdehyde (MDA) concentration which is a lipid peroxidation product. They concluded that pretreatment up to 6 days with flaxseed attenuated the endotoxin-induced cardiac dysfunction and cellular damage. Example 1, showed for the first time that dietary flaxseed and more specifically flaxseed lignans, have potent anti-inflammatory and antioxidant effects in lung tissues in murine models of oxidative acute lung injury.

Although the antioxidant properties of flaxseed have been recognized, the molecular mechanism(s) of antioxidant protection by flaxseed or its individual bioactive ingredients lignans has not been carefully explored.

Example 4

The Nrf2/ARE Signaling Pathway

Figure 5:
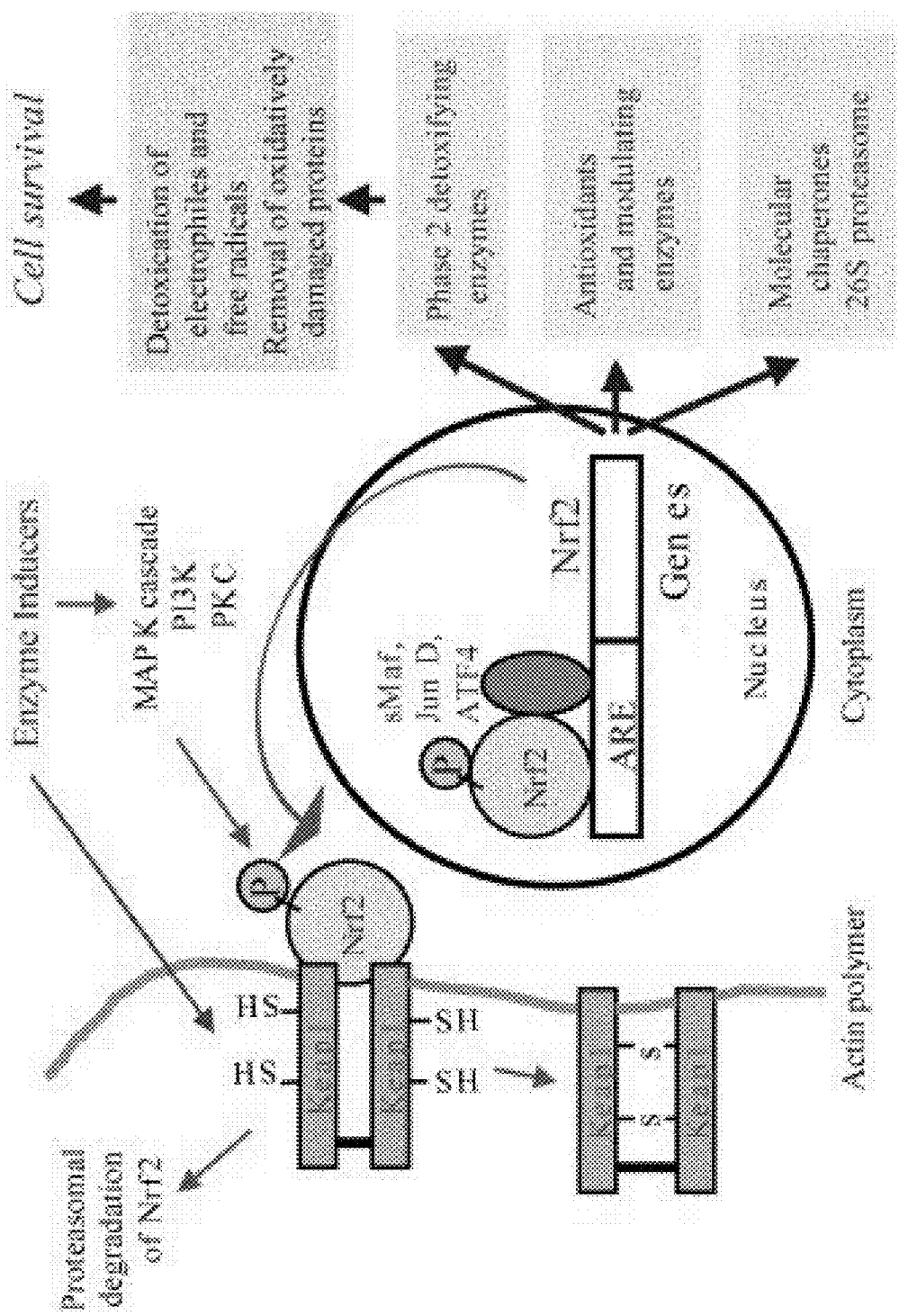
FIG. 5: shows a schematic of the Nrf2/ARE signaling pathway taken from Wakabayashi, N., Itoh, K., Wakabayashi, J., Motohashi, H., Noda, S., Takahashi, S., Imakado, S., Kotsuji, T., Otsuka, F., Roop, D. R., Harada, T., Engel, J. D., and Yamamoto, M. (2003). Keap1-null mutation leads to postnatal lethality due to constitutive Nrf2 activation. Nat Genet. 35, 238-245.

Many endogenous antioxidant enzymes such as hemeoxygenase I (including most of the Phase II enzymes such as GST, NQO-1, acetyltransferase, sulfotransferase) are regulated by a "master" antioxidant transcription factor called Nrf2, in much the same way that many inflammatory proteins and cytokines are regulated by the master transcription factor NF-KB (see FIG. 5). The transcription factor Nrf2 binds to and activates a specific "antioxidant response element" (ARE) in the promoter region of many detoxifying and anti-oxidant enzyme genes. Its regulation is similar to that of NF-κB. Under homeostatic conditions Nrf2 is bound by a protein called Keap1 that keeps the complex in the cytoplasm; Keap1 thus being a negative regulator of Nrf2. Electrophiles and reactive oxygen species liberate Nrf2 from Keap1 and induce the translocation and accumulation of Nrf2 in the nucleus (FIG. 5). Once in the nucleus, binding of nrf2 to the antioxidant response element (ARE) drives the induction of a gene groups that may facilitate the detoxification of carcinogens, enhance the reducing potential against electrophiles and free radicals, and elevate cellular capacity for repair/removal of oxidatively damaged proteins—see FIG. 5.

Flaxseed lignans are shown to act directly (or indirectly) on nrf2, thus, inducing its translocation to the nucleus and activation of the ARE-regulated transcription. In Aim 1, we will investigate if nrf2 is required and/or sufficient to induce endogenous AOE enhancement.

Example 5

Flaxseed Supplementation Ameliorates Inflammation and Acute Lung Injury (ALI)

Figure 6:
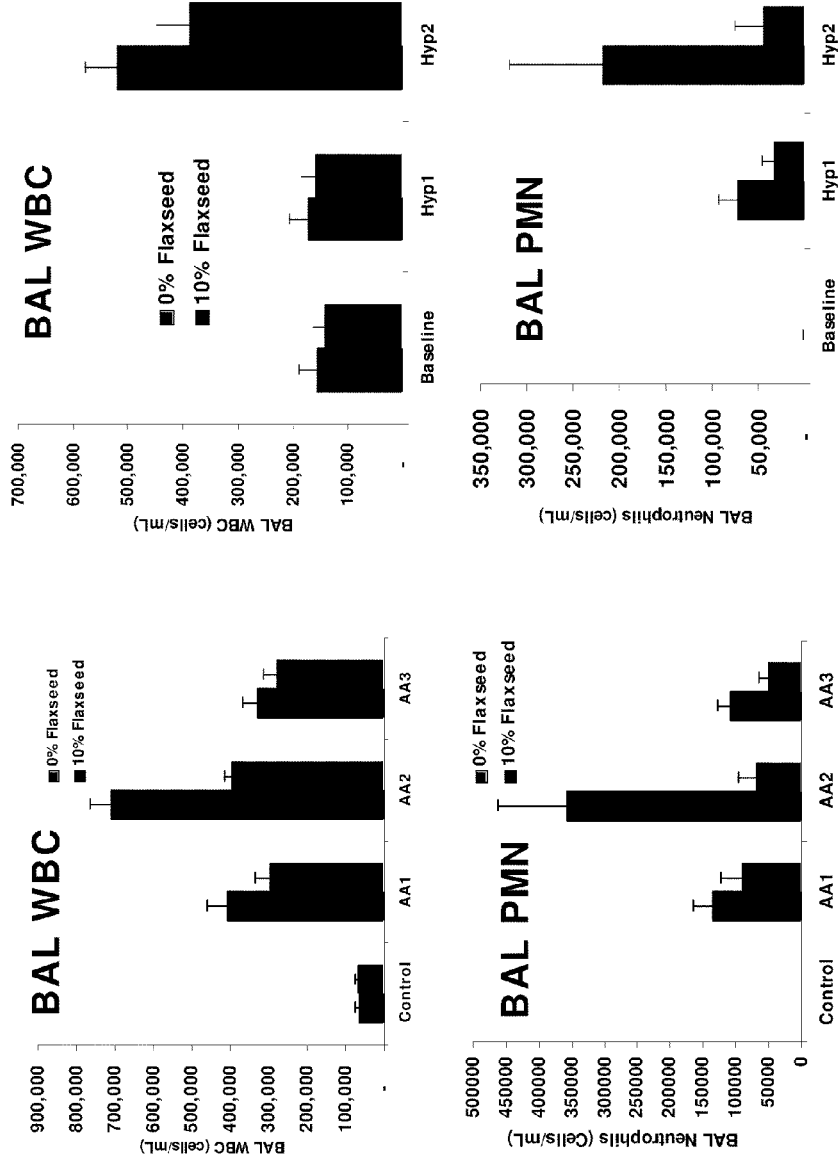
FIG. 6: shows the ability of whole grain dietary flaxseed (10%) to reduce lung injury in two models: acid aspiration-induced lung injury (24 hours), simulating oxidative lung injury resulting from aspiration of gastric contents, and an acute model of hyperoxia-induced ALI (80% O2 for 6 days).
Figure 7:
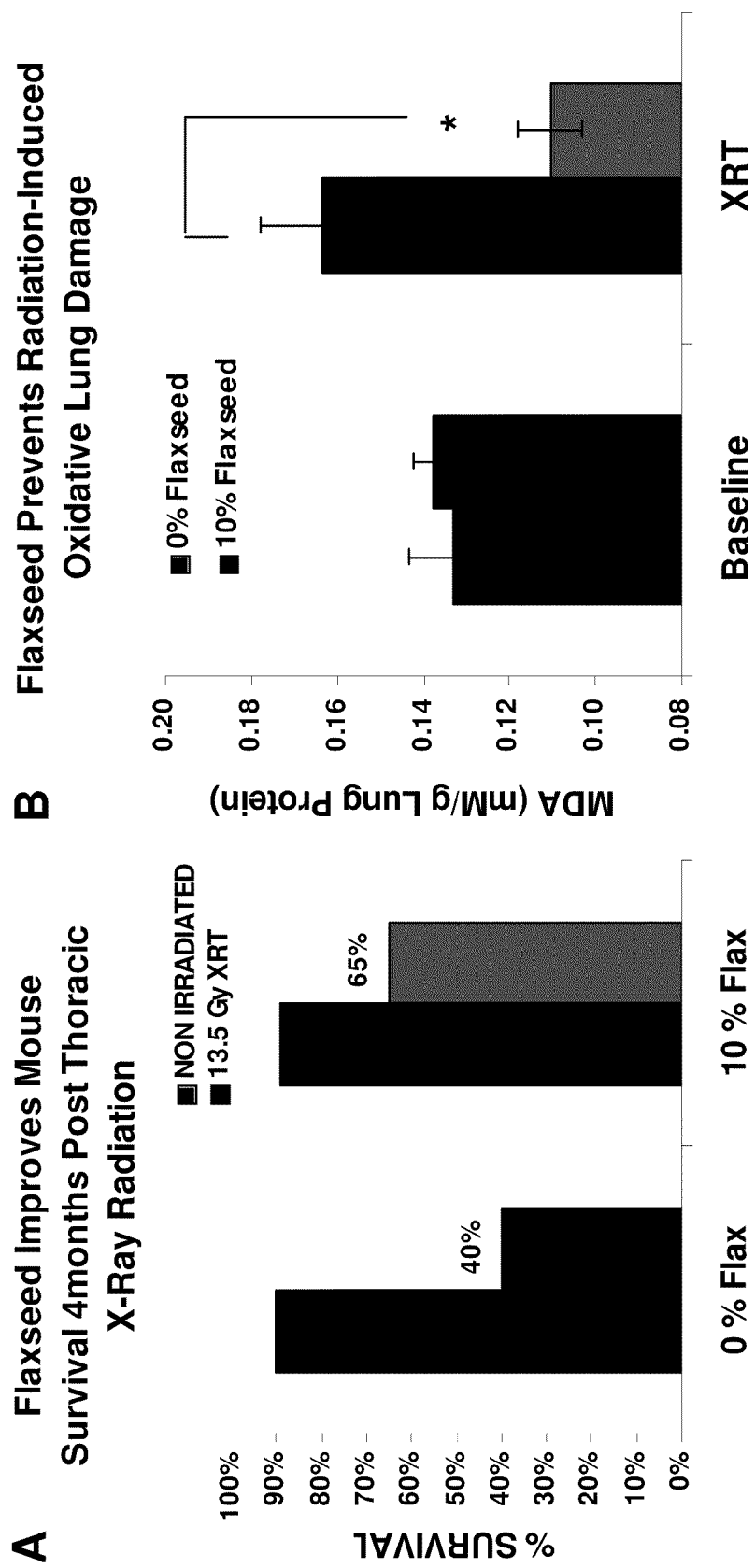
FIG. 7: shows a) three weeks of dietary flaxseed supplementation prior to the time of thoracic irradiation, leads to significantly increased mouse survival as compared to irradiated is mice fed a standard, control diet; and b) Mouse weight, reflecting the animals' overall health and tolerability of the diet (3 weeks pre- and 4 months post-XRT), indicated that flaxseed-supplemented mice had gained weight and had an overall better health profile than control mice.

The ability of flaxseed to reduce lung injury was tested in two models: acid aspiration-induced lung injury (24 hours), simulating oxidative lung injury resulting from aspiration of to gastric contents, and an acute model of hyperoxia-induced ALI (80% O2 for 6 days). Mice were placed on a 10% flaxseed diet for 3 weeks (to ensure a steady state), versus a specially designed isocaloric basic diet. Results are shown in FIG. 6. Experiments were repeated twice for hyperoxia (Hyp1 and Hyp2) and three times for Acid Aspiration (AA1, AA2 and AA3). Bronchoalveolar lavage (BAL) was evaluated for A) white blood cells (WBC) and b) neutrophils (PMN), 24 h post intratracheal challenge of hydrochloric acid, or after 6 d of hyperoxia. Following hyperoxia and acid aspiration, FS-supplemented mice had a significant decrease in BAL neutrophils while overall alveolar WBC influx tended to be lower. In summary, dietary FS decreased lung inflammation and injury in models of ALI, suggesting a protective role against pro-oxidant-induced ALI in vivo.

Example 6

Dietary Whole Grain Flaxseed (10%) is Highly Effective in a Murine Orthotopic Model of Bronchogenic Adenocarcinoma of the Lung A transgenic mouse was used, which allows regulated expression of one copy of a mutated K-ras gene. The protein from the mutated gene is normally not expressed because the coding region is preceded by stop codon. However, this stop codon is flanked by two lox recombination sites. Thus, when the animals are injected intratracheally with an adenovirus expressing cre recombinase (Ad.Cre), the epithelial cells that take up the transgene excise the stop codon and begin to express the mutated Kras. This oncogene then induces the formation of malignant lung lesions. The lesions start as adenomatous hyperplasia, but soon progress to frank adenocarcinomas as shown by the histological evaluation. Depending on the dose of Ad.Cre, the number lesions and the extent of tumor can be controlled. In this model, using $10^9$ pfu of Ad.Cre, detectable tumors are obtained at 14-21 days and death by about 45 days.

The Kras model of lung bronchoalveolar carcinoma was used to test whether dietary flaxseed blocked tumor growth. Mice were injected intratracheally with 5×109 Ad.Cre virus particles to initiate tumor formation and diet was initiated (0% vs. 10% Flaxseed) on the same day (n=20 per diet). Three (3) mice from each diet (Mouse 1-3 from 10% Flaxseed and mouse 21-23 from the 0% flaxseed diet) were sacrificed a month post tumor initiation for histopathological assessment. Hisatological evaluation indicated a clear protection by the flaxseed diet which was confirmed by measurements of tumor area using image analysis software (57% tumor vs. 13% for 0% vs. 10% flax, respectively). See FIG. 26.

These data provide clear evidence that flaxseed is protective in in lung cancer. No toxicity was noted at the dose tested.

Example 7

Figure 8:
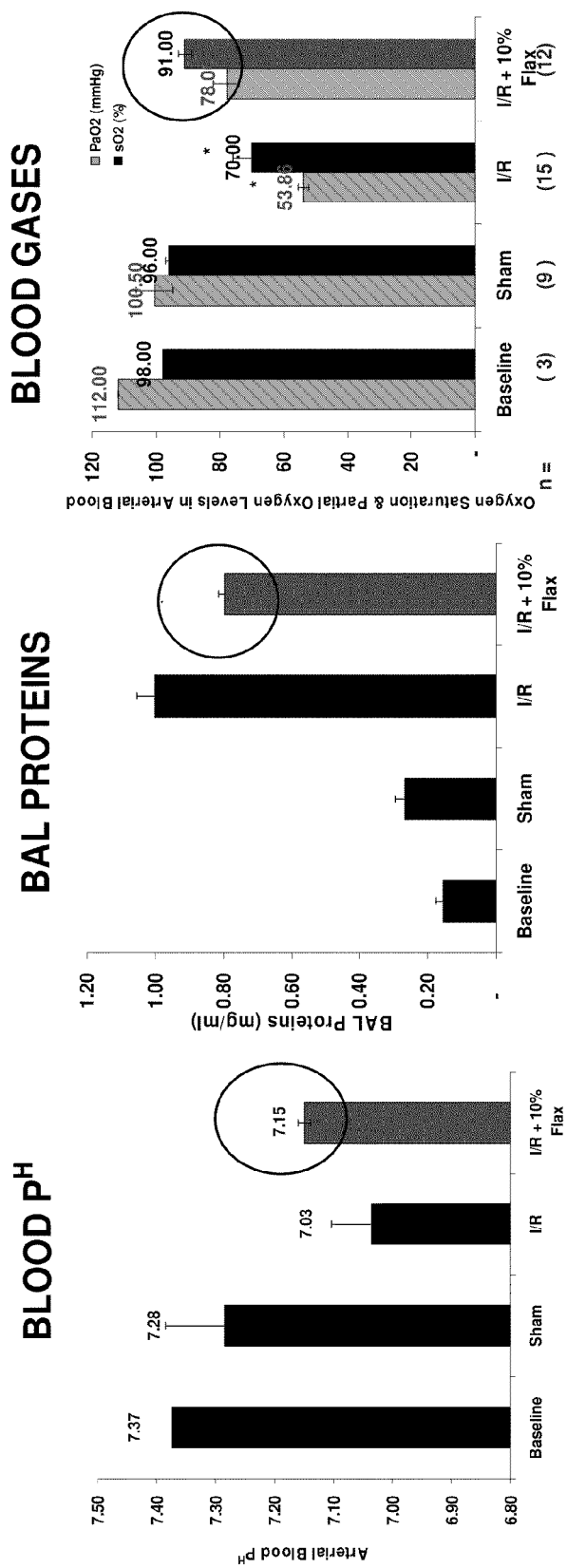
FIG. 8: shows the effects of high FS diet in a murine model of ALI induced by ischemia/reperfusion I/R). Sham animals (undergoing thoracotomy, but not I/R) were used as controls. I/R injury was evaluated using five parameters (FIG. 8-10): (1) physiologic arterial blood gases (ABG), (2) morphologic (histology) (3) biologic (bronchoalveolar lavage, BAL), (4) immunohistochemical and (5) biochemical (Malondialdehyde detection-MDA assay for lipid peroxidation).
Figure 22:
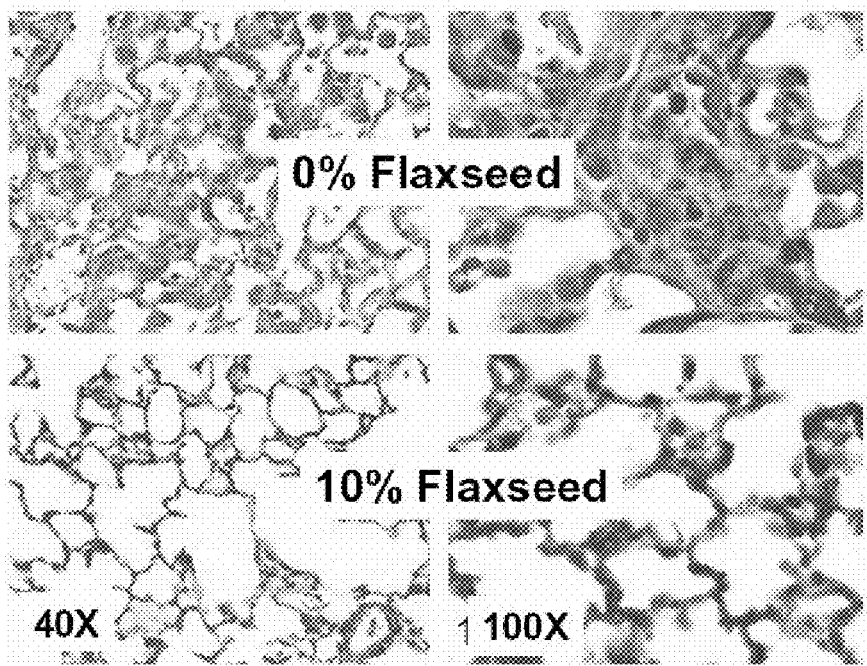
FIG. 22: shows how whole grain dietary flaxseed (10%) prevents lung fibrosis resulting from Xray radiation treatment (XRT) of mouse lung. Blue color indicates collagen deposition (resulting in lung stiffness and ultimately, death). Less collagen is seen with Flaxseed supplementation (bottom panels).
Figure 23:
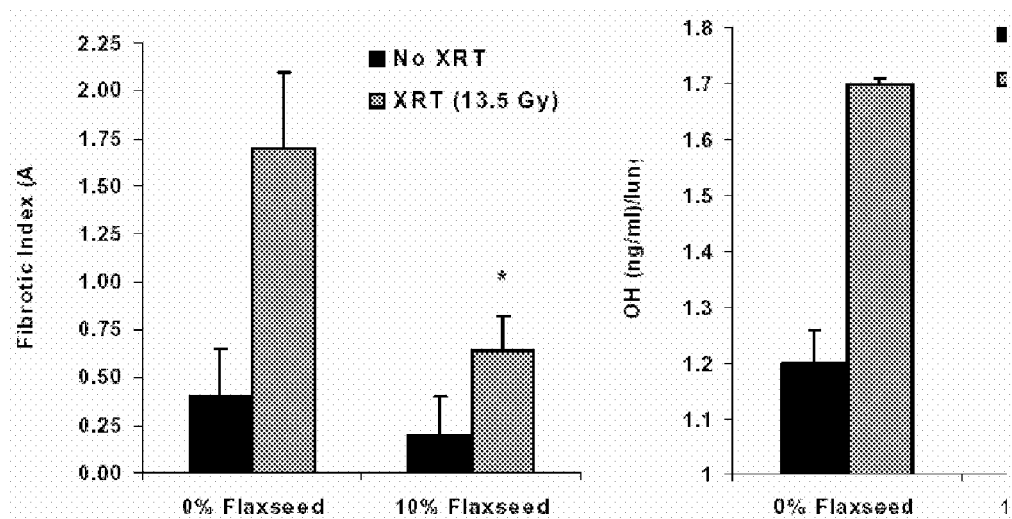
FIG. 23: shows semiquantitative (left) and quantitative (right) assessment of lung fibrosis taken from histological assessment of lung sections or whole lung homogenates respectively.
Figure 24:
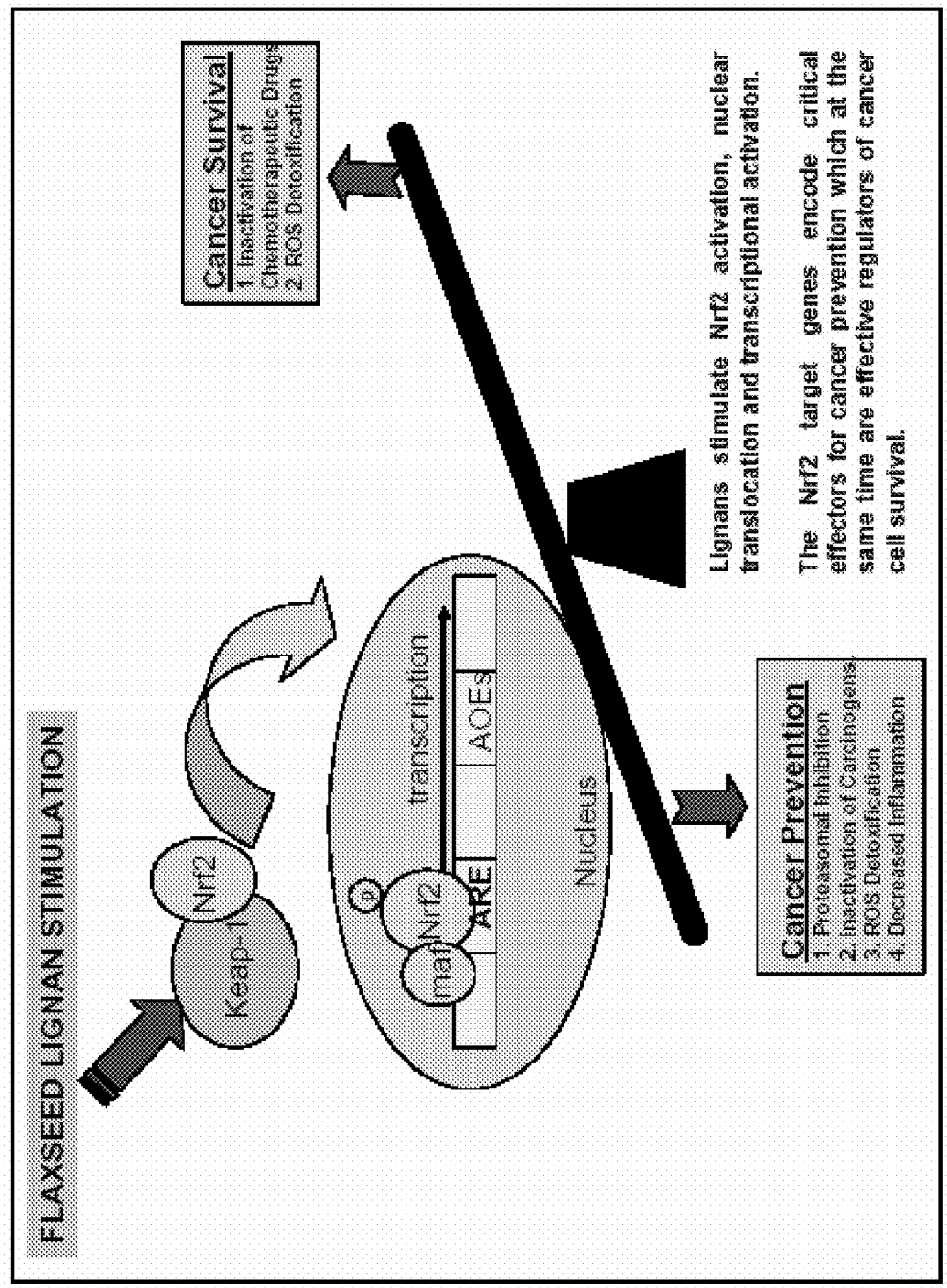
FIG. 24: shows a schematic of anticarcinogenic effects of lignans: Flaxseed, via the action of the lignans, modulates the tumor microenvironment and thus affects tumor growth and metastasis.

Dietary Flaxseed Alleviates Thoracic X-ray Radiation (XRT)-induced Oxidative Lung Injury and Improves Survival in a Murine Model Another model of lung ROS injury is lung irradiation. The effectiveness of radiotherapy for intrathoracic malignancies is greatly limited by the radiation tolerance of normal structures. In particular, the lung is especially sensitive to the damaging effects of irradiation. It is now accepted that DNA damage is the primary mechanism by which radiation causes cell injury and death and that most of this damage to DNA is produced indirectly, by ionizing other molecules (e.g. water) to produce free radicals that then react with the DNA. The radiohydrolysis of water molecules gives rise to extremely damaging ROS. Oxidative modification of proteins by formation of Nitrotyrosine and of lipids has been reported, although the molecular pathways from the oxidative tissue insult to late fibrosis are unclear. Lipid peroxides generated as a result of thoracic XRT, can undergo further decomposition to give products like malondialdehyde (MDA) that can be detected by sensitive assays. A 10% flaxseed-supplemented diet was evaluated in a mouse thoracic XRT model with respect to lipid peroxidation (MDA formation) over time: Three weeks of dietary flaxseed supplementation prior to the time of thoracic irradiation, led to significantly increased mouse survival as compared to irradiated mice fed a standard, control diet (FIG. 8A). Mouse weight, reflecting the animals' overall health and tolerability of the diet (3 weeks pre- and 4 months post-XRT), indicated that flaxseed-supplemented mice had gained weight and had an overall better health profile than control mice. A significantly decreased oxidative modification of irradiated lungs was observed 4 months post-radiation, as measured by MDA (FIG. 8B). FIG. 22 indicates histological evaluation of lung fibrosis and FIG. 25, quantitative analysis of lung collagen levels confirming findings that indicate a clear protective role of Flaxseed.

These data provide further evidence that dietary supplementation of flaxseed has therapeutic applications in ameliorating tissue oxidant stress. In addition, prolonged supplementation (4 months) is well tolerated and improves overall animal health.

Example 8

Flaxseed Supplementation Ameliorates Lung Ischemia Reperfusion Injury in Mice

Next whether flaxseed diets in a mouse model that are directly induced lung ischemia-reperfusion injury, was tested in a manner more similar to what might be seen in to transplantation. The effects of high FS diet was tested in a murine model of ALI induced by ischemia/reperfusion (I/R). Mice were thus anesthetized; tracheotomy and mechanical ventilation was performed ($FIO_2$ 21%, TV 10 ml/kg, RR 130/min). Thoracotomy was performed and the left pulmonary hilum clamped for 60 minutes. The clamp was then removed and reperfusion allowed for an additional 60 minutes. Sham animals (undergoing thoracotomy, but not I/R) were used as controls. I/R injury was evaluated using five parameters (FIG. 8-10): (1) physiologic arterial blood gases (ABG), (2) morphologic (histology) (3) biologic (bronchoalveolar lavage, BAL), (4) immunohistochemical and (5) biochemical (Malondialdehyde detection-MDA assay for lipid peroxidation).

Mice were fed specially formulated FS diets (0% or 10%) for several weeks and were then subjected to IRI. Sham animals had normal arterial $PaO_2$, arterial saturation, BAL protein (FIG. 8) and histology (FIG. 9) compared to untreated mice. Mice fed 0% FS had a significant decrease in arterial $PaO_2$ and saturation compared to sham (54±2 vs 101±11 $PaO_2$, 70±4 vs 95±2 saturation), a significant increase in BAL protein (1.0±0.05 vs 0.27±0.03) and marked perivascular and alveolar edema, intra-alveolar hemorrhage and WBC accumulation compared to sham.

Figure 10:
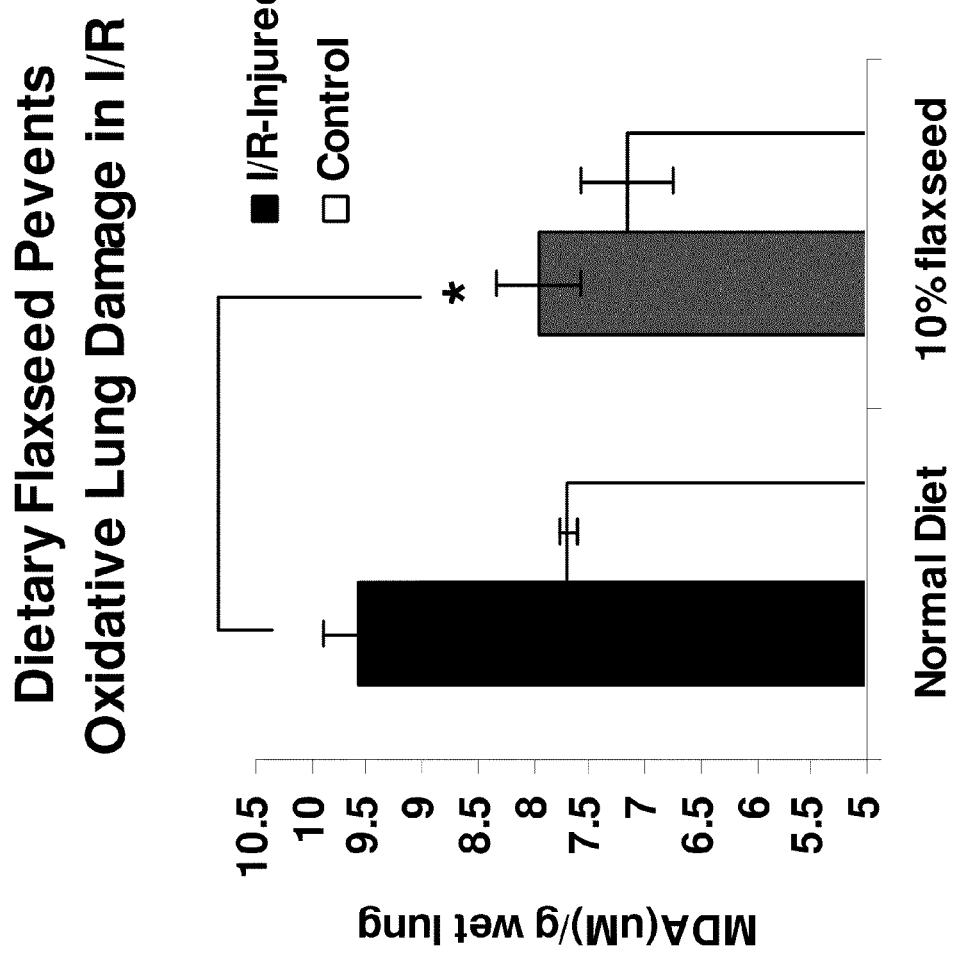
FIG. 10: shows directly measured MDA levels.

Remarkably, mice fed 10% FS had significant improvement in arterial $PaO_2$ and saturation compared to 0% FS (81±4 vs 54±2 $PaO_2$, 91±2 vs 70±4 saturation), a significant decrease in lung BAL protein (0.8±0.04 vs 1.0±0.05) (FIG. 10) and no histological features of I/R injury compared to 0% FS. (n>6, all groups blinded) (FIG. 10—H&E histology).

Figure 9:
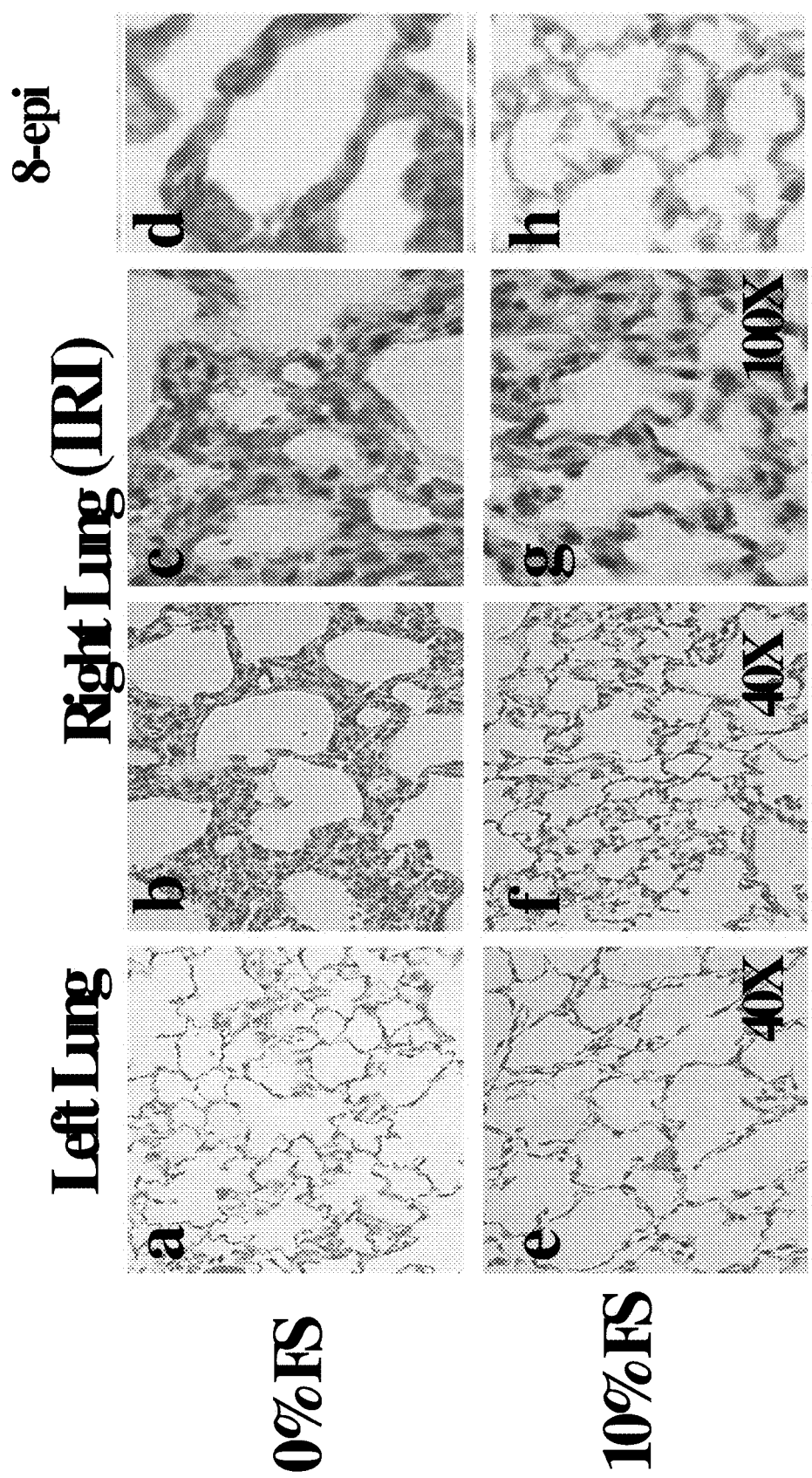
FIG. 9: shows the histological effects of high FS diet in a murine model of ALI induced by ischemia/reperfusion (I/R). Sham animals (undergoing thoracotomy, but not I/R) were used as controls.

To evaluate the extent of oxidative injury and identify products of tissue oxidation, IRI lungs were stained with an antibody directed against $iPF_{2\alpha}$-III (an $F_2$ isoprostane reflecting lipid peroxidation—(anti-8epi antibody). Lipid peroxidation was significantly blunted in Flaxseed-fed animals following IRI as shown by the decreased blue staining (FIG. 9-h vs. d). MDA levels were measured directly as shown in FIG. 10. The flaxseed diet significantly reduced the levels of MDA after IRI.

This data shows that dietary FS is clearly protective against I/R injury in a murine model of ALI, as demonstrated by an improvement in physiologic, histological and biologic parameters.

Example 9

Figure 11:
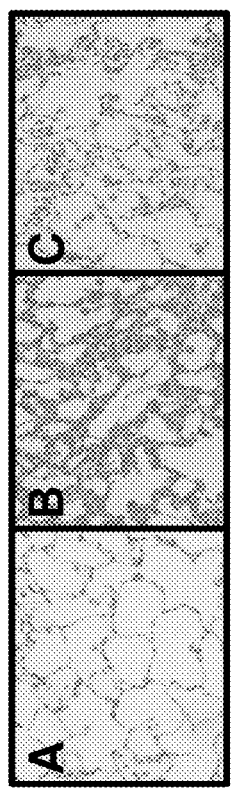
FIG. 11: shows Flaxseed-treated rats showed decreased lung inflammation and interstitial edema (C) associated with the procedure (orthotopic lung transplantation) as compared to rats fed a normal chow (B) while (A) is an untreated control lung.
Figure 12:
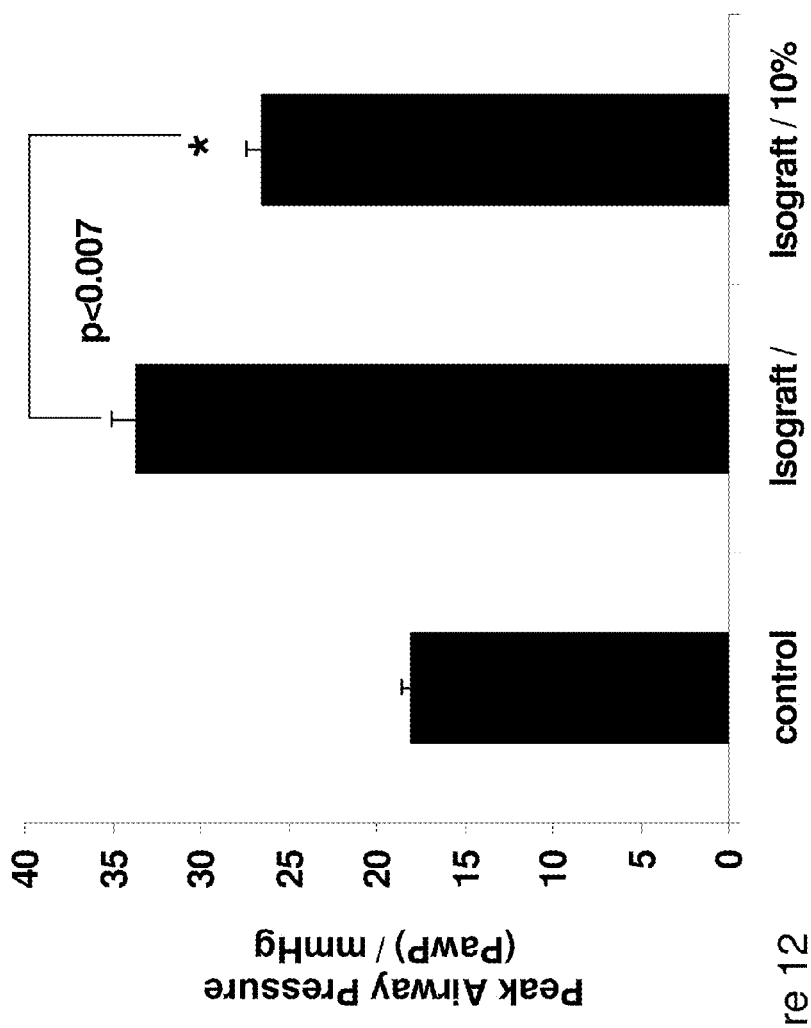
FIG. 12: shows that peak lung pressures is significantly improved in flaxseed-fed rats that underwent orthotopic lung transplantation.

Dietary Flaxseed Protects from Lung Transplantation-related Acute Lung Injury in a Rat Model of Orthotopic Lung Transplantation A rat model of rat lung transplantation was recently developed. As a preliminary test of the hypothesis that flaxseed diets could ameliorate lung transplant induced IRI, some very preliminary studies were conducted in three rats. Flaxseed diets were fed to both donor and recipient rats (2 weeks on diet) prior to lung transplantation. Eighteen hours post-transplantation, hemodynamic parameters were determined and a histopathological examination of the lung was performed. Flaxseed-treated rats showed decreased lung inflammation and interstitial edema (FIG. 11C) associated with the procedure as compared to rats fed a normal chow (FIG. 11B) while FIG. 11A is an untreated control lung. In addition, peak lung pressures were significantly improved in flaxseed-fed rats (FIG. 12).

This data shows that the flaxseed/transplant hypothesis is valid.

Example 10

Figure 13:
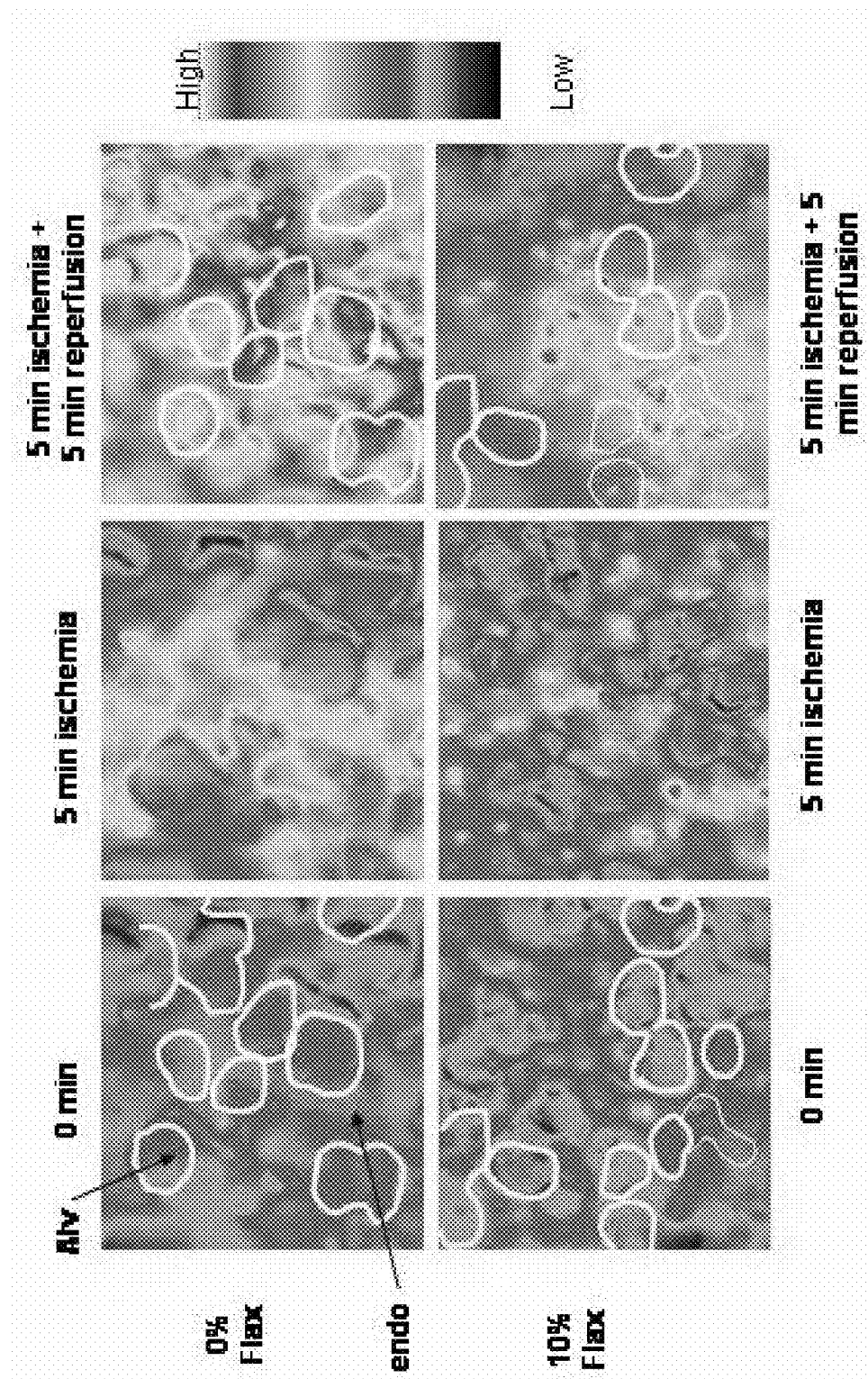
FIG. 13: shows in-vivo imaging of the effect of a flaxseed diet on generation of ROS in EC after IR.

Dietary Flaxseed Inhibits Endothelial ROS Generation in an ex vivo Model of Lung Ischemia/Reperfusion The data presented above convincingly show that flaxseed diets reduce lung injury and reduce markers of oxidative injury, such as MDA levels, however these systems do not allow us to actually visualize ROS levels. To accomplish this, a system developed at PENN in was used, in which lung ischemia reperfusion is studied in real time, in living mice, using confocal microscopy to visualize specific injected, circulating fluorescent dyes that can measure ROS levels or other interesting cellular parameters (ion flows). Using this system, it was determined that quickly after flow is reestablished in an ischemia reperfusion model, there is a marked rise in ROS production in lung endothelial cells. This is due to a mechanical transduction of the flow signal that first involves endothelial cell (EC) membrane depolarization mediated by an EC ATP-sensitive potassium ($K_{ATP}$) channel which then leads to assembly and activation of the NADPH oxidase complex in the EC membrane that produces high levels of endogenous ROS. Our collaborator, Dr. Chatterjee, used the in vivo imaging system to evaluate the effect of a flaxseed diet on generation of ROS in EC after IR—(FIG. 13).

Figure 14:
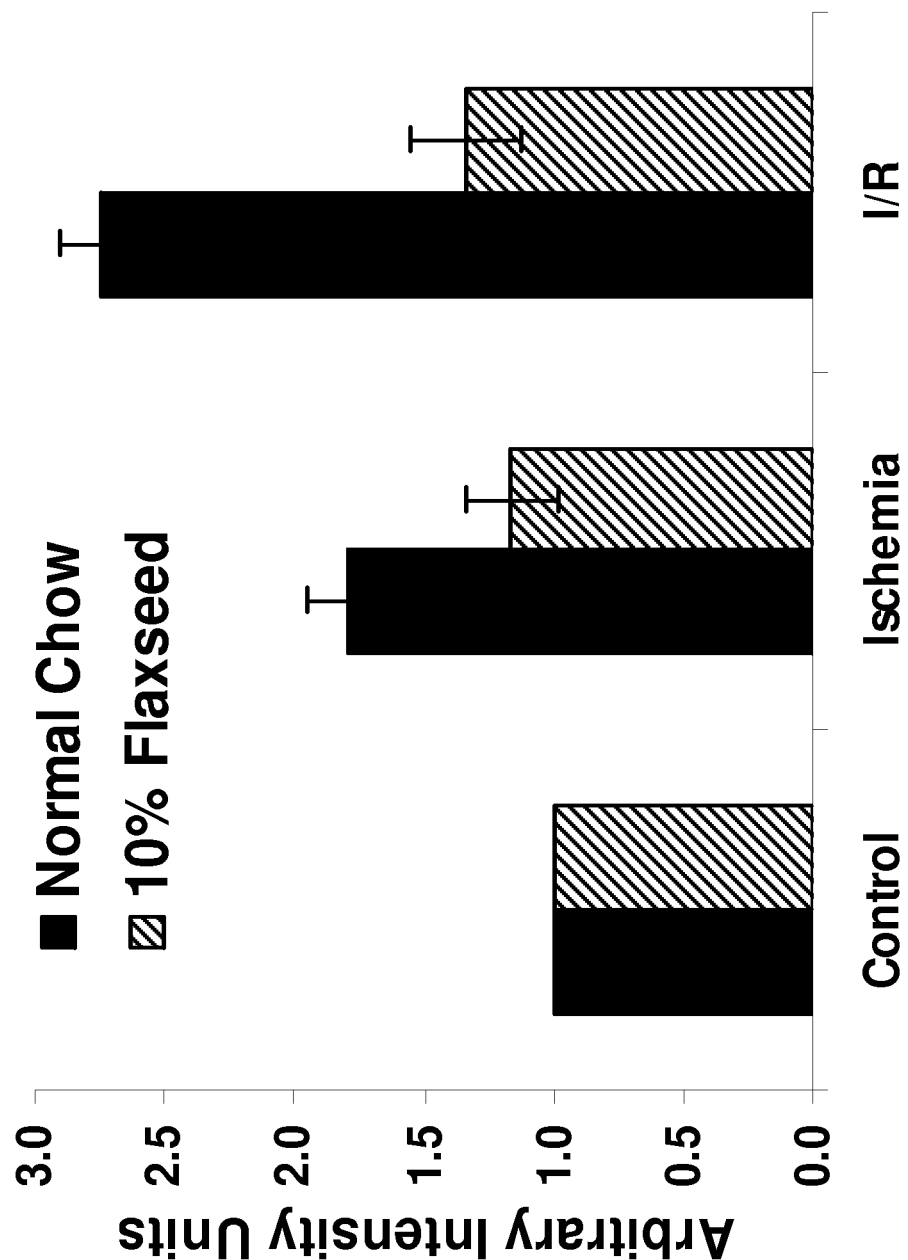
FIG. 14: shows increased intracellular ROS levels, as measured by 2',7'-dichlorodihydro fluorescein (DCF) taken by cells as measured by dye uptake. This was blunted in the Flax-fed animals.

Isolated perfused mouse lungs were taken from flaxseed-fed (3 weeks on 10% diet) or control mice and labeled with 2',7'-dichlorodihydro fluorescein (DCF). This dye is taken up by cells and measures ROS levels. The lungs were imaged using the confocal scope (0 min). After global ischemia (5 minutes), lungs were re-imaged. A small increase in dye intensity [red color] was seen in subpleural endothelial cells (see graph for quantification—FIG. 14) indicating increased intracellular ROS levels, but this was blunted in the Flax-fed animals. The lungs were then re-perfused for five minutes. At this time, a massive increase in ROS was seen in control animals (far left right panels) that was impressively blocked in the flax-fed animals. Semi quantitative assessment of at least 3 fields per lung (3 mice per diet) revealed a near 3-fold increase of fluorescence intensity with I/R in control diets and just 1.2-fold increase over baseline, with 10% dietary flaxseed supplementation.

This data clearly shows that the increased endothelial ROS generation induced by IRI is blunted by a flaxseed diet and illustrates our facility with a key experimental system we will use to dissect mechanisms.

Example 11

Flaxseed Upregulates Two Nrf2-regulated Anti-oxidant and Phase II Enzymes in Murine Lungs in a Dose-dependent Manner One of the mechanistic hypotheses tested, is that flaxseed exerts some of its protective effects by upregulating Phase II enzymes in mouse lungs via in an Nrf-2-dependent manner.

Figure 15:
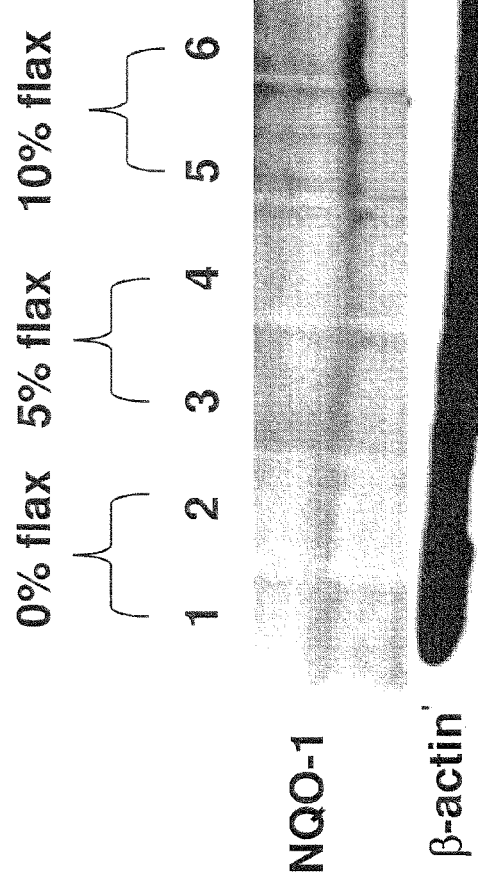
FIG. 15: shows dose dependent increases in quinone reductase (NQO-1) in mice fed a 0%, 5% and a 10% flax diet for 10 week.
Figure 16:
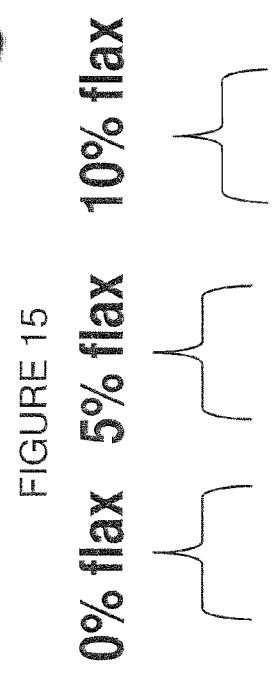
FIG. 16: shows dose dependent increases in the antioxidant enzyme HO-1 in mice fed a 0%, 5% and a 10% flax diet for 10 week.
Figure 16:
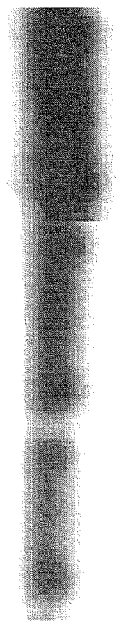

First, mice were fed a 0%, 5% and a 10% flax diet for 10 weeks, lungs harvested, and processed for immunoblotting to measure levels of two Nrf2/ARE-dependent Phase II detoxification enzymes. These blots show dose dependent increases in quinone reductase (NQO-1) (FIG. 15) and the antioxidant enzyme HO-1 (FIG. 16) supporting the hypothesis that flaxseed acts via Nrf2-modulation of ARE-regulated genes.

This data is the first evidence that a flaxseed diet enhances AOEs in mouse tissues, and more specifically in mouse lungs.

Example 12

Figure 17:
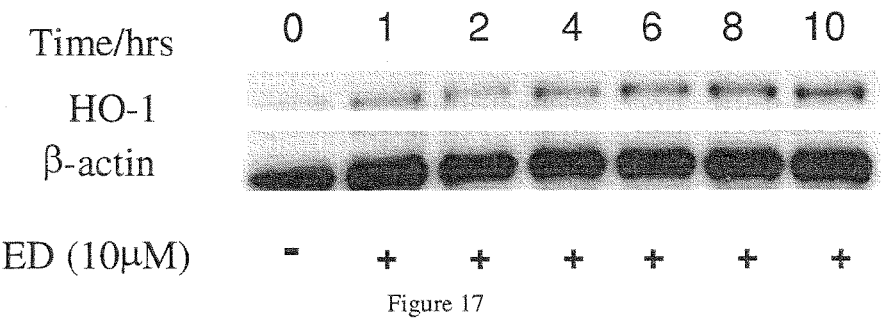
FIG. 17: shows addition of the flaxseed-derived lignan to the endothelial cells results in a robust, time-dependent induction of HO-1.

Chemically Synthesized Mammalian Flaxseed Lignans Upregulate Nrf2-regulated Antioxidant Enzymes in Pulmonary Microvascular Endothelial Cells In Vitro For mechanistic studies, there is a need to establish whether purified lignans (in appropriate, "pharmacologically achievable" concentrations) have similar effects in cell culture as lignan complex diets have in animals. HO-1 levels were thus evaluated by immunoblotting in primary cultures of pulmonary microvascular endothelial cells (PMVEC) isolated from mouse lungs. PMVEC were incubated with the lignan enterodiole (ED) in micromolar concentrations (10□M) similar to that seen in mouse plasma levels. Cells were incubated with ED for 1,2,4,6,8 and 10 hours. Addition of the flaxseed-derived lignan to the endothelial cells resulted in a robust, time-dependent induction of HO-1 (FIG. 17). Similar findings were shown with the flaxseed lignan (EL).

Figure 18:
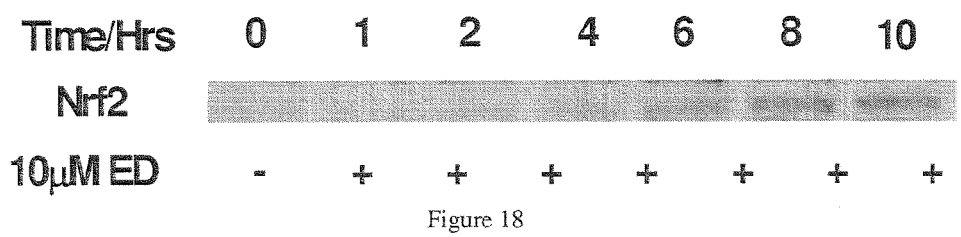
FIG. 18: shows that while very low basal levels of Nrf2 are present in control, untreated cells at all times, (first lane, control), lignans induced a time-dependent increase of nuclear Nrf2 levels.

Treatment of unchallenged, primary cultures of isolated pulmonary microvascular endothelial cells with flaxseed lignan ED (10 µM) indicated that while very low basal levels of Nrf2 are present in control, untreated cells at all times, (first lane, control), lignans induced a time-dependent increase of nuclear Nrf2 levels (FIG. 18). Similar findings were shown with EL. Nrf2 was detected with our own rabbit polyclonal Antibody (Clone MCS-1a).

Example 13

Flaxseed Lignans Reduce Cell Death Induced by Oxidative Stress

Figure 19:
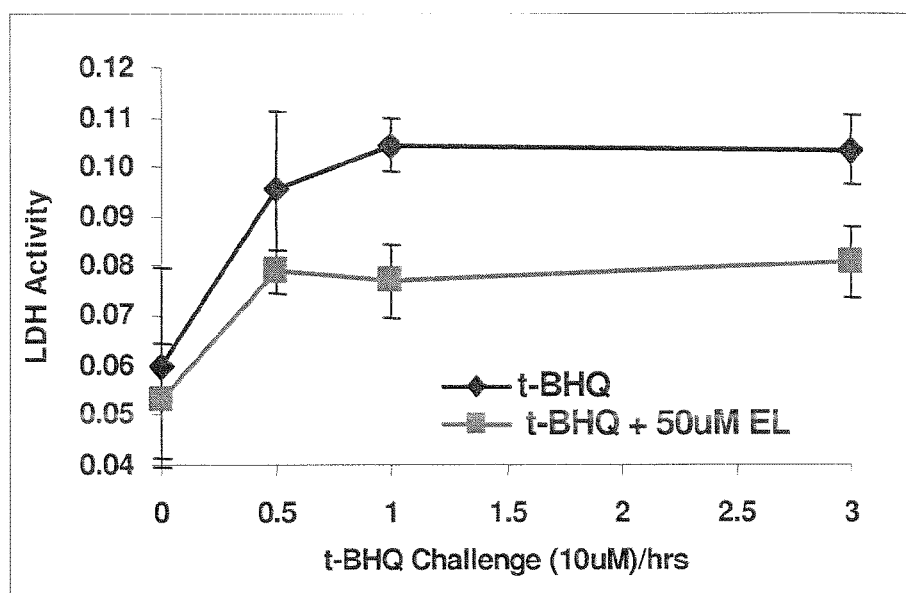
FIG. 19: shows that treatment of PMVEC with 10 µM of tBHQ leads to marked LDH release (indicating cell death) of PMVEC within 30-60 minutes. However, pretreatment of cells with 50 µM of the chemically synthesized, commercially available lignan Enterolactone (EL) is sufficient to protect cells up to 50% from tert-butylhydroquinone (tBHQ)-induced cell death.
Figure 21:
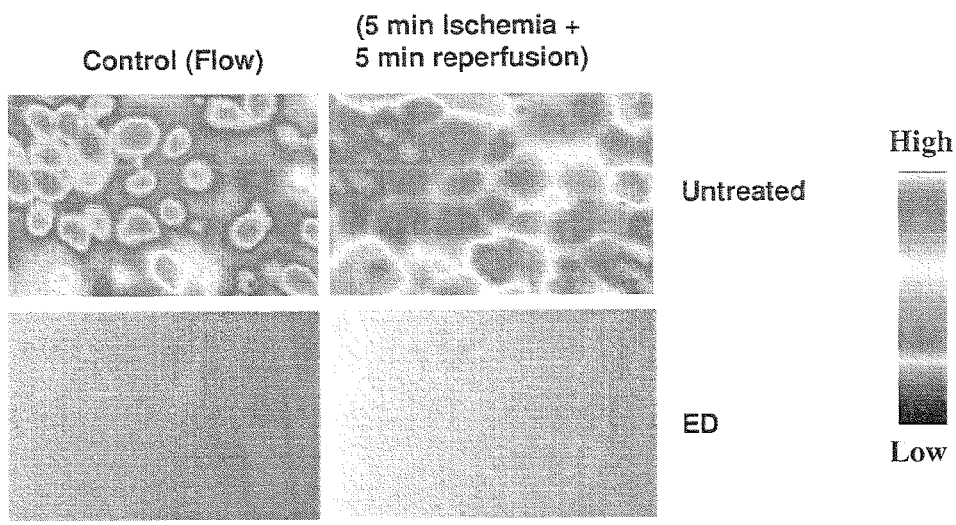
FIG. 21: shows a near complete abrogation of ROS generation by chemically synthesized, commercially available lignan-pre-treated EC, as evidenced from pseudocolor images of H2DCF uptake by the cells to monitor ROS generation.

Given the in vivo data hereinabove, showing protection of lungs from oxidative injury after flaxseed feeding, a confirmation of similar protection of cells in vitro was desired. Relatively high doses of the electrophile tert-butylhydroquinone (tBHQ) were used to oxidatively stress the cells. As shown in FIG. 21, treatment of PMVEC with 10 µM of tBHQ led to marked LDH release (indicating cell death) of PMVEC within 30-60 minutes. However, pretreatment of cells with 50□M of the lignan Enterolactone (EL) was sufficient to protect cells up to 50% from tert-butylhydroquinone (tBHQ)-induced cell death (FIG. 19).

Figure 20:
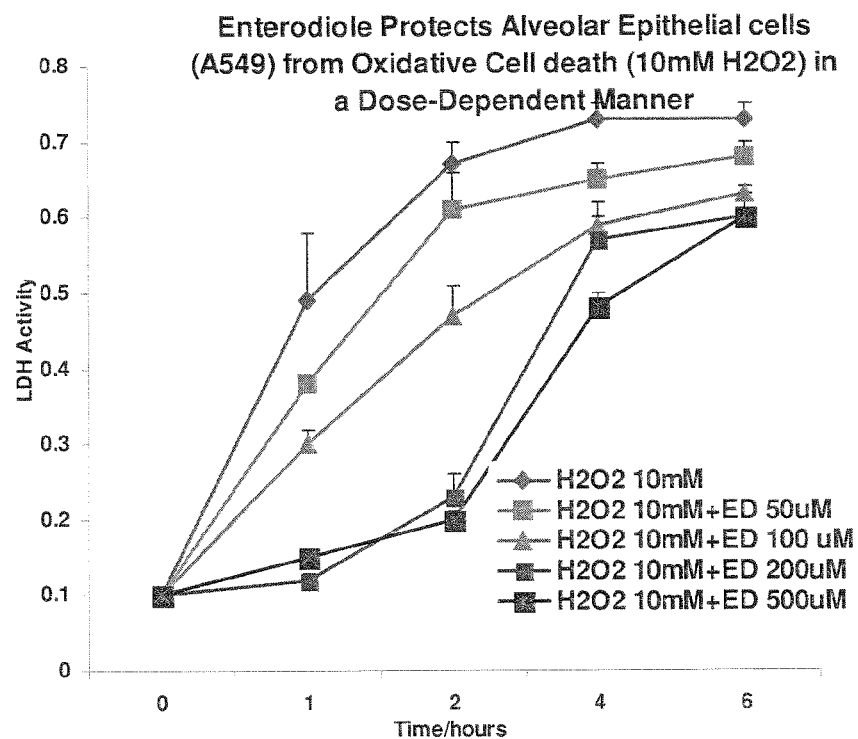
FIG. 20: shows that the chemically synthesized, commercially available lignan ED, significantly protects epithelial cells from cell death in a dose-dependent manner.

In addition, using the same assay system to detect cell death, LDH release, an evaluation of the efficacy of the lignan enterodiole, ED, to protect alveolar epithelial cells (A549) from oxidant-induced cell death was made. In these experiments, cells were pre-incubated withincreasing concentrations of ED (10, 50, 100, 200, 500 uM) and challenged with hydrogen peroxide (10 mM H2O2) for 1-6 hours. ED, significantly protected epithelial cells from cell death in a dose-dependent manner. (FIG. 20).

These findings show that the flaxseed lignans can protect cells from oxidative stress-induced death.

Example 14

Chemically Synthesized Mammalian Flaxseed Lignans Reduce ROS Production by EC in Response to IRI (in vitro)

Mouse pulmonary endothelial cells (PMVEC) were grown on coverslips and placed in a Warner chamber and perfused with culture medium for 24 h at a flow rate of 10 dyn/cm². Cells were incubated with the Lignan ED (5 µM) for 5 h prior to I/R loaded with H2DCF to monitor ROS immediately before the experiment. I/R in this chamber is simulated by abrupt cessation of perfusate flow and its reinstatement through the chamber 5 minutes later. The images are in pseudocolor with intensity shown on the side bar. FIG. 21 shows a near complete abrogation of ROS generation by lignan-pre-treated EC (lack of yellow-red color).

Example 15

Flaxseed Lignans Act as Proteasomal Inhibitors $GFP^u$-1 cells were used to investigate the impact of one of the flaxseed lignans, enterodiole (ED) on proteasomal activity. $GFP^u$-1 is an human kidney epithelial (HEK)-derived, stably transfected cell line expressing a short degron (CL1)

tagged to green fluorescent protein (GFP) as described (ref). ED increased GFP levels in a dose-dependent fashion, a robust indication of proteasomal inhibition as shown by anti-GFP immunoblotting.

Figure 29:
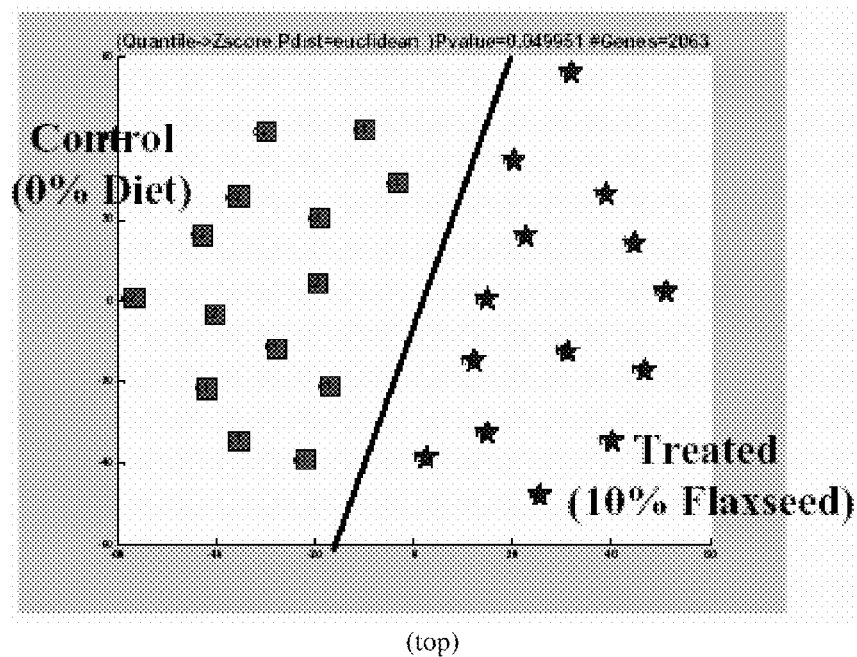
FIG. 29: shows a microarray analysis of lung tissues following dietary whole-grain flaxseed supplementation (10%).
Figure 29:
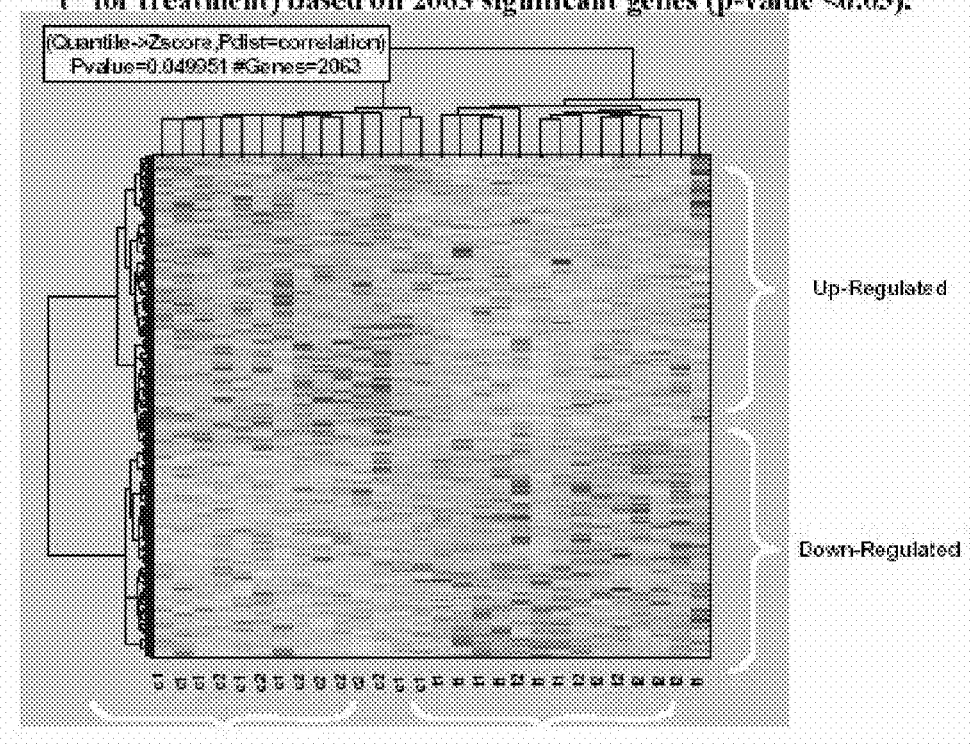

Microarray analysis of lungs from 14 control-diet fed and 14 flaxseed-fed mice (at least 3 weeks on the diet) was performed on 28,800 mouse genes. Analysis revealed 2063 statistically significant genes (p<0.05) modified by the FS diet. Top FIG. 29 shows the samples of the two classes (control diet vs. 10% FS) in two-dimensional space (Principle Component Analysis). Bottom FIG. 29 shows Hierarchical cluster analysis of the two classes (FS treatment and control), Taken with the findings of the protective effects of FS diet in radiation pneumonopathy, this data indicates that pre-feeding FS alters the expression of certain genes favoring abrogation of pro-inflammatory and pro-fibrogenic pathways. Importantly, FS may act on the tumor microenvironment blocking tumor growth and metastasis.

Figure 30:
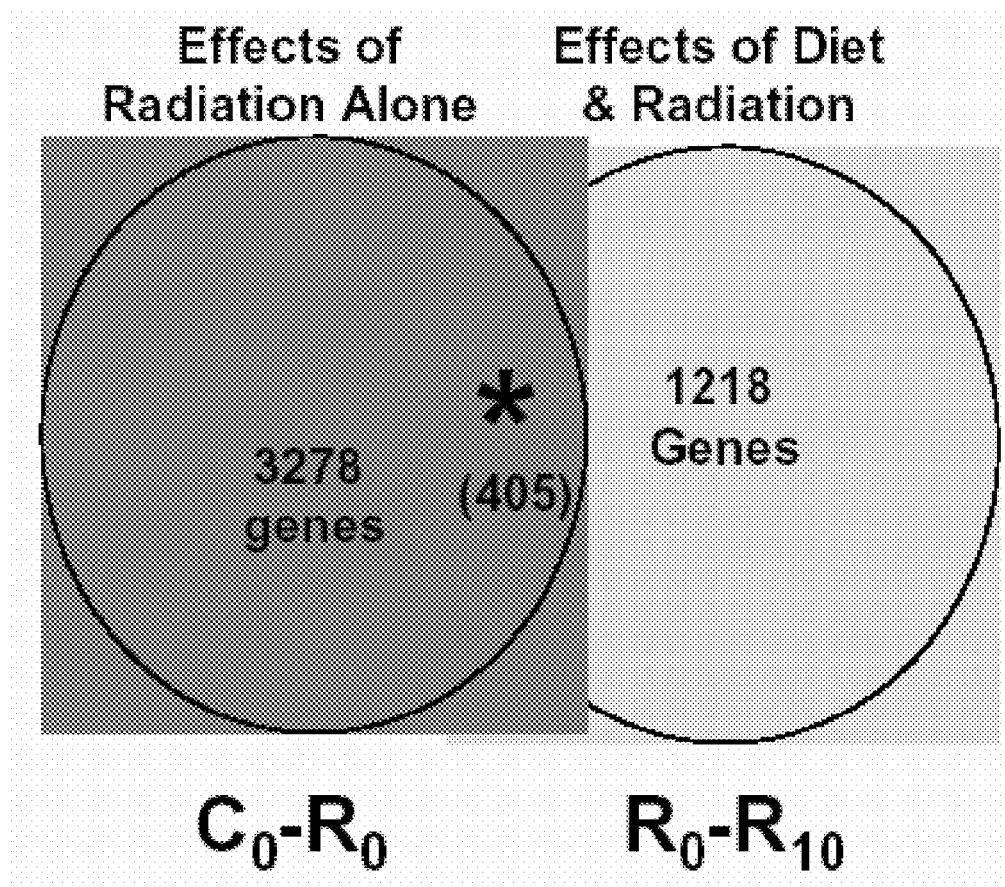
FIG. 30: Dietary wholegrain Flaxseed (10%) Reversed Radiation-Induced Alterations Of Gene Expression In Murine Lungs.

Gene changes were evaluated in lung tissues from irradiated mouse lungs given control or FS diet for 3 weeks, irradiated with a single fraction thoracic XRT (13.5Gy) and lungs excised 48 hours post XRT. This generated 2 data sets shown in FIG. 30, one for irradiated 0% ($R_0$) and irradiated 10% FS($R_{10}$). RNA was isolated and Microarray analysis performed for 28,800 mouse genes (n=6 mice/diet). Control, non-irradiated mouse lungs for each diet, gave rise to 2 additional data sets, namely control 0% ($C_0$) and control 10% FS ($C_{10}$) (n=14). Results indicated the following: R0-R10: Post radiation (48 hrs), mice have 1,218 genes that are differentially expressed due to both the diet and the radiation effects. C0-R0: Radiation alone induces 3,278 genes to be differentially expressed in mice fed a control diet.

The set of genes differentially expressed due to radiation alone that are also significantly changed due to the effects of FS diet post radiation (405 genes). Remarkably, of These Genes, 93% (378 genes) are reversed In Their Expression by FS. All genes are p<0.05.

Example 16

Dietary Flaxseed Prevents Tumor Growth

Figure 25:
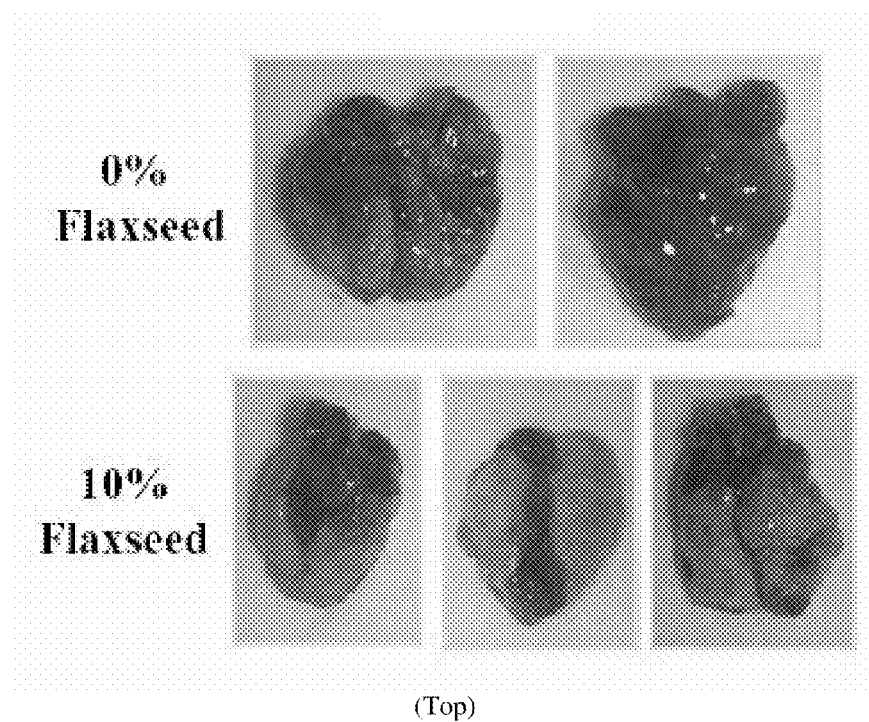
FIG. 25: shows that dietary flaxseed prevents lung tumor growth (% lung area occupied by tumor counted by image analysis software) and metastasis (number of tumor nodules) shown in clinical figure (top) and graph format (bottom).
Figure 25:
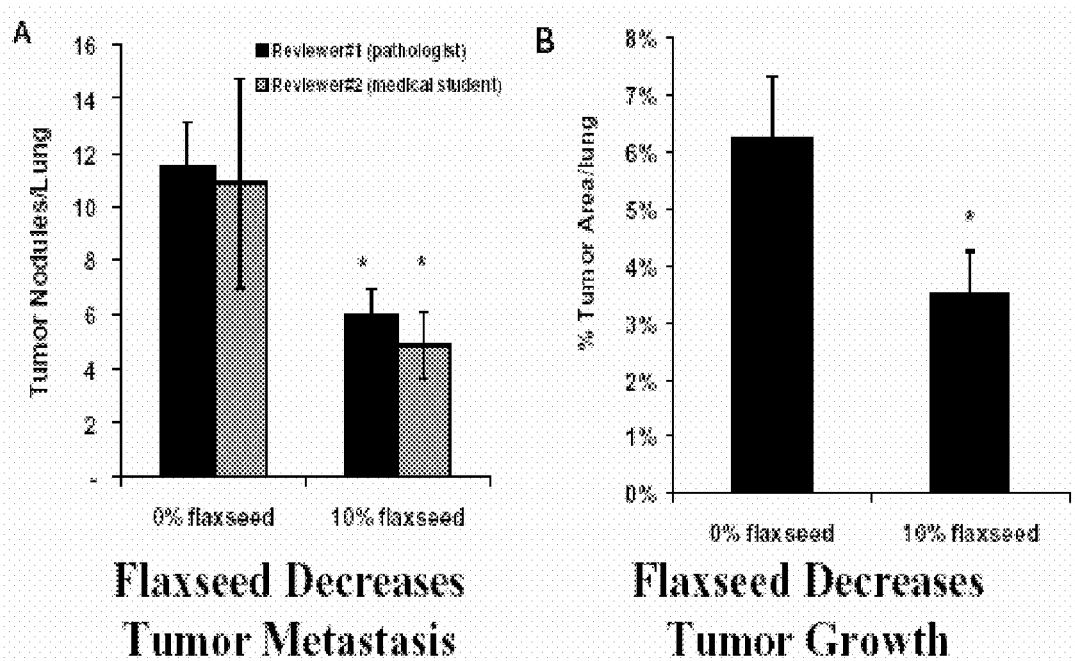

FIG. 25 shows that dietary flaxseed prevents lung tumor growth (% lung area occupied by tumor counted by image analysis software) and metastasis (number of tumor nodules) shown in clinical figure (left) and graph format (right): Lung cancer cell lines were injected iv in mice via tail vein ($1\times10^6$ cells) and tumor growth and metastasis was measured 3 weeks later. Tumor nodules were counted from histological lung sections blindly by a lung pathologist and a medical student. Results indicated a significant decrease in lung metastases by dietary supplementation of 10% FS initiated on the day of iv lung cancer cell injection.

Figure 32:
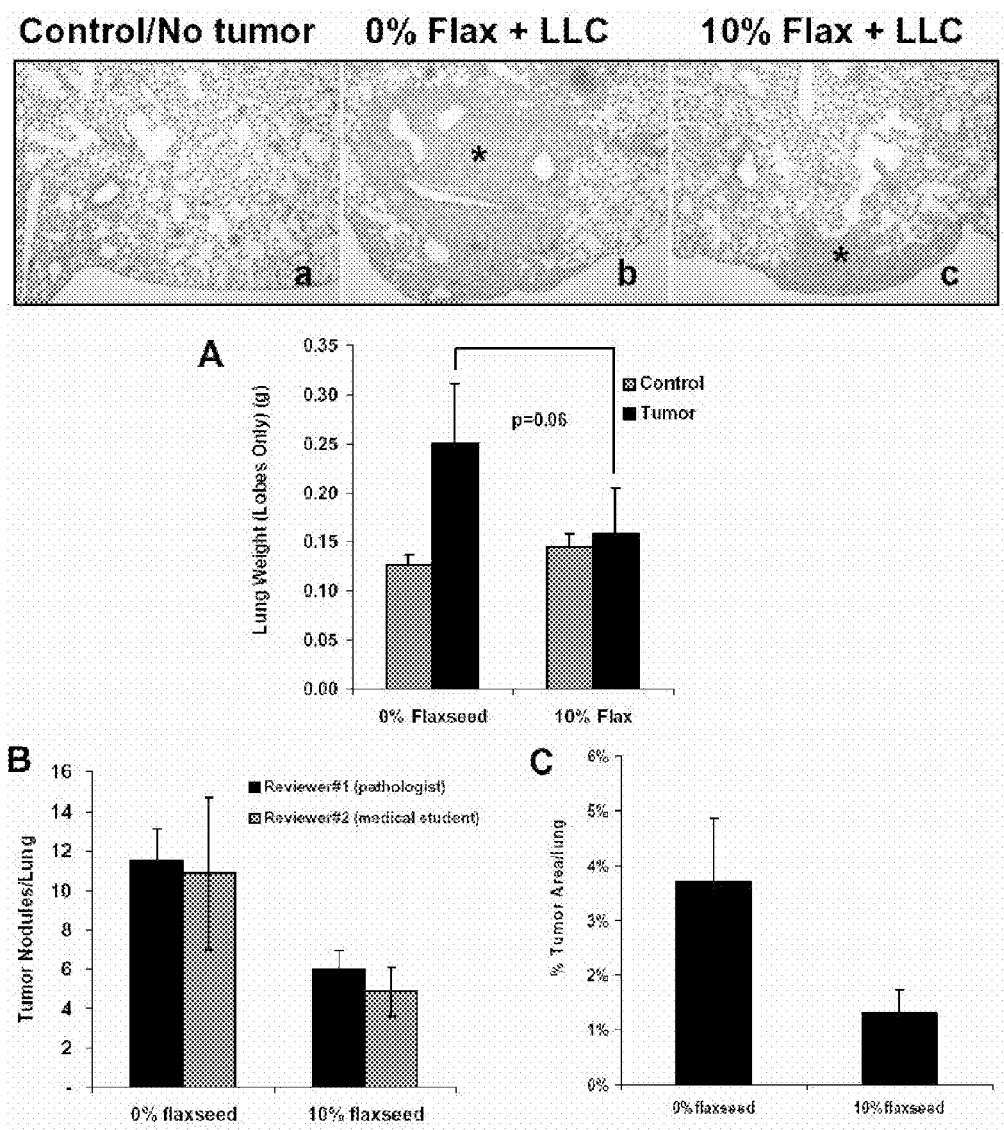
FIG. 32: Dietary Flaxseed reduces tumor metastasis and growth in mouse lungs. Mice were fed either a 0% or 10% FS supplemented diet for at least 3 weeks (n=10 mice/diet) were injected iv with 2 million LLC cells and lungs were excised and evaluated histologically with H&E staining, * represent tumor nodules. (Top panels). Overall tumor burden was assessed using lung weights (Panel A). Image analysis was performed for determination of tumor metastasis number (nodules/lung, Panel B), and overall tumor size (% tumor area/lung, Panel C).

Dietary FS reduces tumor growth and metastases in mouse lungs Mice were fed for three weeks with 0% or 10% FS prior to the injection of 2×106 LLC cells intravenously. At 10 days post injection, mice were sacrificed from each treatment group, lungs were excised for histological evaluation (FIG. 32, Top panels). Lungs were also weighed as an assessment of overall tumor burden (FIG. 32, Panel A). There was no significant difference in overall mouse weight (mean weight 19.3±0.25 vs. 19.8±0.30 grams in 0% FS and 10% FS fed mice, respectively). Histological analysis was performed by two blinded, independent reviewers to measure tumor nodules. There was a significant decrease in tumor nodules in the FS fed group (FIG. 32, Panel B). The percent tumor area per lung was also measured. There was a significant decrease in % tumor area in the 10% FS supplemented group, again suggesting overall decreased tumor burden from lung metastases (FIG. 32, Panel C).

Lung tumor burden was also decreased by FS diet as evidenced by lung weight measurements. This was also evidenced by clinical observation of the excised lungs. This provides the first evidence that flaxseed inhibits lung cancer tumor growth and metastasis.

Figure 26:
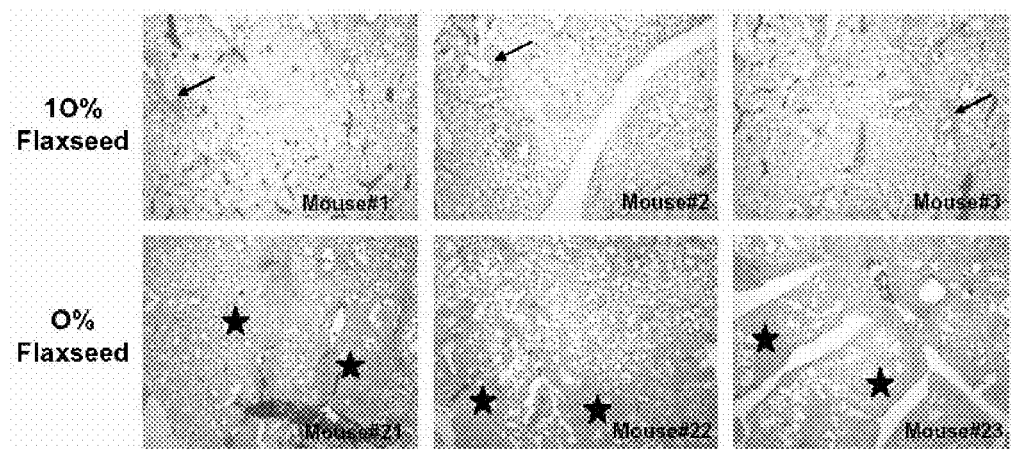
FIG. 26: shows that Dietary Whole Grain Flaxseed (10%) is highly effective in a murine orthotopic model of bronchogenic adenocarcinoma of the lung.
Figure 26:
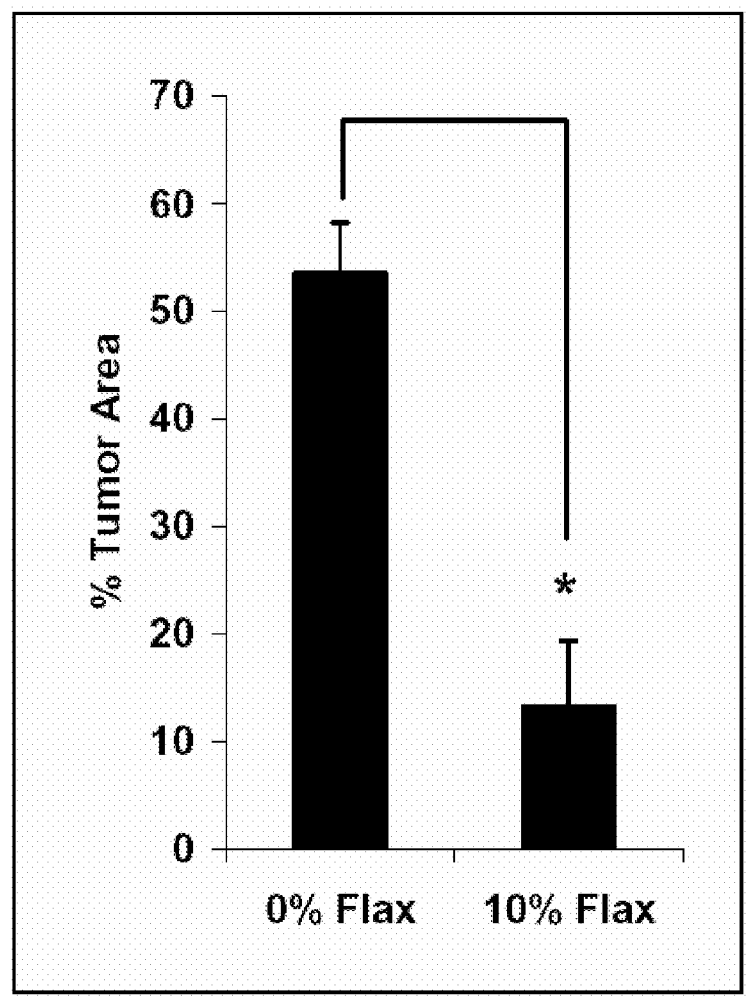
Figure 27:
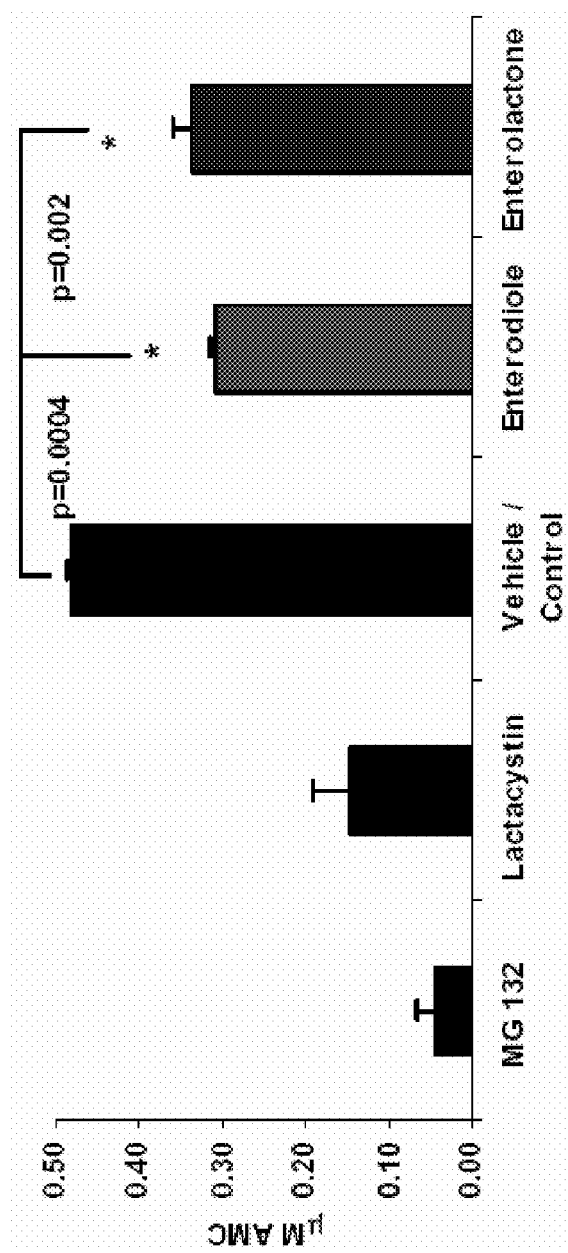
FIG. 27: shows how synthetic Flaxseed Lignans Act as Proteasomal Inhibitors when Incubated with Murine Cells in Culture.
Figure 28:
FIG. 28: shows how synthetic Flaxseed Lignan enterodiole (ED) Acts as Proteasomal Inhibitor in a dose dependent fashion when incubated with epithelial Cells in Culture.

As shown in FIG. 26, Mice were injected intratracheally with X109 Ad.Cre virus particles to initiate tumor formation and diet was initiated (0% vs. 10% Flaxseed) on the same day (n=20 per diet). Three (3) mice from each diet (Mouse 1-3 from 10% Flaxseed and mouse 21-23 from the 0% flaxseed diet) were sacrificed a month post tumor initiation for histopathological assessment. Mice fed whole-grain flaxseed had significantly less lung cancer burden shown histologically (top figure) and by measurement of tumor area (57% tumor in controls vs. 13% with FS) using image analysis software (bottom graph).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

Example 17

Dietary FS Inhibits Lung Tumor Growth in the Flanks of Mice

Figure 31:
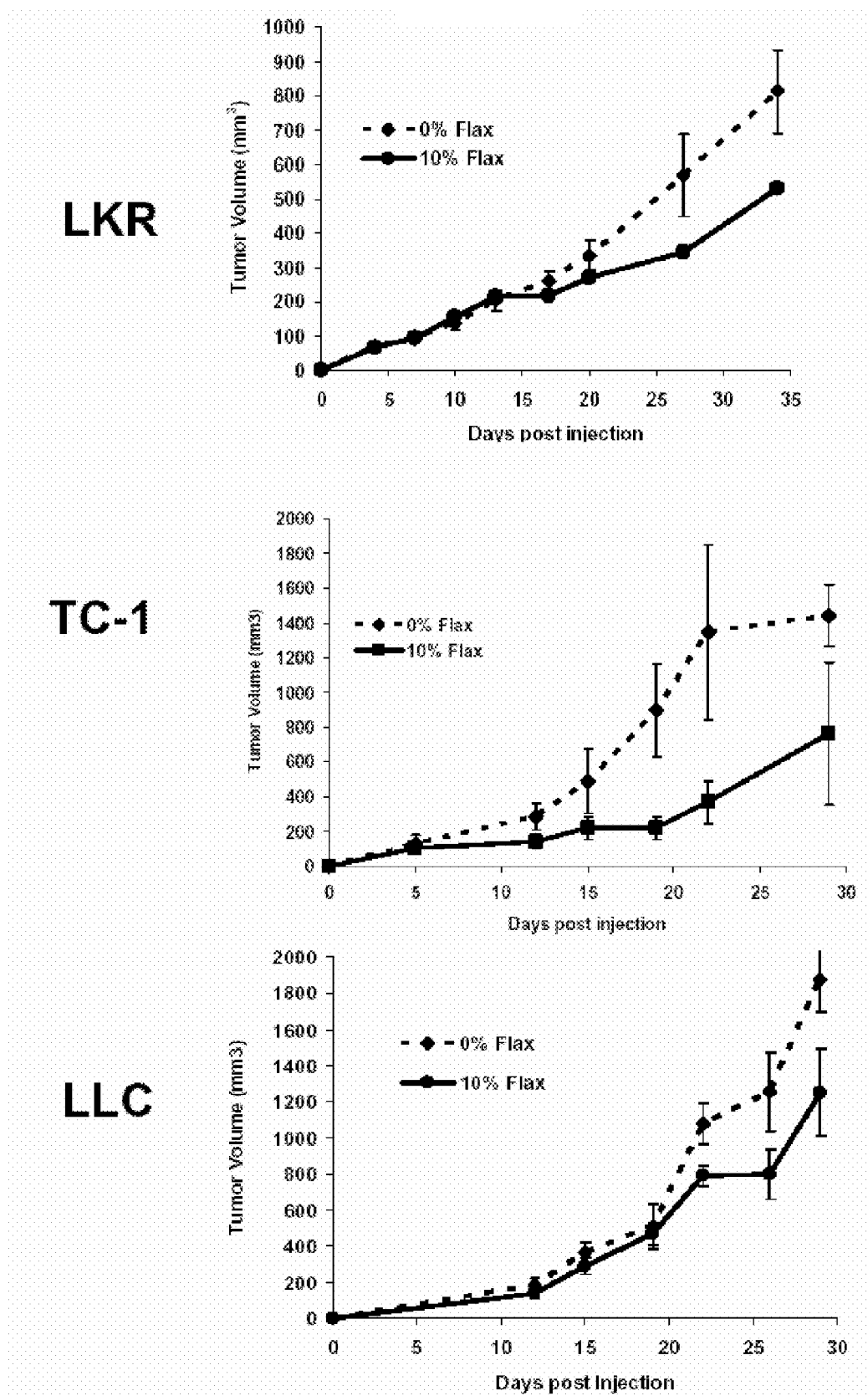
FIG. 31: Dietary Flaxseed inhibits lung tumor growth in the flanks of mice. 10% FS in the diets of mice given 3 weeks prior to the injection of 2 million lung cancer cells (Kras-derived LKR, TC-1, and LLC) in the flanks of mice was evaluated. Mice were kept on the diets for an additional 2-4 weeks and tumor size was evaluated every 3-4 days. Values represent means of 5 tumors±SEM.

Mice were fed for three weeks with 0% or 10% FS prior to the injection of 2×106 lung cancer cells (Kras-derived LKR, TC-1, LLC, AB-12, or L1C2) into the flanks of mice (n=? mice per diet per tumor line). Control and treatment diets were continued for the duration of the experiment (4-5 weeks post flank injection). Tumor size was evaluated every 3-4 days with volume determinations (FIG. 31). In three of the five cell lines tested (LKR, TC-1, and LLC), there was a significant decrease in rate of tumor growth and volume by approximately three weeks post flank injection.

Example 18

Dietary FS Reduces Tumor Growth in Mouse Lung in Tobacco Carcinogen-induced Lung Cancer Briefly, A/J mice were injected i.p. with B[a]P (1 μg) for 3 weeks (once weekly). As controls, mice were injected with tricapryllin, the solvent/vehicle used for the B[a]P injections. Mice were placed on a 10% flaxseed-supplemented diet or a 0% Flaxseed, control diet from initiation of B[a]P injections. Mice were harvested 5 months post initiation of the injections and lungs evaluated histologically for tumor formation (n=5 mice per diet). Additional animals will be sacrificed at 6, 7, and 9 months post B[a]P.

Figure 33:
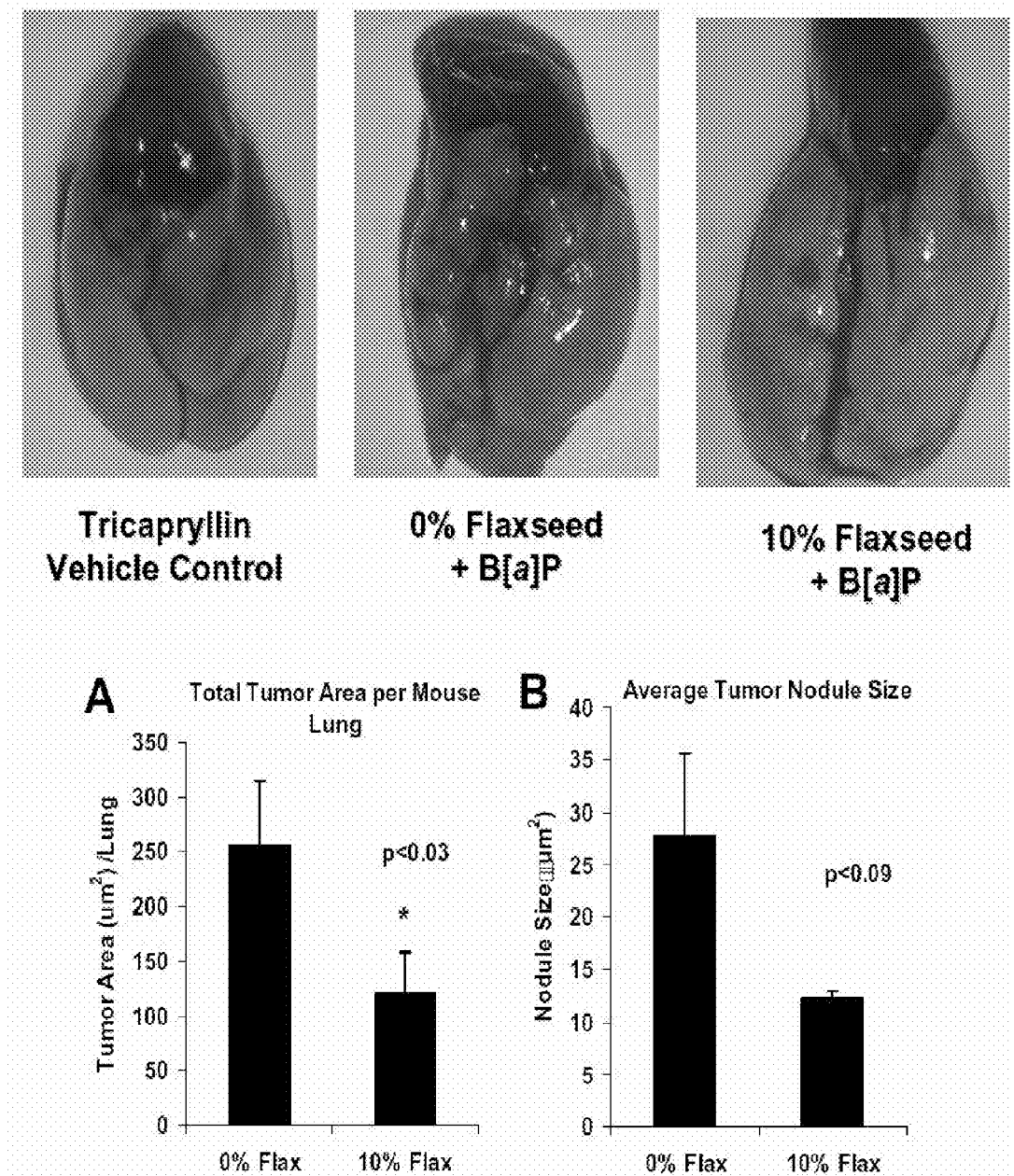
FIG. 33: Flaxseed abrogates B[a]P-induced lung nodule growth. A/J mice were injected with 4 weekly doses of 1 mg/mouse of B[a]P and lungs were evaluated 6 months later for tumor burden. Lung tissue sections (H&Es) were quantitatively assessed after 5 months for tumor. Panel A: Total tumor area per mouse (mm2); Panel B: Nodule size/area (mm2). Values are given as mean±SEM. Sample size=5 mice/group.
Figure 34:
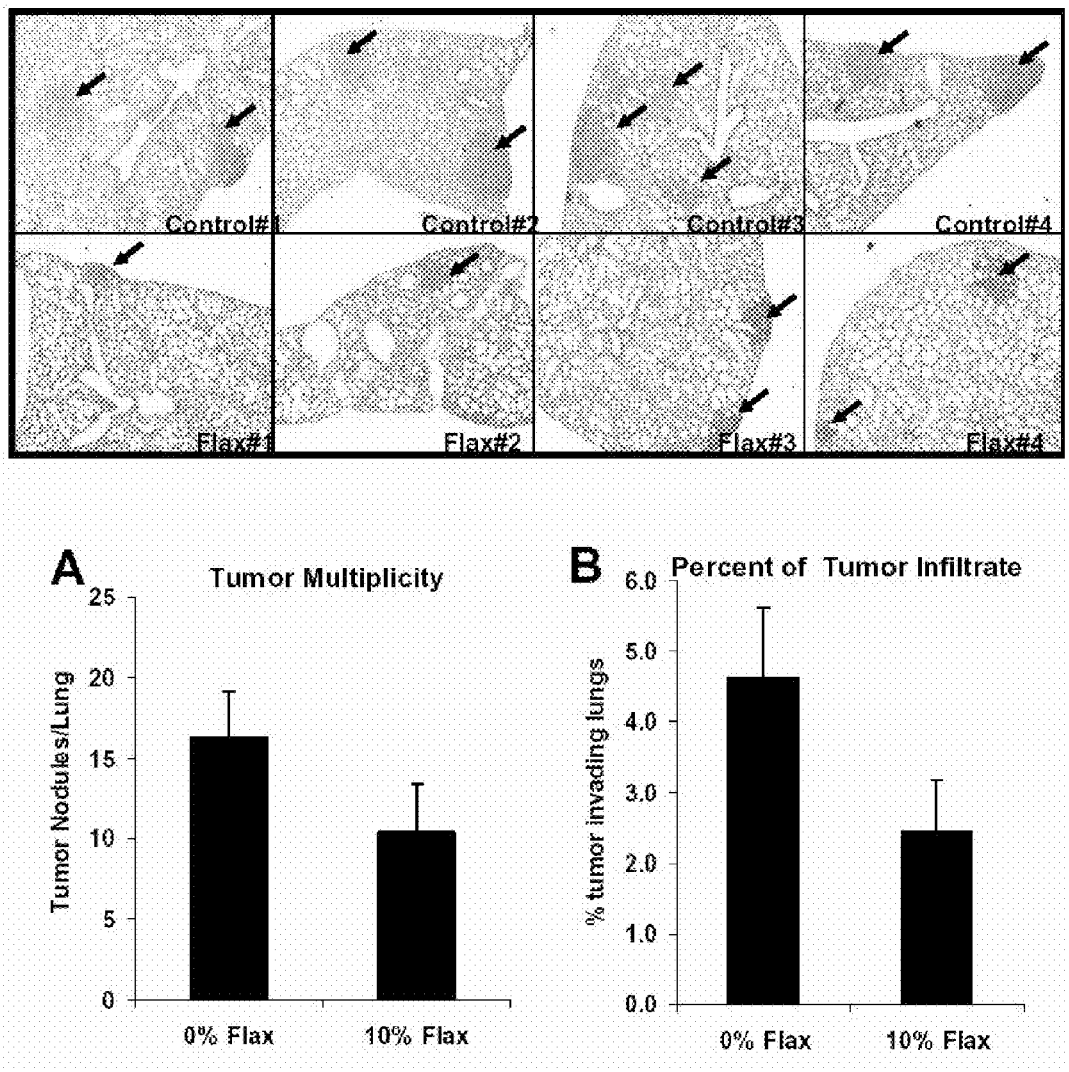
FIG. 34: Lung tumor volume is decreased with flaxseed. Histological views of control (top row) and flaxseed-fed (bottom row) lungs, 6 months post B[a]P injections (100×). Panel A: Tumor multiplicity (nodules/lung); Panel B: Percent Tumor Infiltrate (% tumor invading lungs). Values are given as Average±SEM. Sample size=5 mice/group.

FIGS. 33 and 34 show representative, clinical and histological views, respectively, of mouse lungs from mice fed a 0% control diet vs. mice fed a 10% flaxseed-supplemented diet. Tumor incidence was 100% for both 0% and 10% Flaxseed diet. However, qualitatively, the tumor nodules appeared much smaller in lungs from the 10% flaxseed-fed mice. Indeed, quantification of tumor area using Phase 3 Image analysis software indicated that there was a significant decrease in overall tumor area (p<0.03) and a trend towards decreased individual nodule size (p<0.09) with flaxseed supplementation. This is indicated in FIG. 33, Panels A and B, respectively. Since % of lung area infiltrated by tumor is just 4.6%±1% for 0% flaxseed and 2.4%±0.8% for 10% flaxseed, i.e., still very small 5-6 months post injection of B[a]P, this trend may be further enhanced as tumor burden increases.

In Summary, this data provides robust evidence that a) the selected dose and mode of administration of B[a]P generates a reproducible lung carcinogenesis model and b) that flaxseed supplementation seems to retard lung tumor growth and incidence (FIG. 34).

Example 19

Cancer Cell Proliferation is Inhibited by Known Proteasomal Inhibitor

Figure 35:
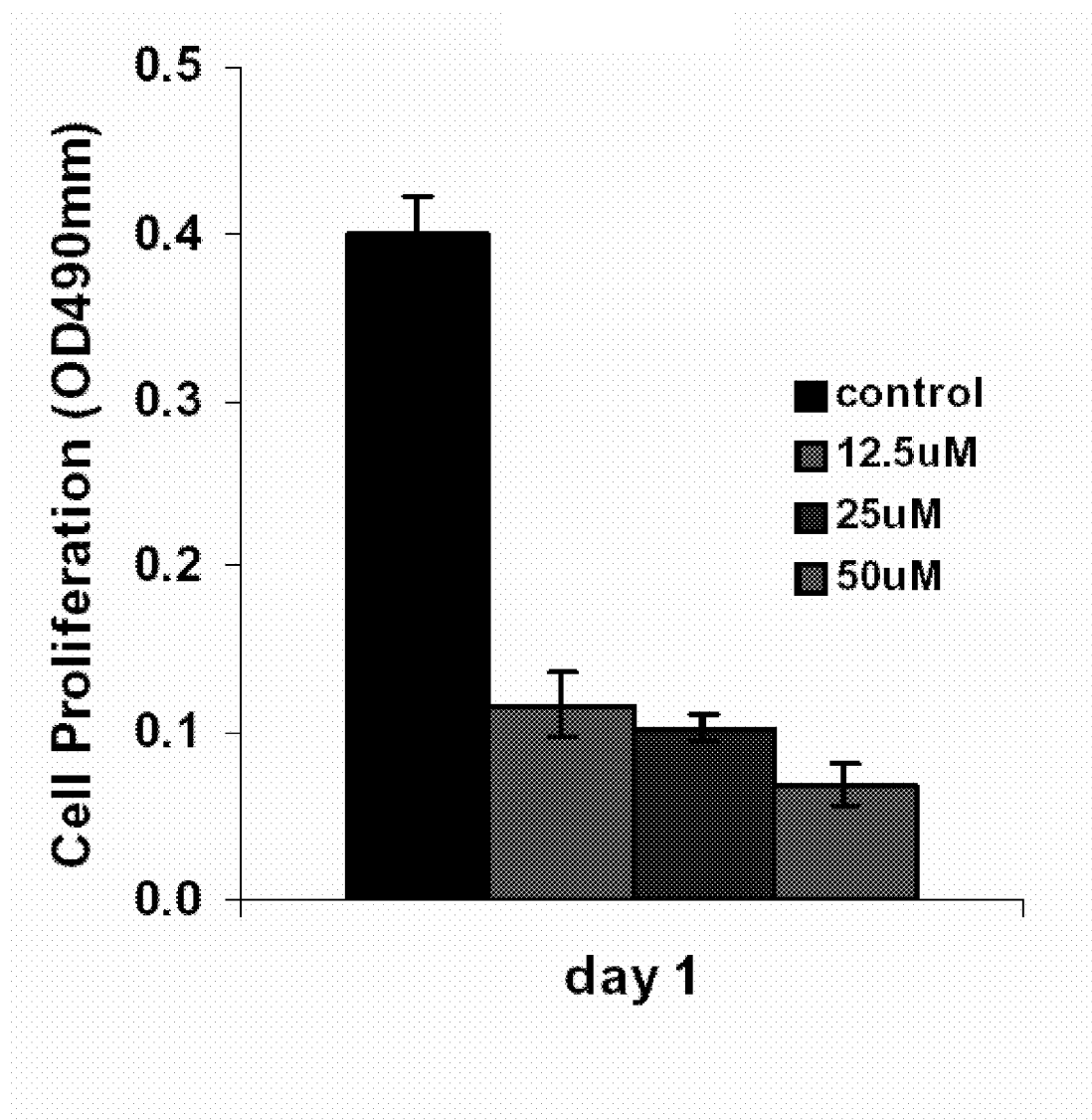
FIG. 35: Cancer cell proliferation is inhibited by a known pharmacological proteasome inhibitor. LKR cells were incubated with MG 132, a known pharmacological proteasomal inhibitor and cell proliferation was measured using the MTS assay at one day post incubation. There was a dose dependent decrease in cell proliferation with increasing doses of MG 132.

LKR cells derived from an explant of a pulmonary tumor from an activated K-rasG12D mutant mouse were incubated with differing concentrations of MG 132, a known pharmacological proteasomal inhibitor to assess for cell proliferation using the MTS assay. As seen in FIG. 35, there was a clear dose dependent response of MG 132 with increasing cell proliferation inhibition.

Example 20

Flaxseed Lignans EL and ED Exhibit Proteasomal Inhibition

Figure 36:
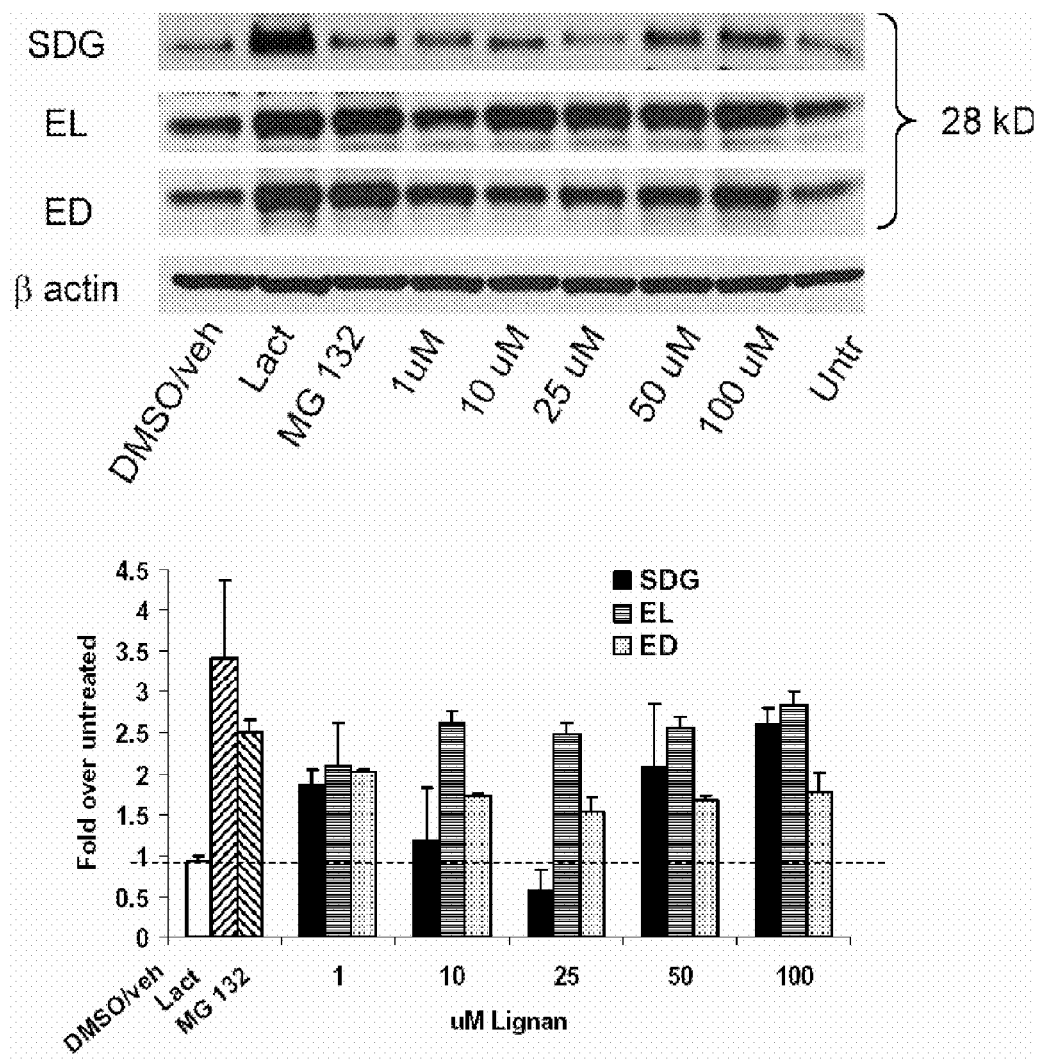
FIG. 36: Proteasomal inhibition with EL and ED as compared to known pharmacologic inhibitors Lactacystin and MG 132. GFPu-1 kidney epithelial cells were treated for 16 hours with EL and ED at differing concentrations. Proteasomal inhibition was detected by Western blotting using anti-GFP antibody with increased proteasomal inhibition expressed as accumulation of GFP. Representative Western blots are shown with β actin reference (Top panels). Densitometry was performed with β actin normalization, expressed as fold over untreated control±SEM, n=2-6 (Bottom panel). Dotted line represents control expression of GFP. *p<0.005 vs. untreated, **p<0.01 vs. untreated.

Using an in vitro means of quantifying proteasomal inhibition with GFPu-1 cells, differing concentrations of the FS lignans EL and ED were compared with known pharmacologic proteasomal inhibitors MG 132 and Lactacystin, incubated for 16 hours prior to processing. Western blotting was performed on whole Flaxseed and Lung Cancer cell lysates using anti-GFP antibodies to quantify the amount of GFP expressed as a marker of the amount of proteasomal inhibition (FIG. 36, Top panels). After densitometry analysis, in all concentrations of EL tested (1 µM to 100 µM), there was a significant increase in proteasomal inhibition compared to untreated cells as seen with increased GFP expression, and no significant difference in the amount of proteasomal inhibition as compared to Lactacystin and MG 132. In the concentrations of ED tested, there was again a significant amount of proteasomal inhibition compared to untreated cells, but the amount of proteasomal inhibition achieved was comparable to only Lactacystin, not MG 132 (FIG. 36, bottom panels).

Example 21

FS Lignans Inhibit Cell Proliferation of Lung Tumor Cell Lines

Figure 37:
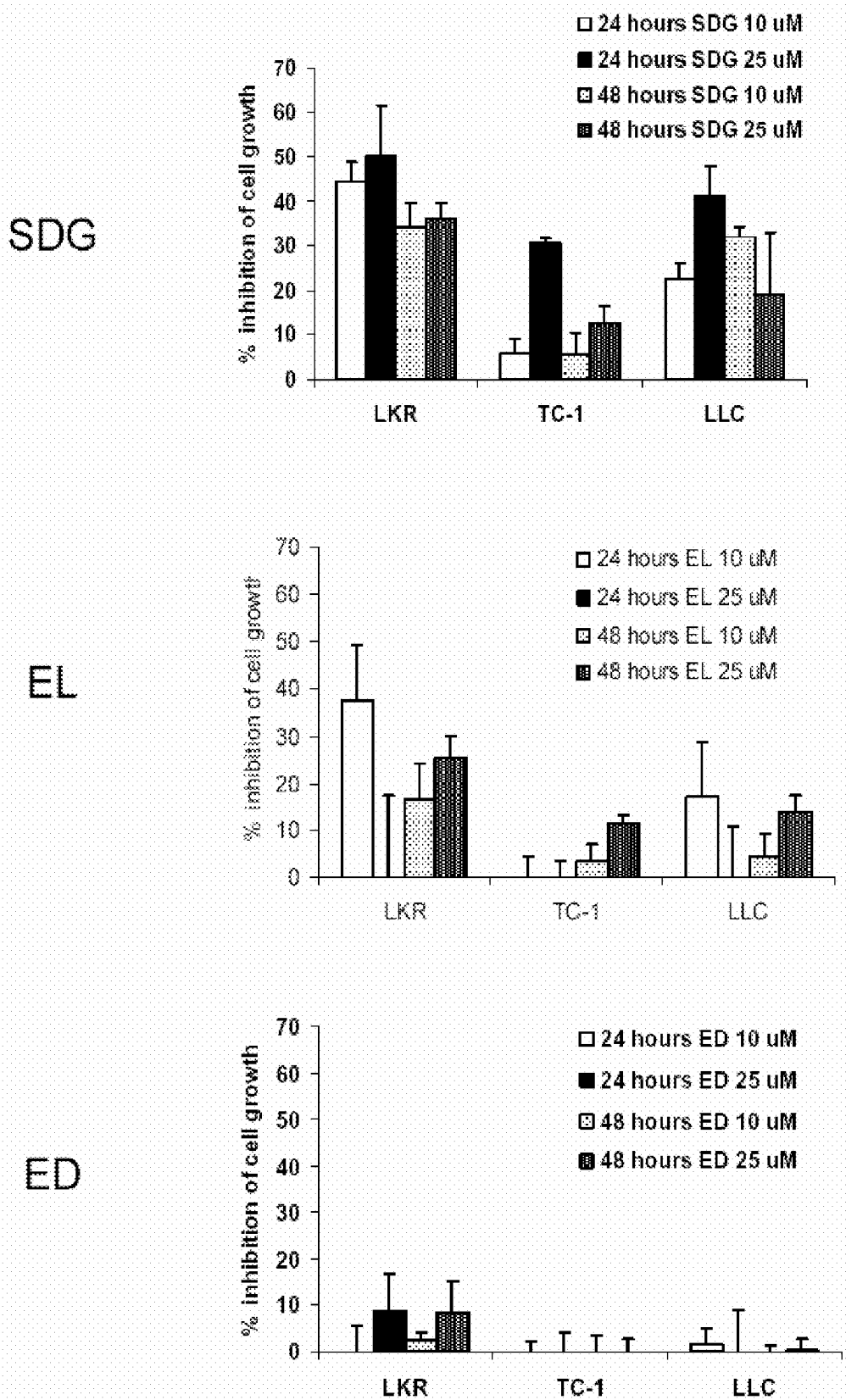
FIG. 37: FS lignans EL and ED, and their precursor SDG, inhibit cell proliferation in tumor cell lines. Tumor cell lines (LKR, TC-1, and LLC) were incubated with 10 μM or 25 μM of SDG, EL, or ED for 16 hours and processed for MTS assay to measure cell proliferation. The % inhibition of cell growth compared to untreated (no lignan) cell lines was calculated. Bars represent means±SEM. n=3 readings per group.

The three cell lines that showed a response to FS feeding in our flank model were incubated with the FS lignans SDG, EL, and ED at 10 µM for 16 hours. Cell proliferation was assessed at this time (time 0), and 24 and 48 hours later. As seen in FIG. 37, flaxseed lignans ED and E1 and the lignan precursor SDG induce a significant decrease of cancer cell proliferation rate when given at physiological doses (micromolar concentrations).

Thus wholegrain flaxseed diet has potent chemopreventive properties making this dietary agent an attractive candidate in lung cancer chemoprevention.

Example 22

Dietary Flaxseed Administered Post-Thoracic Radiation Treatment Improves Survival and Mitigates Radiation-Induced Pneumonopathy in Mice Flaxseed (FS) is a dietary supplement having antioxidant and anti-inflammatory properties. Radiation exposure of lung tissues can occur either when given therapeutically to treat intrathoracic malignancies or when occurring incidentally such as in the case of exposure from inhaled radioisotopes released after the detonation of a radiological dispersion devise (RDD). Such exposure is associated with pulmonary inflammation, oxidative tissue damage and irreversible lung fibrosis. Dietary FS prevents pneumonopathy in a rodent model of thoracic X-ray radiation therapy (XRT). However, its therapeutic usefulness in mitigating radiation effects post-exposure, has never been evaluated.

We evaluated the effects of a 10% FS or isocaloric control diet given to mice in 2 separate experiments (n=20-30 mice/group) on 0, 2, 4, 6 weeks post a single dose 13.5 Gy thoracic XRT and compared it to an established radiation-protective diet given preventively, at 3 weeks prior to XRT. Lungs were evaluated four months later for blood oxygenation levels, inflammation and fibrosis.

Irradiated mice fed a 0% FS diet had a 4-month survival rate of 40% while irradiated, FS-fed mouse groups had 70-88% survival. Additionally, all irradiated 10% FS-fed mice had decreased fibrosis compared to those fed 0% FS. Lung hydroxyproline content ranged from 96.5±7.1 to 110.2±7.7 µg/ml (Means±Standard Error of Means) in irradiated, 10% FS mouse groups as compared to 138±10.8 µg/ml for mice on 0% FS. Bronchoalveolar lavage (BAL) protein and weight loss associated with radiation cachexia was significantly decreased in all FS groups. Inflammatory cell influx in lungs also decreased significantly except when diet was delayed by 4 and 6 weeks post XRT. All FS-fed mice (irradiated or not), maintained a higher blood oxygenation level compared to mice on 0% FS. Similarly, multiplex cytokine analysis in the BAL fluid revealed significant decrease of specific inflammatory cytokines in FS-fed mice.

Dietary FS given post-irradiation mitigates radiation effects by decreasing pulmonary fibrosis, inflammation, inflammatory cytokine secretion and lung damage while enhancing mouse survival. Dietary supplementation of FS can be a useful adjuvant treatment mitigating adverse effects of radiation in individuals exposed to inhaled radioisotopes or incidental radiation.

Materials and Methods

Animals

Our studies used female C57/B16 mice, a strain well characterized in the field of pulmonary radioprotection. Mice were obtained from Charles River (Wilmington, Mass.) and irradiated at 6-8 weeks of age under animal protocols approved by the Institutional Animal Care and Use Committee (IACUC) of the University of Pennsylvania.

Diets and Dietary Treatments

Figure 38:
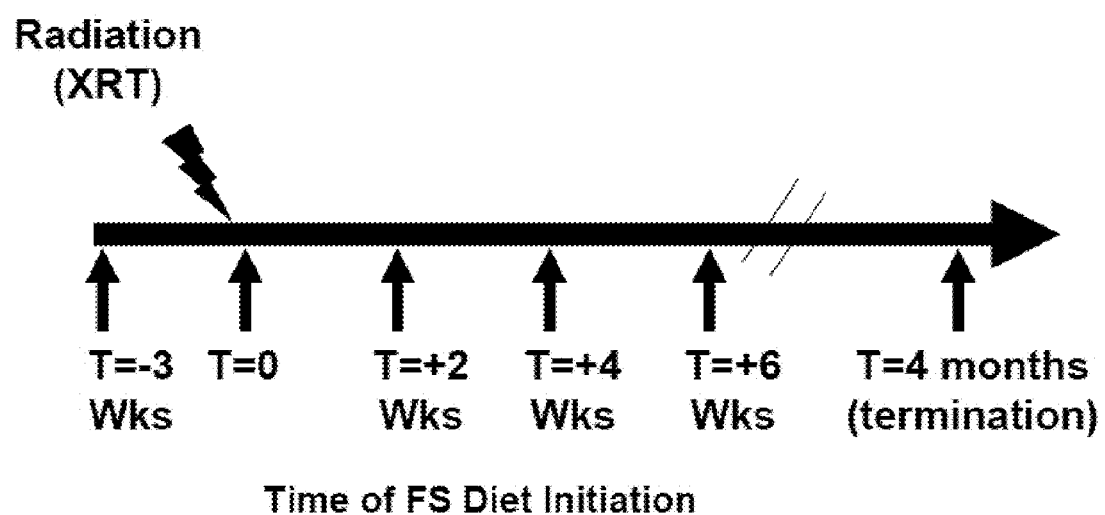
FIG. 38: Experimental Plan. Mice were fed with 0% or 10% FS diet initiated prior (−3 weeks) or post (+2, +4, +6 weeks) single fraction X-ray radiation (13.5 Gy) therapy (XRT). Mice were sacrificed at 4 months post-XRT.

Semi-purified AIN-93G diet was used as the base diet which was supplemented with 10% (w/w) FS. Control and experimental diets were isocaloric and identical in physiological fuel value. Whole ground yellow FS (Lot# 1012338) was provided by Dr. James Hammond at North Dakota State University, Fargo, N. Dak. Diets were administered as described in FIG. 38.

Radiation Procedure

Mice were irradiated as previously described. Briefly, using a customized jig that allows thoracic irradiation of up to 8 mice simultaneously while shielding the head and abdomen/pelvis, 13.5 Gy was delivered to mid-plane using a 250 kVp orthovoltage machine with a 2 mm copper filter and a tube current of 13 mA.

Analytical Evaluation of Lignan Content in Murine Plasma Samples

Figure 39:
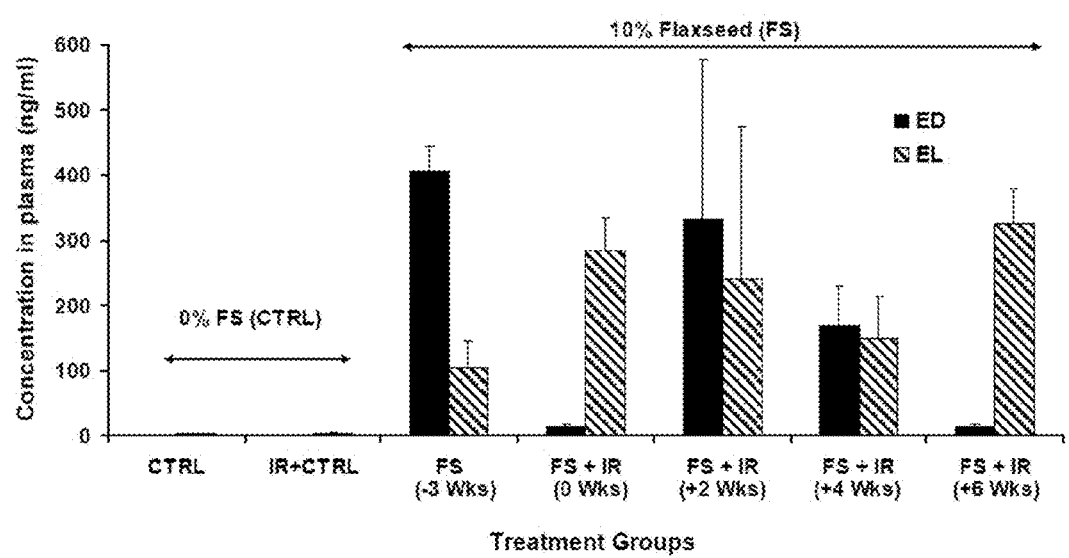
FIG. 39: Detection of flaxseed lignan metabolites in blood. Circulating lignan (ED and EL) levels in plasma of mice, 4 months post-XRT were determined using GC/MS/MS. Mice were fed with 0% or 10% FS diet initiated prior (−3 weeks) or post (+2, +4, +6 weeks) X-ray radiation therapy (XRT). Data is represented mean±SEM (n=3 mice per group). The white, black, gray and hatched bars represent untreated control, 0% FS+XRT, 10% FS and 10% FS+XRT groups, respectively.

Circulating plasma levels of the flaxseed lignans ED and EL at time of sacrifice (4 months' post-XRT) were determined by liquid chromatography tandem mass spectrometry (LC/MS/MS) using commercially available standards in 95% purity (Chromadex, Inc., Santa Ana, Calif.) shown in FIG. 39. Plasma flaxseed lignan levels were evaluated in 3 randomly selected mice per group (irradiated mice; diet initiated at −3, 0, +2, +4, +6 weeks of radiation exposure).

Bronchoalveolar Lavage Fluid Analysis

Mice were sacrificed using an overdose of ketamine (100 mg/mL) and xylazine (20 mg/mL) at 4 months post irradiation. Bronchoalveolar lavage (BAL) was then performed through a 20-gauge angiocatheter (BD Pharmingen, San Diego, Calif.), with the intra-tracheal instillation of 1 mL phosphate-buffered saline (PBS) containing an anti-protease cocktail (Sigma) and 5 mM EDTA given in 0.5 mL increments. Approximately 900 µL of BAL fluid was recovered from each instillation and a 200 µL aliquot was immediately removed to to measure total leukocyte cell counts (cells/mL BAL fluid) using a Coulter Cell and Particle Counter (Beckman Coulter, Miami, Fla.). The remaining lavage fluid was centrifuged at 1,200 rpm for 10 min and the cell-free supernatant was frozen at −80° C. for cytokine and protein analysis.

The amount of total protein in the BAL fluid was assayed using the BCA Protein Assay Kit (Pierce, Rockford, Ill.). In accordance with manufacturer's instructions, 25 µL of cell-free BAL supernatant per sample was added to wells of a 96-well plate. Absorbance at 560 nm (MRX Microplate Reader, Dynatech Laboratories, Chantilly, Va.) was read to yield protein levels in mg/mL BAL fluid.

Multiplexed Cytokine Analysis

The cytokine concentrations in the BAL fluid was assayed using a Invitrogen's Mouse Cytokine 20-Plex Panel (LMC0006) using Multiplex Bead array Immunoassay technology. This approach permits simultaneous quantification of multiple cytokines in solution by capturing them onto antibody coated spectrally distinct fluorescent microspheres, and measuring fluorescence intensity using the BioPlex 200 (Bio-Rad Laboratories, Hercules, Calif.) system. The kit quantified 20 mouse cytokines and chemokines: FGF-basic, Granulocyte Macrophage Colony-Stimulating Factor (GM-CSF), Interferon-γ (IFN-γ), Interleukin (IL)-1α, IL-β, IL-2, IL-4, IL-5, IL-6, IL-10, IL-12 (p40/p70), IL-13, IL-17, IP-10, keratinocyte-derived chemokine (KC), Monocyte Chemoattractant Protein-1 (MCP-1), Macrophage Inflammatory Protein-1α (MIP-1α), MIG, Tumor Necrosis Factor-α (TNF-α), and Vascular endothelial growth factor (VEGF). The assay was performed according to the manufacturer's protocol. All the samples were run in duplicate. The detection limit of this kit is in pg/ml for all the included cytokines.

Tissue Harvesting and Evaluation of Oxidative Lung Injury

Radiation experiments were terminated after 16 weeks, corresponding to a time point when radiation-induced fibrosis is readily detectable in our model using both biochemical assays and histopathological evaluation. For histological studies, the lungs were instilled prior to removal from the animal with 0.75 ml of buffered formalin through a 20-gauge angiocatheter placed in the trachea, immersed in buffered formalin overnight, and processed for conventional paraffin histology. Sections were stained with hematoxylin and eosin, and examined by light microscopy. Malondialdehyde (MDA), an indicator of oxidative stress was measured in homogenized lung tissues using a commercially available kit (OXIS International, Portland, Oreg.) according to manufacturer's recommendations. The results were expressed as µmol MDA/g lung protein.

Oxygen Saturation Measurements

We used a mouse-adapted Pulse-oximeter (Starr Life Sciences, Oakmont, Pa.) as a non-invasive clinical readout of lung function post XRT in mice. Mice were shaved around the neck area to remove black hair that interfered with detection, and a pulse-oximeter clip was placed on the neck, over the carotid arteries. Mice were left to walk freely in a small chamber covered by a light blocking fabric supplied by the manufacturer. In some instances, mice were pre-adopted to the feeling of the neck sensor collar by adding a mock collar on them for a day prior to evaluation. Three minute readings were taken from each mouse, sorted by spreadsheet for readings that had no error codes in a block, and the average of all individual readings was calculated (usually those ranged from 1000-3000). On a limited number of mice, arterial blood gas analysis of carotid blood was performed using an i-STAT blood gas analyzer (Abbott Laboratories, East Windsor, N.J.) using G3+ cartridges and results compared to those from pulse oximetry.

Quantitative and Semi-Quantitative Assessment of Fibrosis

Whole collagen content of mouse lung was evaluated quantitatively by determining hydroxyproline content using acid hydrolysis according to Woessner et al. The data is expressed as µg hydroxyproline/whole lung. Semi quantitative evaluation of fibrosis was done histologically by determining a radiation Fibrotic Index (FI).

Statistical Analysis

Results are expressed as mean±SEM. Statistical differences among groups were determined using one-way analysis of variance (ANOVA). When statistically significant differences were found (p<0.05) individual comparisons were made using the Bonferoni/Dunn test (Statview 4.0). We used the Cox proportional-hazard model with a time-varying predictor to evaluate the effect of FS administration on animal survival (Proc Phreg; SAS Version 9.2; SAS Institute, Cary, N.C.).

Results

Detection of Lignan Content in Murine Plasma.

Detection of flaxseed metabolites in the circulation using analytical methods was used to confirm that mice were feeding on the flaxseed-supplemented diet to reach physiologically relevant levels. Mice were maintained on control (0% FS) or treatment (10% FS) diets given ad libitum for either three weeks prior to XRT and for the entire duration of the experiment (4 months), or started on the day of XRT or 2,4,6 weeks post XRT and continued for 4 months (see scheme on FIG. 38). Plasma evaluation for lignan detection was done at 16 weeks post XRT.

Indeed (FIG. 39), although variable, both ED and EL were detectable in all FS-fed mouse groups 4 months post-irradiation while no ED or EL was detectable in the control-diet fed mice. Levels ranged from 14-405 ng/ml plasma for ED and 103-325 ng/ml for EL.

Dietary Flaxseed Ameliorates Radiation-Induced Cachexia and Boosts Survival When Given Post Radiation Exposure.

Figure 40:
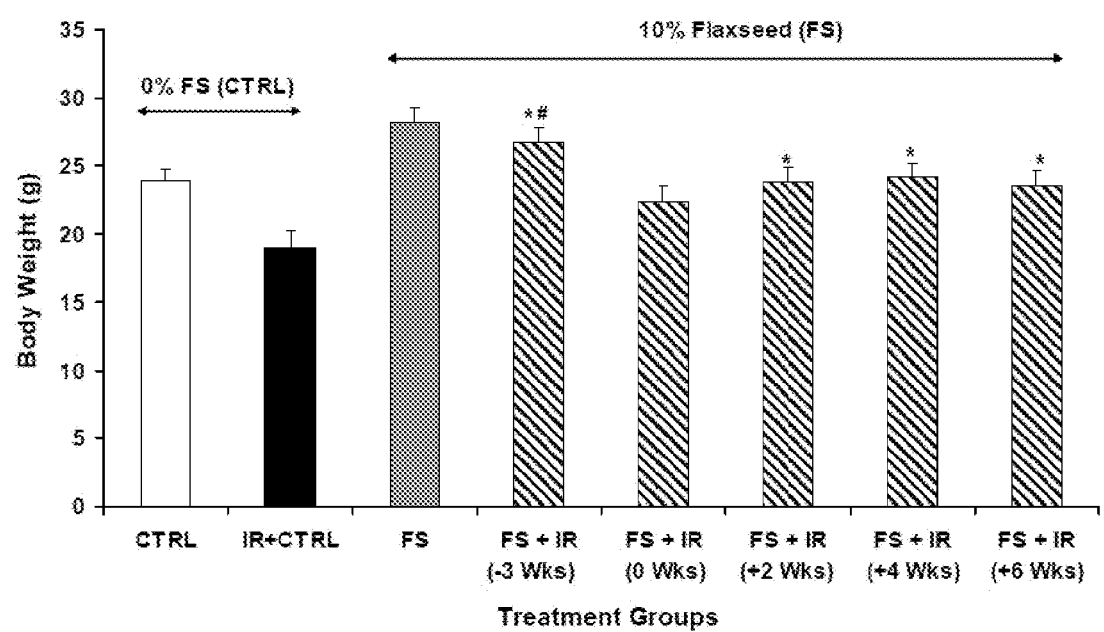
FIG. 40: Effect of Flaxseed (FS) diet on body weight of mice 4 months post-XRT. Mice were fed with 0% or 10% FS diet prior (−3 weeks) or post (+2, +4, +6 weeks) X-ray radiation therapy (XRT). Body weight was recorded at 4 months post-irradiation. Data is represented mean±SEM of two independent experiments (n=20-30 mice per group). The white, black, gray and hatched bars represent untreated control, 0% FS+XRT, 10% FS and 10% FS+XRT groups, respectively. The dotted line represents weight average in non-irradiated control animals. *p<0.01 for irradiated 0% FS vs. irradiated 10% FS, $p<0.01 for irradiated vs. non-irradiated 0% and #p<0.05 irradiated 10% FS (initiated 3 weeks prior to XRT) vs. all irradiated 10% FS (diet initiated on, or post-XRT).
Figure 41:
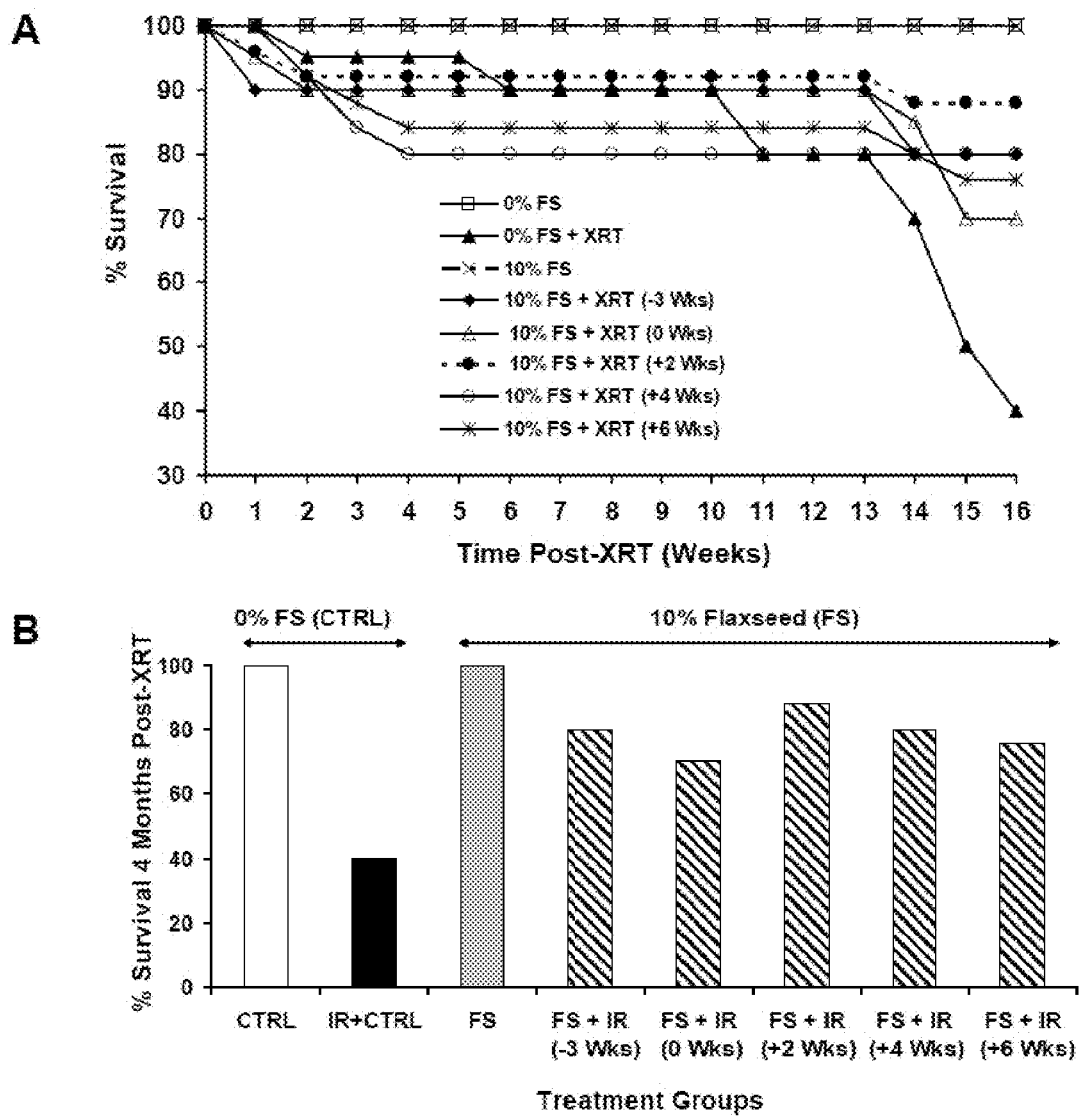
FIG. 41: Effect of Flaxseed (FS) diet on the survival of mice 4 months post-XRT. Mice were fed with 0% or 10% FS diet prior (−3 weeks) or post (+2, +4, +6 weeks) X-ray radiation therapy (XRT) and observed for survival up to 16 weeks post-irradiation. Data is represented mean±SEM of two independent experiments (n=20 and 30 mice in non-irradiated and irradiated groups, respectively). Panel A: Kinetics of mouse survival. Panel B: Mouse survival 4 months post-XRT. The white, black, gray and hatched bars represent untreated control, 0% FS+XRT, 10% FS and 10% FS+XRT groups, respectively. *p<0.01 and **p<0.05 for irradiated 0% FS vs. irradiated 10% FS.

Radiation-induced pneumonopathy is associated with cachexia measured by loss in body weight. We therefore evaluated the effect of post-irradiation administration of 10% FS diet on XRT-induced loss in body weight (FIG. 40) and survival (FIG. 41) of mice. Although designed to be isocaloric, the 10% FS diet given to non-irradiated mice let to a significant (p<0.007) difference in body weight (28.2±1.07 g) as compared to non-irradiated mice on the 0% FS, control diet (23.8±0.83 g). A fair comparison, therefore, of dietary treatments (0% vs. 10%) would be to compare each diet regimen with the non-irradiated counterparts. XRT decreased the body weight (18.9±1.37 g) of animals on the 0% control diet significantly (p<0.01) as compared with their non-irradiated counterparts. Remarkably, the 10% Flaxseed supplementation, whether given 3 weeks prior to irradiation or several weeks thereafter, significantly prevented weight loss to levels seen in irradiated mice on the control diet. The only exception was the condition where diet was initiated on the day of irradiation. Mice in that group maintained a weight not significantly different than the 0%+XRT group.

XRT (13.5 Gy, 0% FS)-induced radiation sickness and early mortality was observed in all groups, albeit to variable degree, within the first 2-3 weeks of exposure (FIG. 41A). We have previously observed this effect and attributed this early death to poor oral intake possibly from esophagitis. Later deaths, occurring in weeks 8-16 are attributed to radiation pneumonopathy. However, by the termination of the experiment, 4 months post XRT, only 40% of animals survived in the irradiated group (0% FS), as compared to the non-irradiated counterparts (FIG. 41B). These values fall within the observed survival rate, given that the selected dose of 13.5 Gy reflects the LD50 as shown in our previous studies. Remarkably, 10% FS diet led to a significant (p<0.05) increase in the survival of animals in all groups when compared with irradiated group (XRT, 0% FS). When 10% FS diet was started preventively, i.e., 3 weeks prior to XRT, survival was enhanced significantly (80%; p<0.05) in comparison to irradiated group, a finding in agreement with previous observations. Remarkably, flaxseed diet, when given therapeutically, i.e. initiated post-XRT, enhanced the survival of all irradiated animal groups. When 10% FS diet was given to animals up to 6 weeks post-irradiation, animal survival increased significantly (p<0.05).

Dietary FS Improves Pulmonary Hemodynamics and Mitigates Pulmonary Inflammation and Oxidative Lung Injury When Given Post Thoracic XRT Thoracic radiation is associated with pneumonopathy characterized by inflammatory cell influx and pulmonary edema. We have previously shown that preventive use of dietary FS decreased radiation-induced lung damage and inflammation. To test, whether FS also mitigates these effects when administered at variable times post a radiation challenge, we delayed the dietary administration (0, 2, 4, 6 weeks) and evaluated bronchoalveolar lavage (BAL) 4 months post-XRT, a time known from previous studies to be associated with measurable lung damage parameters. We confirmed BAL findings with a histopathological evaluation of lungs in mice belonging in the same groups of mice, which, however, were not lavaged, so that histological evaluation would not be compromised.

Figure 42:
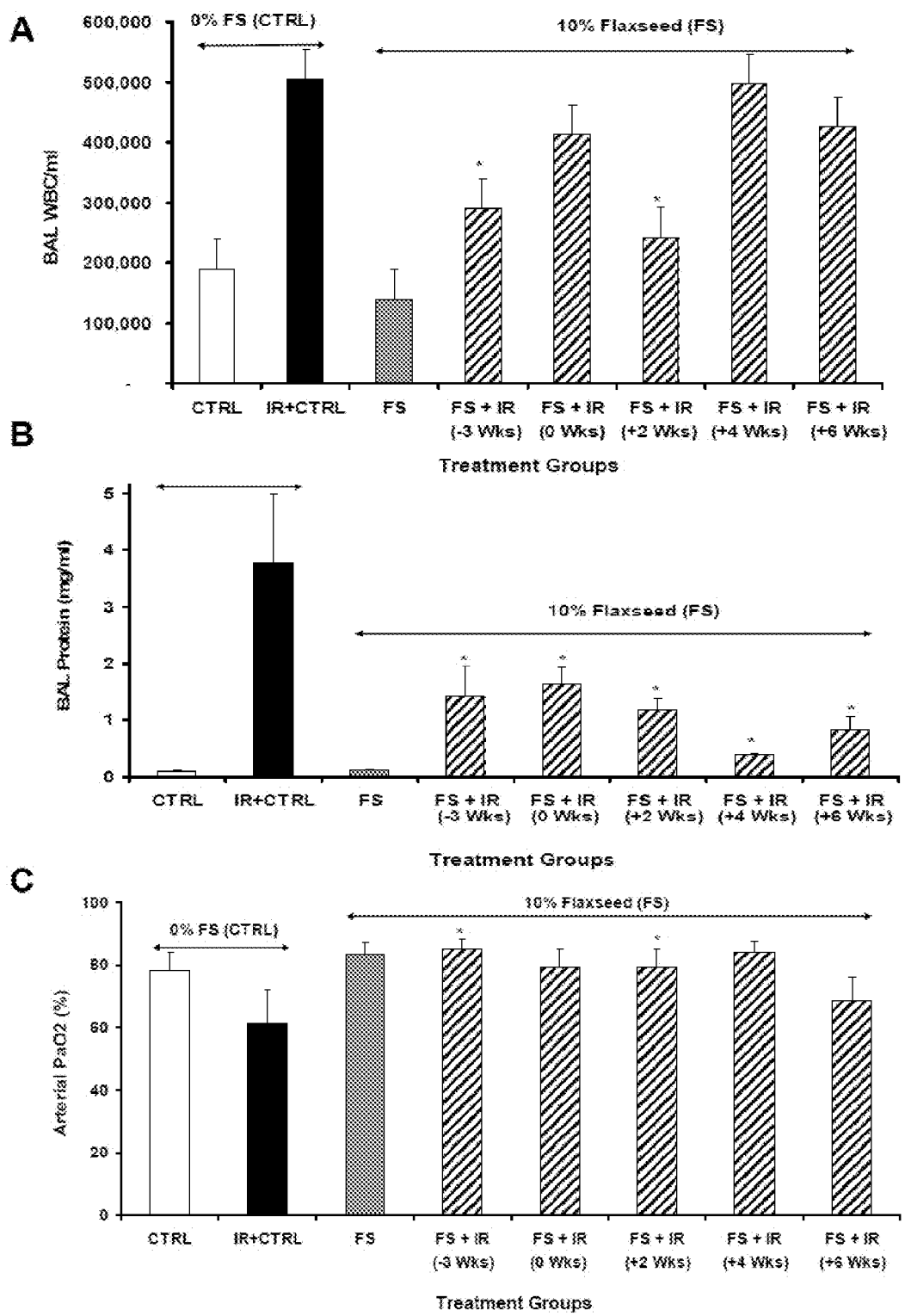
FIG. 42: Evaluation of Lung Injury, Inflammation and Blood Oxygenation Levels in mice 4 months post-XRT. Mice were fed with 0% or 10% FS diet at designated times (−3, 0, +2, +4, +6 weeks) of X-ray radiation therapy (XRT). Data is represented mean±SEM of two independent experiments (n=20-30 mice per group). Panel A: Total WBC counts in bronchoalveolar lavage (BAL) of irradiated (13.5 Gy, XRT) mice after 4 months. *p<0.05 for irradiated 0% FS vs. irradiated 10% FS Panel B: Total proteins in bronchoalveolar lavage (BAL) of mice after 4 months. *p<0.01 for irradiated 0% FS vs. irradiated 10% FS Panel C: Arterial O2 levels were measured using pulse oximetry in irradiated (13.5 Gy, XRT) mice after 4 months. The white, black, gray and hatched bars represent untreated control, 0% FS+XRT, 10% FS and 10% FS+XRT groups, respectively. *p<0.05 for irradiated 0% FS vs. irradiated 10% FS.
Figure 43:
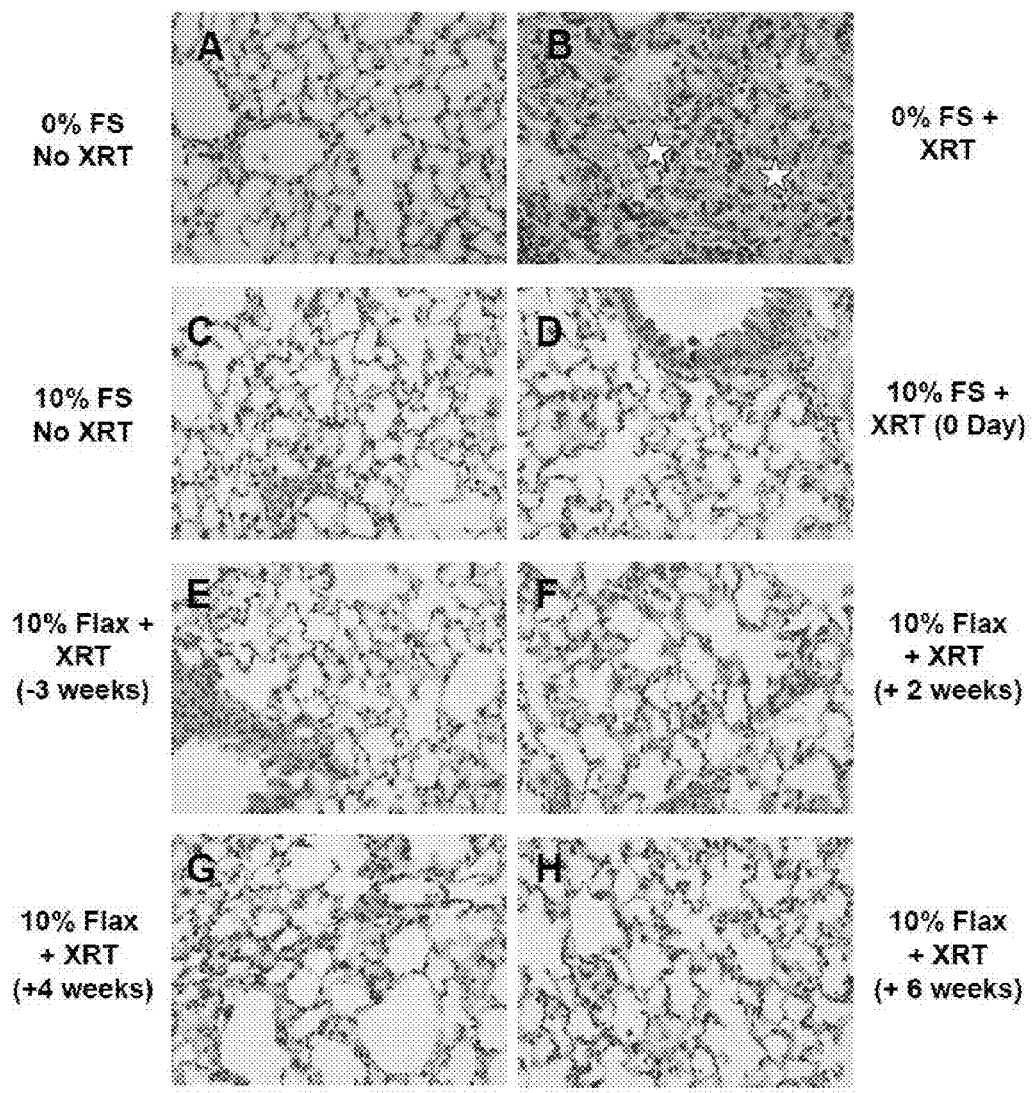
FIG. 43: Histological evaluation of lung H&E-stained sections post-XRT (4 months). Mice were fed with 0% or 10% FS diet prior (−3 weeks) or post (+2, +4, +6 weeks) X-ray radiation treatment (XRT). Lungs were harvested 4 months post single fraction XRT and processed for histology. Asterisks designate proteinaceous exudate in alveolar spaces.

We observed a significantly reduced inflammatory cell influx (FIG. 42A) in the BAL fluid from lungs in all irradiated mouse groups fed with 10% FS diet as compared with those on control diet, regardless of the time the diet was initiated (pre- or post-XRT). Alveolar protein level is a marker for increased lung permeability and lung injury. Alveolar protein exudate was increased 37-fold (3.78±1.19 mg/ml) in mice 4 months post-XRT (FIG. 42B) in comparison to untreated controls (0.1±0.013 mg/ml). These findings correlated with the histopathological evaluation (FIG. 43). In summary, FS diet significantly (p<0.05) decreased lung injury and edema by decreasing the XRT-induced alveolar protein levels irrespective of therapeutic or preventive administration.

Radiation pneumonopathy is also associated with compromised pulmonary function resulting in poor oxygenation levels as modeled in rodent models. Pulse oximetry is a non-invasive way of determining arterial blood oxygenation levels (FIG. 42C). XRT notably decreased the percentage of arterial O2 levels (61.4%±10.77%) in mice fed with 0% control diet in comparison to untreated control animals (78.5%±5.33%). Mice Fed with 10% FS diet had an increase percentage of arterial O2 levels compared to mice fed 0% diet following XRT. FS diet enhanced blood oxygenation, thus improving pulmonary hemodynamics in irradiated mice irrespective of whether it was given therapeutically or preventively.

Dietary FS Mitigates Oxidative Lung Changes when Given Post Thoracic XRT

Figure 44:
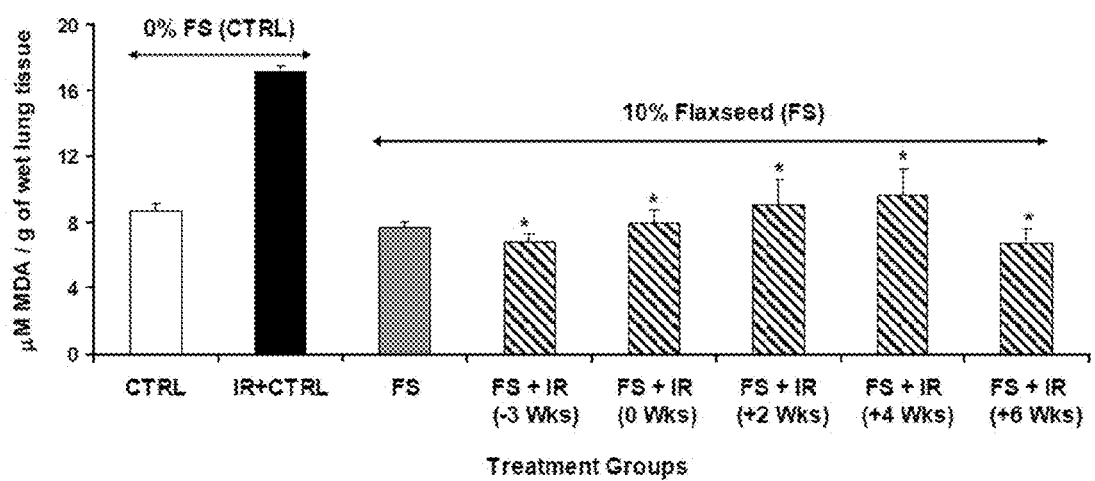
FIG. 44: Effect of 10% FS diet on lung lipid peroxidation levels 4 months post-XRT. Mice were fed with 0% or 10% FS diet prior (−3 weeks) or post (+2, +4, +6 weeks) X-ray radiation therapy (XRT). Lungs were harvested after 4 months, homogenized and assayed for lipid peroxidation by measuring Malondialdehyde (MDA) levels. MDA is calculated per g of wet lung tissue. Data is represented mean±SEM of two independent experiments (n=20-30 mice per group). The white, black, gray and hatched bars represent untreated control, 0% FS+XRT, 10% FS and 10% FS+XRT groups, respectively. *p<0.0002 for irradiated 0% FS vs. irradiated 10% FS.

Lipid peroxidation plays a major role in mediating oxidative-damage in tissues. Thoracic irradiation-induced oxidative degradation of unsaturated fatty acids can be followed by determining the amount of a product, malondialdehyde (MDA), of lipid peroxidation in lung tissues. A significant two-fold increase in MDA levels was recorded in irradiated animals fed with control diet as compared to unchallenged controls (FIG. 44). In contrast, mice fed with a 10% FS diet (whether preventively or therapeutically) maintained a significantly (p<0.005) lower MDA level at 4 months post-XRT in all the treatment groups (diet initiated −3 or 0, 2, 4, 6 weeks post XRT) as compared to irradiated mice fed with 0% FS, control diet. Importantly, no statistical difference was found among any of the irradiated FS-fed groups (FIG. 44, hatched bars) and the non-irradiated FS group (FIG. 44, grey bar).

Figure 45:
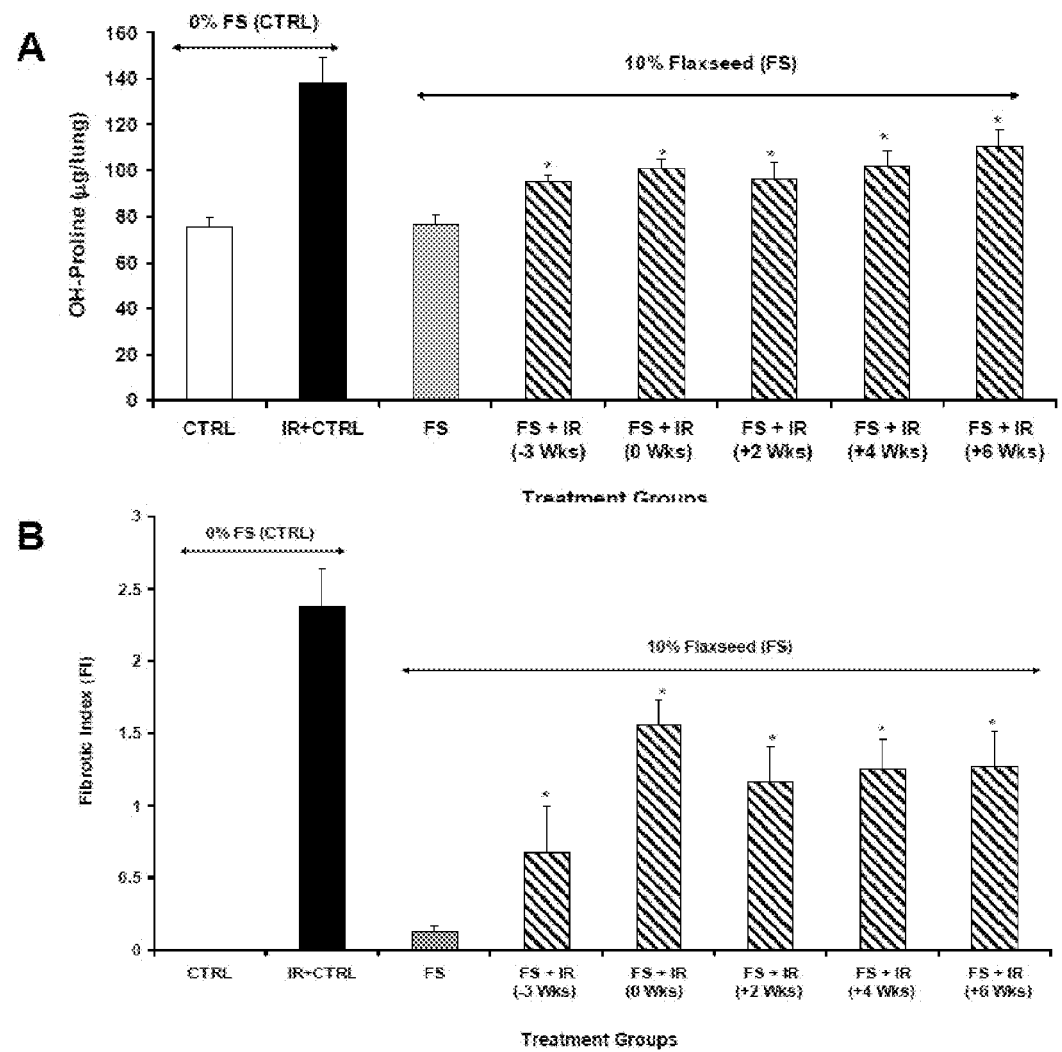
FIG. 45: Determination of fibrotic changes in mouse lungs 4 months post-XRT. Panel A: Evaluation of hydroxyproline content in lungs of irradiated (13.5 Gy, XRT) mice. Mice were fed with 0% or 10% FS diet prior (−3 weeks) or post (+2, +4, +6 weeks) X-ray radiation therapy (XRT). Lungs were harvested after 4 months and hydroxyproline assay was performed. *p<0.005 for irradiated 0% FS vs. irradiated 10% FS. Panel B: Fibrotic Index range=0-4) Data is represented mean±SEM of two independent experiments (n=20-30 mice per group). The white, black, gray and hatched bars represent untreated control, 0% FS+XRT, 10% FS and 10% FS+XRT groups respectively. *p<0.005 for irradiated 0% FS vs. irradiated 10% FS. *p<0.005 for irradiated 0% FS vs. irradiated 10% FS.

Dietary FS Mitigates Fibrotic Changes in Lung Tissue when Given Post Thoracic Xrt Dietary flaxseed prevents radiation-induced pulmonary fibrosis in mice when given preventively. However, its effects when given therapeutically, i.e., post the radiation challenge, are unknown. To test this, we evaluated the total hydroxyproline (OH-proline) content of murine lungs 4 months post-XRT (FIG. 45A). This is a quantitative measure of collagen deposition and fibrosis in lungs, which is expressed as 1ig OH-proline/lung. XRT led to a significant (p<0.0001), near 2-fold increase of OH-proline in mice (0% FS) in comparison to unchallenged controls. FS diet rendered a noteworthy decline in OH-proline levels in all radiation-challenged mice. Mice fed with 10% FS diet prior or post XRT had significantly (p<0.005) deceased levels of OH-proline content in comparison to those fed with 0% FS following XRT (FIG. 45A).

Figure 46:
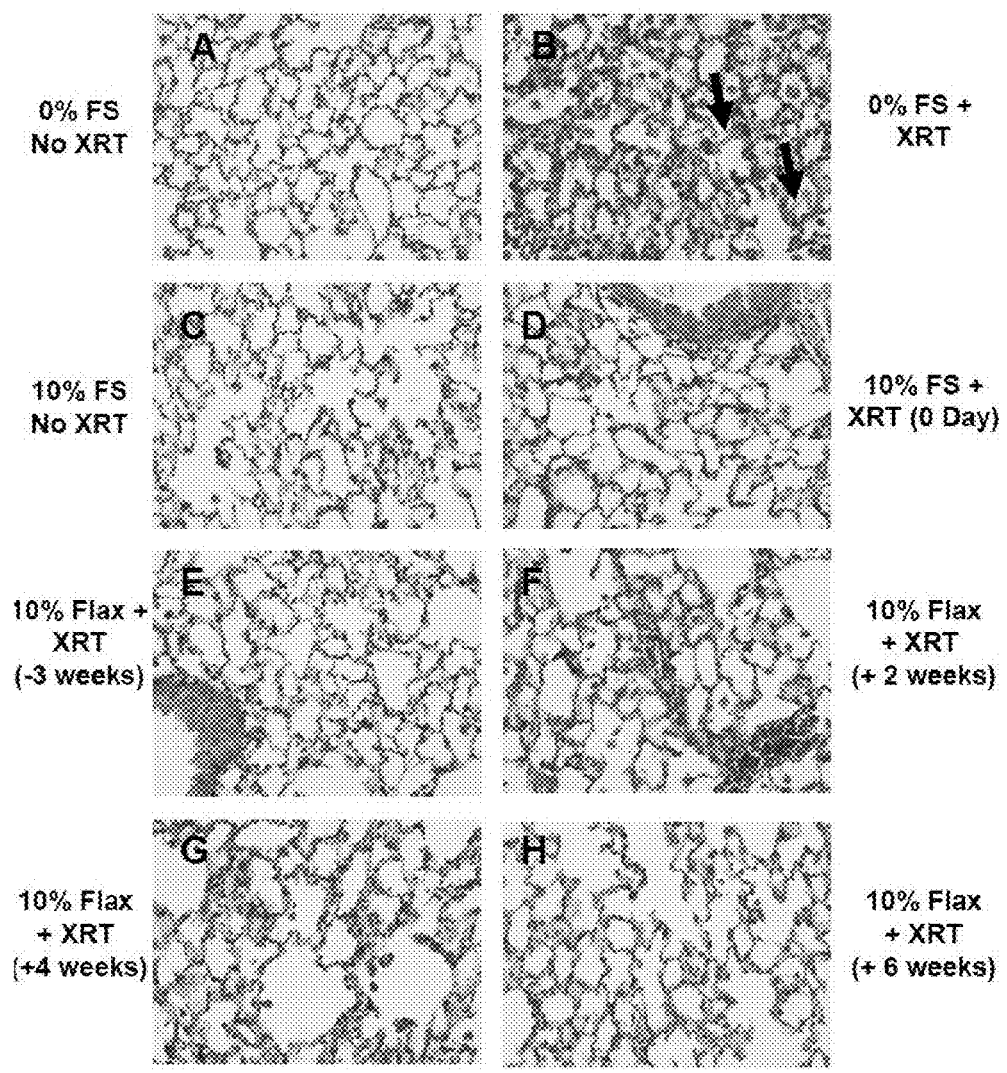
FIG. 46: Histological evaluation of lung Tri chrome-stained sections post-XRT (4 months). Mice were fed with 0% or 10% FS diet prior (−3 weeks) or post (+2, +4, +6 weeks) X-ray radiation treatment (XRT). Lungs were harvested 4 months post single fraction XRT and processed for histology. Arrows designate collagen deposition in lung (blue color).

To further evaluate the degree of XRT-induced fibrosis, and correlate biochemical findings with tissue histology, lungs were also examined histolopathologically using Trichrome staining (FIG. 46) and Fibrotic Index (FI) score, a measure of the extent of lung fibrosis and inflammation was determined for each lung (FIG. 45B). Lungs of irradiated mice fed with 0% FS diet showed severe fibrosis (FIG. 46B, blue color) as compared to non-irradiated mice (0% FS)., the extent of fibrosis was notably reduced in all animal groups fed with 10% FS diet prior or post-XRT when compared to irradiated 0% FS fed mice.

Alterations of Proinflammatory and Pro-Fibrotic Cytokine Profile in the BAL Fluid of FS-fed Mice 4 Months Post XRT.

Thoracic radiation-induced cytokines, chemokines and cell adhesion molecules are implicated in the pathogenesis of pulmonary inflammation, both subacute and chronic, as well as the development of lung fibrosis. To determine whether the beneficial effects of FS given several weeks post a radiation challenge, we evaluated inflammatory cytokine levels in BAL fluid in mice sacrificed 4 months post XRT (Table 1). This time coincides with radiation pneumonitis and the onset of detectable lung fibrosis. Using multiplex cytokine analysis, we analyzed the effect of FS on a panel of 20 cytokines. While half the cytokines (basic FGF, GM-CSF, γ IFN, IL-1α, IL-5, MCP-1, TNFα) were at levels below the detection limit of the assay, 10 cytokines (IL1β, IL-2, IL-4, IL-6, IL-12, IL-17, IP-10, KC, MIG, MIP-a and VEGF) were measurable in the BAL fluid of all mouse groups.

When comparing irradiated mice on control versus any of the FS-supplemented diets, o significant decrease in the levels of IL-1β, IL-2, IL-4, MIG, or MIP-1α was detected. However, levels of IL-6, IL-12, IL-17 and VEGF were significantly lower in irradiated FS-fed mice as compared to irradiated mice on control diet. Notably, even delaying FS diet by as long as 6 weeks post radiation challenge resulted in a several-fold decrease of the above-mentioned cytokines. Moreover, pointed to an alteration of the chronic inflammatory profile of irradiated lungs favoring a mitigated radiation effect as a result of the FS diet.

An ideal radiation mitigator should be safe, effective, have a long shelf life and an easy route of administration. Flaxseed is a dietary supplement that has numerous medicinal, anti-inflammatory and antioxidant properties due to its high content of lignans and omega-3 fatty acids. FS and its bioactive components have been extensively studied for their anti-inflammatory, anticarcinogenic, and anti-atherogenic effects in several organs systems. Importantly, prolonged FS administration has not been associated with any significant toxicity. Therefore, flaxseed can be an effective mitigator of the radiation damage.

Our data showed that 10% FS diet supplementation significantly increased the survival in mice in all the groups (FIG. 41) irrespective of time of initiation of the FS diet (70-88% survival) as compared to the survival of mice fed with 0% FS diet (40% survival). It is evident from our results that FS diet protects mice from XRT-induced mortality whether given therapeutically or preventively.

Results revealed radiation-induced increment in lipid peroxidation in lungs (FIG. 44). Lipid peroxidation (LP) results

TABLE I

Cytokine analysis from BAL fluid 4 months post XRT

| Treatment Groups | IL-1β | IL-4 | IL-6 | IL-12 (p40/p70) | IL-17 | KC | MIG | MIP-1α | VEGF |
|---|---|---|---|---|---|---|---|---|---|
| 0% FS | 26.7 ± 8.3 | 28.6 ± 6.3 | 21.0 ± 5.9 | 19.2 ± 3.1 | 0.6 ± 0.2 | 658.6 ± 39.3 | 15.3 ± 2.5 | 25.4 ± 7.8 | 26.6 ± 4 6 |
| 0% FS + XRT | 12.1 ± 2.7 | 17.4 ± 1.0 | 66.0 ± 42.5 | 88.1 ± 18.2 | 0.4 ± 0.1 | 173.0 ± 47.0 | 11.4 ± 4.2 | 18.5 ± 3.7 | 43.9 ± 4.5 |
| 10% FS | 14.4 ± 5.1 | 20.4 ± 2.3 | 16.6 ± 2.0 | 12.9 ± 1.3 | 0.4 ± 0.1 | 730.7 ± 58.4 | 14.6 ± 4.4 | 16.5 ± 3.0 | 21.1 ± 2.9* |
| 10% FS + XRT (0 Day) | 12.4 ± 0.8 | 18.2 ± 0.3 | 20.4 ± 1.1$ | 51.1 ± 13.3$ | 0.6 ± 0.1 | 521.0 ± 165.0* | 20.9 ± 4.9 | 13.3 ± 1.5 | 21.4 ± 3.8* |
| 10% FS + XRT (−3 wks) | 14.7 ± 1.5 | 17.9 ± 0.6 | 28.0 ± 6.4 | 54.2 ± 13.6* | 0.9 ± 0.3* | 396.0 ± 49.3 | 14.8 ± 2.8 | 15.7 ± 1.6 | 16.9 ± 3.4* |
| 10% FS + XRT (+2 wks) | 13.1 ± 2.9 | 15.9 ± 1.0 | 16.6 ± 1.7* | 43.2 ± 7.9* | 0.3 ± 0.1§§ | 380.5 ± 162.7 | 7.2 ± 2.0 | 14.5 ± 1.7 | 13.4 ± 1.3* |
| 10% FS + XRT (+4 wks) | 7.4 ± 1.0 | 16.6 ± 0.6 | 13.0 ± 1.8* | 16.2 ± 1.2*§ | 0.1 ± 0.0§§ | 444.0 ± 66.8 | 8.8 ± 1.6 | 10.0 ± 1.2 | 6.8 ± 2.2* |
| 10% FS + XRT (+6 wks) | 7.7 ± 1.2 | 16.5 ± 0.9 | 15.3 ± 1.7$ | 26.8 ± 7.1* | 0.2 ± 0.0§§ | 264.7 ± 150.7 | 9.0 ± 4.8 | 10.0 ± 2.1 | 11.7 ± 1.8* |

Values are mean ± SEM of two independent experiments. n = 20-30 in non irradiated and irradiated groups respectively.
$p ≤ 0.05,
*p ≤ 0.01,
p ≤ 0.0005, for 0% FS irradiated vs. 10% FS irradiated groups.
§p ≤ 0.05,
§§p ≤ 0.01 for 10% FS given preventively to XRT Vs 10% FS started therapeutically post-XRT.

Table 1 shows evaluation of cytokine levels in BAL of mice 4 months post-XRT. Mice were fed with 0% or 10% FS diet prior (−3 weeks) or post (+2, +4, +6 weeks) X-ray radiation therapy (XRT) and sacrificed after 4 months. Lungs were lavaged and cytokine levels in BAL were measured. Data is represented mean±SEM of two independent experiments (n=20 and 30 mice in nonirradiated and irradiated groups, respectively).

We demonstrate here for the first time, the role of FS in boosting survival and mitigating the acute and chronic damage induced by X-ray radiation exposure of lung tissues when administered days and even weeks post the initial radiation exposure. Results from our study show that FS significantly ameliorates the XRT-induced damage by improving survival and body weight of mice fed with FS not only given diet prior to but 2, 4 and 6 weeks after XRT. We also found that FS diet mitigated the deleterious effects of XRT by a) improving pulmonary hemodynamics and blood oxygenation levels, as well as by b) decreasing lung injury by decreasing BAL protein levels, c) pulmonary fibrosis by decreasing collagen content of lung tissues, d) lung inflammation by decreasing WBC influx into the airways and e) oxidative modification of mouse lungs as evidenced by levels of lipid peroxidation. BAL cytokine analysis, moreover, from a cascade of events induced by radiation in biological membranes. FS diet led to a significant drop off in the LP levels in all the FS-fed experimental mouse groups.

Our current study showed for the first time that fibrotic processes can be blunted in pulmonary tissues even when the protective agent is given post-radiation damage, i.e., as a radiation mitigator. Despite notable and significant benefits of a therapeutic usefulness of FS diet (i.e., when initiated at 0, +2, +4 and +6 weeks post XRT), however, the fact remained that FS-mediated decline in both lung OH-proline levels and FI was more prominent when diet was started preventively, i.e, 3 weeks prior to XRT. This is the first time that any botanical or chemical agent is indicating mitigation of fibrotic changes effect in lungs.

In the present study, we evaluated the effect of FS diet on inflammatory cytokines in the late phase of thoracic radiation-exposed mice. The cytokine levels seen in lung tissues and fluids in our model reflect levels comparable to those in chronic inflammation and not in acute responses. Several cytokines associated with inflammation were significantly lower in irradiated FS-fed mice as compared to irradiated mice on control diet, while none of the rest was significantly aggravated by the FS diet. Our studies show, for example, a sustained 3-fold increased BAL level of IL-6 in radiation-exposed mice if fed a control diet while dietary supplementation of flaxseed given even weeks post initial insult, decreased IL-6 levels, reflecting a low inflammatory state of lung tissues.

Because radiation damage is a multi-faceted phenomenon, any agent or compound that can modify or alter multiple aspects or mechanisms of radiation-induced inflammation and fibrosis while at the same time being both inexpensive and non-toxic is extremely exciting. It is evident from our findings that dietary FS is a potential agent in mitigating radiation damage and that the discovery of the mitigating properties of FS may be prove a critical milestone in the development of non-toxic radiation mitigators.

Example 23

Flaxseed Lignan Complex (FLC) Enriched in Secoisolariciresinol Diglucoside (SDG) Prolongs Survival And Protects Against Radiation-Induced Pneumonopathy in Mice Flaxseed (FS), has potent anti-inflammatory and antioxidant properties in mouse models of acute and chronic lung injury. It is not known, however, which bioactive ingredient contributes to the protective effects. In this study we tested the lignan component of FS (FLC) consisting mainly of SDG formulated in rodent chow in a murine model of thoracic-radiation induced lung injury.

Methods

Mice (n=20 per group) were fed an isocaloric control diet or 0.33% or 0.66% FLC corresponding to the lignan content in 10% and 20% wholegrain FS, respectively for 3 weeks. Mice were exposed to a single fraction of 13.5 Gy X-ray thoracic radiation (XRT). Mouse survival, lung inflammation and injury were evaluated 4 months post-XRT in bronchoalveolar lavage.

Results

Survival increased dose-dependently with FLC diet content (100%, 90% and 44% survival in 0.66%, 0.33% and 0% FLC diets, respectively. Wasting due to radiation also decreased with higher FLC content (12%, 15%, 27% weight loss in 0.66%, 0.33% and 0% FLC). Lung inflammation and injury were also abrogated dose-dependently to levels comparable to those of the wholegrain FS diet.

Our results clearly demonstrate that the lignan component of FS, mainly consisting of SDG, is protective against radiation pneumonitis in vivo.

Having described the embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for therapeutically treating a radiation-induced lung disease in a subject in need thereof, the method comprising: administering to said subject a therapeutically effective amount of at least one purified or chemically synthesized lignan, thereby treating said radiation-induced lung disease in said subject, wherein said lignan is selected from secoisolariciresinol diglucoside (SDG), enterodiol (ED), enterolactone (EL), or a combination thereof.

2. The method of claim 1, wherein said radiation-induced lung disease is pulmonary fibrosis.

3. The method of claim 1, wherein said subject is an individual exposed to inhaled radioisotope or incidental or accidental radiation.

4. A method for therapeutically treating radiation-induced pneumonopathy in a subject, the method comprising: administering to a subject having a radiation-induced pneumonopathy a therapeutically effective amount of at least one purified or chemically synthesized lignan, thereby treating said radiation-induced pneumonopathy in said subject, wherein said lignan is selected from secoisolariciresinol diglucoside (SDG), enterodiol (ED), enterolactone (EL), or a combination thereof.

5. A method for therapeutically treating radiation pneumonitis in a subject, the method comprising: administering to a subject having radiation pneumonitis a therapeutically effective amount of at least one purified or chemically synthesized lignan, thereby treating said radiation pneumonitis in said subject, wherein said lignan is selected from secoisolariciresinol diglucoside (SDG), enterodiol (ED), enterolactone (EL), or a combination thereof.

6. A method for improving survival of a subject having a radiation-induced lung disease, said subject exposed to an inhaled radioisotope or incidental radiation, the method comprising: administering to said subject a therapeutically effective amount of at least one purified or chemically synthesized lignan, thereby improving survival of said subject, wherein said lignan is selected from secoisolariciresinol diglucoside (SDG), enterodiol (ED), enterolactone (EL), or a combination thereof.

7. The method of claim 1, wherein, subsequent to administering to said subject said therapeutically effective amount of said at least one lignin, said method further comprises increasing the circulating plasma level of a lignan metabolite in said subject.

8. The method of claim 1, wherein said radiation-induced lung disease is radiation pneumonitis.

* * * * *

UNITED STATES PATENT AND TRADEMARK OFFICE
CERTIFICATE OF CORRECTION

PATENT NO. : 10,045,951 B2
APPLICATION NO. : 13/084408
DATED : August 14, 2018
INVENTOR(S) : Melpo Christofidou-Solomidou It is certified that error appears in the above-identified patent and that said Letters Patent is hereby corrected as shown below:

In the Specification

Replace Lines 17-21 in Column 1 with the following text:
This invention was made with government support under grant numbers ES013508, CA133470, AI081251, and CA016520 awarded by the National Institutes of Health. The government has certain rights in the invention.

Signed and Sealed this
Sixteenth Day of July, 2019

Andrei Iancu
*Director of the United States Patent and Trademark Office*